(12) United States Patent
Tabuchi et al.

(10) Patent No.: US 8,697,397 B2
(45) Date of Patent: Apr. 15, 2014

(54) METHOD OF PRODUCING HETEROGENEOUS PROTEIN

(75) Inventors: Hisahiro Tabuchi, Tokyo (JP); Tomoya Sugiyama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/733,052

(22) PCT Filed: Aug. 6, 2008

(86) PCT No.: PCT/JP2008/064095
§ 371 (c)(1),
(2), (4) Date: Feb. 4, 2010

(87) PCT Pub. No.: WO2009/020144
PCT Pub. Date: Feb. 12, 2009

(65) Prior Publication Data
US 2010/0167346 A1 Jul. 1, 2010

(30) Foreign Application Priority Data
Aug. 7, 2007 (JP) .................................. 2007-205158

(51) Int. Cl.
| | |
|---|---|
| C12P 21/00 | (2006.01) |
| C12P 21/08 | (2006.01) |
| C12N 5/02 | (2006.01) |
| C12N 5/16 | (2006.01) |

(52) U.S. Cl.
USPC .......................... 435/70.3; 435/325; 435/326

(58) Field of Classification Search
None
See application file for complete search history.

(56) References Cited

U.S. PATENT DOCUMENTS

| | | | |
|---|---|---|---|
| 5,658,786 | A | 8/1997 | Smith et al. |
| 6,184,007 | B1 | 2/2001 | Dusch et al. |
| 6,225,115 | B1 | 5/2001 | Smith et al. |
| 6,251,613 | B1 | 6/2001 | Kishimoto et al. |
| 6,316,238 | B1 | 11/2001 | Nakamura et al. |
| 6,812,339 | B1 | 11/2004 | Venter et al. |
| 7,413,536 | B1 | 8/2008 | Dower et al. |
| 7,919,086 | B2 | 4/2011 | Nakano et al. |
| 2003/0165495 | A1 | 9/2003 | Carulli et al. |
| 2005/0221466 | A1 | 10/2005 | Liao et al. |
| 2005/0265983 | A1 | 12/2005 | Melamed et al. |
| 2006/0014937 | A1 | 1/2006 | Kang et al. |
| 2007/0162995 | A1* | 7/2007 | Good et al. ............ 800/278 |
| 2007/0166362 | A1 | 7/2007 | Sakuma et al. |
| 2007/0190599 | A1 | 8/2007 | Nakano et al. |
| 2009/0191591 | A1 | 7/2009 | Tabuchi et al. |
| 2009/0221442 | A1 | 9/2009 | Dower et al. |
| 2010/0233759 | A1 | 9/2010 | Tabuchi et al. |
| 2010/0248359 | A1 | 9/2010 | Nakano et al. |
| 2011/0003334 | A1 | 1/2011 | Tabuchi et al. |
| 2011/0014654 | A1 | 1/2011 | Tabuchi et al. |
| 2012/0045795 | A1 | 2/2012 | Tabuchi et al. |

FOREIGN PATENT DOCUMENTS

| | | |
|---|---|---|
| CN | 1612689 A | 5/2005 |
| CN | 1838969 A | 9/2006 |
| EP | 1 212 619 B1 | 5/2007 |
| EP | 2 213 746 A1 | 8/2010 |
| JP | 08-191693 A | 7/1996 |
| JP | 10-075787 A | 3/1998 |
| JP | 10-191984 A | 7/1998 |
| JP | 2000-228990 A | 8/2000 |
| JP | 2005-525100 A | 8/2005 |
| JP | 2006-506086 A | 2/2006 |
| WO | WO-92/04381 A1 | 3/1992 |
| WO | WO-97/27485 A1 | 7/1997 |
| WO | WO-01/20331 A1 | 3/2001 |
| WO | WO 02/092768 A2 | 11/2002 |
| WO | WO-03/039485 A2 | 5/2003 |
| WO | WO-2005/076015 A1 | 8/2005 |
| WO | WO-2006/006693 A1 | 1/2006 |
| WO | WO-2006/119115 A2 | 11/2006 |
| WO | WO-2007/056507 A1 | 5/2007 |
| WO | WO-2007/119774 A1 | 10/2007 |
| WO | WO-2008/114673 A1 | 9/2008 |
| WO | WO-2009/020144 A1 | 2/2009 |
| WO | WO-2009/051109 A1 | 4/2009 |
| WO | WO-2009/054433 A1 | 4/2009 |

OTHER PUBLICATIONS

Kennell, "Principles and Practices of Nucleic Acid Hybridization", Progr. Nucleic Acid Res. Mol. Biol. 11: 259-270, 1971.*
Ngo, in "The Protein Folding Problem and Tertiary Structure Prediction", Merz et al. (eds.), Birkhauser Boston: Boston, MA, pp. 433 and 492-495, 1994.*
Rudinger, in "Peptide Hormones", Parsons (ed.), University Park Press: Baltimore, MD, pp. 1-7, 1976.*
Ito, T. et al., "Expression of taurine transporter is regulated through the TonE/TonEBP pathway and contributes to cytoprotein in HepG2 cells", 2004, Biochem. J. vol. 382: pp. 177-182.*
Kim N. et al., "Response of Chinese hamster ovary cells to hyperosmotic pressure: effect of Bcl-2 overexpression", 2002, J. Biotech., vol. 95: pp. 237-248.*
Ramamoorthy, S. et al. "Functional characterization and chromosomal location of a cloned taurine transporter from human placecnta", 1994, Biochem. J., vol. 30: pp. 893-900.*
Jhiang et al., "Cloning of the human taurine transporter and characterization of taurine uptake in thyroid cells," FEBS, 318(2):139-144.
Supplementary European Search Report dated Aug. 3, 2010, in corresponding EP 08792251.4, 10 pages.
Bell et al., "Genetic Engineering of Hybridoma Glutamine Metabolism," Enzyme and Microbial Technology, 1995, 17(2):98-106.

(Continued)

Primary Examiner — Michael Burkhart
(74) Attorney, Agent, or Firm — Foley & Lardner LLP

(57) ABSTRACT

The present invention provides a method capable of producing a natural or recombinant protein in high yield.
The present invention relates to a method of producing a polypeptide, comprising culturing a cell which strongly expresses alanine aminotransferase and has a transferred DNA encoding a desired polypeptide and thereby allowing the cell to produce the polypeptide.

7 Claims, 13 Drawing Sheets

(56) References Cited

OTHER PUBLICATIONS

Butler, Michael, "Animal cell cultures: recent achievements and perspectives in the production of biopharmaceuticals," Appl. Microbiol. Biotechnol., Aug. 2005, 68(3):283-291.

Christie et al., "The Adaptation of BHK Cells to a Non-Ammoniagenic Glutamate-Based Culture Medium," Biotechnology and Bioengineering, Aug. 5, 1999, 64(3):298-309.

de la Cruz Edmonds et al., "Development of Transfection and High-Producer Screening Protocols for the CHOK1SV Cell System," Molecular Biology, Oct. 1, 2006, 34(2):179-190.

Good et al., "Engineering nitrogen use efficiency with alanine aminotransferase," Canadian Journal of Botany, Mar. 1, 2007, 85(3):252-262.

Kalwy et al., "Toward More Efficient Protein Expression," Molecular Biology, Oct. 2006, 34(2):151-156.

Voss et al., "Regulation of the expression and subcellular localization of the taurine transporter TauT in mouse NIH3T3 fibroblasts," Eur. J. Biochem., Dec. 2004, 271(23-24):4646-4658.

Yang et al., "cDNA Cloning, Genomic Structure, Chromosomal Mapping, and Functional Expression of a Novel Human Alanine Aminotransferase," Genomics, Mar. 1, 2002, 79(3):445-450.

Zhang et al., "Metabolic characteristics of recombinant chinese hamster ovary cells expressing glutamine synthetase in presence and absence of glutamine," Cytotechnology, 2006, 51(1):21-28.

U.S. Appl. No. 13/368,945, filed Feb. 8, 2012, Tabuchi et al.

Alper, Seth L., "Molecular physiology of SLC4 anion exchangers," Exp. Physiol., 2006, 91:153-161.

Arden et al., "Life and death in mammalian cell culture: strategies for apoptosis inhibition," Trends in Biotechnology, Apr. 2004, 22(4):174-180.

Butler, Michael, "Animal cell cultures: recent achievements and perspectives in the production of biopharmaceuticals," Appl. Microbiol. Biotechnol., 2005, 68:283-291.

Chambard et al., "Sugar transport by mammalian members of the SLC26 superfamily of anion-bicarbonate exchangers," J. Physiol., 2003, 550:667-677.

Christensen et al., "High expression of the taurine transporter TauT in primary cilic of NIH3T3 fibroblasts," Cell Biology International, 2005, 29:347-351.

Database DDBJ/EMBL/GenBank [online], Accession No. NM_000342, uploaded Sep. 25, 2007, Keskanokwong et al., Definition: *Homo sapiens* solute carrier family 4, anion exchanger, member 1 (erythrocyte membrane protein band 3, Diego blood group) (SLC4A1), mRNA, retrieved Nov. 11, 2008, 12 pages.

Database EMBL [Online] Jul. 23, 1992, XP002593029, retrieved from EBI accession No. EMBL:M95495, 3 pages.

Database Uniprot [Online] Jan. 10, 2006, XP002593032, retrieved from EBI accession No. UNIPROT:Q2VRP7, 1 page.

Database UniProt [Online] Jul. 1, 1993, XP002593028, retrieved from EBI accession No. UNIPROT:Q00589, 2 pages.

Database UniProt [Online] Jun. 1, 2001, "RecName: Full=Cysteine sulfinic acid decarboxylase; EC=4.1.1.29; AltName: Full=Cysteinesulfinate decarboxylase; AltName: Full=Sulfinoalanine decarboxylase;" XP002597738 retrieved from EBI accession No. UNIPROT:Q9DBE0 Database accession No. Q9DBE0, 2 pages.

Database Uniprot [Online] Mar. 15, 2005, XP002593030, retrieved from EBI accession No. UNIPROT:Q5F431, 1 page.

Database Uniprot [Online] Oct. 1, 2000, XP002593031, retrieved from EBI accession No. UNIPROT:Q9MZ34, 2 pages.

de la Rosa et al., "Evidence for a Rate-Limiting Role of Cysteinesulfinate Decarboxylase Activity in Taurine Biosynthesis in Vivo," Comp. Biochem. Physiol., 1985, 81B(3):565-571.

De La Rosa et al., "Evidence for a Rate-Limiting Role of Cysteinesulfinate Decarboxylase Activity in Taurine Biosynthesis In Vivo," Comp. Biochem. Physiol. B, 1985, 81(3):565-571.

Dusch et al., "Expression of the *Corynebacterium glutamicum panD* Gene Encoding L-Aspartate-alpha-Decarboxylase Leads to Pantothenate Overproduction in *Escherichia coli*," Applied and Environmental Microbiology, Apr. 1999, 65(4):1530-1539.

Final Office Action dated Dec. 17, 2010 in U.S. Appl. No. 12/226,195.

Final Office Action dated Mar. 2, 2012 in U.S. Appl. No. 12/734,283.

Final Office Action dated Aug. 23, 2011 in U.S. Appl. No. 12/733,815.

Fu et al., "Direct interaction and cooperative role of tumor suppressor p16 with band 3 (AE1)," FEBS Letters, 2005, 579(10):2105-2110.

Ganapathy et al., "Expression and Regulation of the Taurine Transporter in Cultured Cell Lines of Human Origin," Advances in Experimental Medicine and Biology, 1994, 359:51-57, XP009123192.

GenBank Accession No. AEQ38544, Oct. 2011, 2 pages.

GenBank Accession No. EGW01898, Aug. 2011, 2 pages.

Griffith, Owen W., "Crysteinesulfinate Metabolism, Altered Partitioning Between Transamination and Decarboxylation Following Administration of β-Methyleneaspartate," J. Biol. Chem., Feb. 10, 1983, 258(3):1591-1598.

Hammer et al., "β-Alanine but not taurine can function as an organic osmolyte in preimplantation mouse embryos cultured from fertilized eggs," Molecular Reproduction and Development, Oct. 2003, 66(2):153-161.

Han et al., "Is TauT an Anti-Apoptotic Gene?" Taurine 6, Oja et al. Eds., 2006, 59-67.

Hwang et al., "Expression and purification of recombinant human angiopoietin-2 produced in Chinese hamster ovary cells," Protein Expression and Purification, 2005, 39:175-183.

Ifandi et at., "Regulation of Cell Proliferation and Apoptosis in CHO-K1 Cells by the Coexpression of c-Myc and Bcl-2," Biotechnol. Prog., 2005, 21:671-677.

Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.

Kondo et al., "Modulation of apoptosis by endogenous Bcl-xL expression in MKN-45 human gastric cancer cells," Oncogene, 1998, 17:2585-2591.

Lee et al., "Development of Apoptosis-Resistant Dihydrofolate Reductase-Deficient Chinese Hamster Ovary Cell Line," Biotechnol. Bioengineer., 2003, 82:872-876.

Liu et al., "Cloning and expression of a cDNA encoding the transporter of taurine and β-alanine in mouse brain," Proc. Natl. Acad. Sci. USA, Dec. 1992, 89(24):12145-12149.

Lux et al., "Cloning and characterization of band 3, the human erythrocyte anion-exchange protein (AE1)," Proc. Natl. Acad. Sci. USA, Dec. 1989, 86:9089-9093.

Miyasaka et al., "Characterization of Human Taurine Transporter Expressed in Insect Cells Using a Recombinant Baculovirus," Protein Expression and Purification, 2001, 23(3):389-397.

Morgan et al., "Interactions of transmembrane carbonic anhydrase, CAIX, with bicarbonate transporters," Am. J. Physiol. Cell Physiol., Aug. 2007, 293(2):C738-C748.

Office Action dated Jan. 6, 2011 in U.S. Appl. No. 12/733,815.

Office Action dated May 18, 2010 in U.S. Appl. No. 12/226,195.

Office Action dated Aug. 3, 2011 in U.S. Appl. No. 12/734,283.

Office Action dated Aug. 9, 2011 in U.S. Appl. No. 12/450,161.

Porter et al., "Non-steady-state kinetics of brain glutamate decarboxylase resulting from interconversion of the apo- and holoenzyme," Biochimica et Biophysica Acta, 1988, 874:235-244.

Reymond et al., "Molecular cloning and sequence analysis of the cDNA encoding rat liver cysteine sulfinate decarboxylase (CSD)," Biochimica et Biophysica Acta, 1996, 1307:152-156.

Shen et al., "Expression of Anion Exchanger 1 Sequestrates p16 in the Cytoplasm in Gastric and Colonic Adenocarcinoma," Neoplasia, Oct. 2007, 9(10):812-819.

Smith et al., "Cloning and Expression of a High Affinity Taurine Transporter from Rat Brain," Mol. Pharmacol., 1992, 42(4):563-569.

Tabuchi et al., "Overexpression of Taurine Transporter in Chinese Hamster Ovary cells Can Enhance Cell Viability and Product Yield, While Promoting Glutamine Consumption," Biotechnology and Bioengineering, 2010, 107(6):998-1003.

Tang et al., "Protein Phosphorylation and Taurine Biosynthesis In Vivo and In Vitro," Journal of Neuroscience, Sep. 15, 1997, 17(18):6947-6951.

(56) References Cited

OTHER PUBLICATIONS

Tappaz et al., "Characterization of the cDNA Coding for Rat Brain Cysteine Sulfinate Decarboxylase: Brain and Liver Enzymes are Identical Proteins Encoded by Two Distince mRNAs," J. Neurochem., 1999, 73(3):903-912.

Tinland et al., "*Agrobacterium tumefaciens* transfers single-stranded transferred DNA (T-DNA) into the plant cell nucleus," Proc. Natl. Acad. Sci. USA, Aug. 1994, 91:8000-8004.

Trill et al., "Production of monoclonal antibodies in COS and CHO cells," Current Opinion in Biotechnology, 1995, 6:553-560.

Uchida et al., "Molecular cloning of the cDNA for an MDCK cell Na+- and Cl--dependent taurine transporter that is regulated by hypertonicity," Proc. Natl. Acad. Sci. USA, Sep. 1992, 89:8230-8234.

Voss et al., "Regulation of the expression and subcellular localization of the taurine transporter TauT in mouse NIH3T3 fibroblasts," Eur. J. Biochem., 2004, 271:4646-4658.

Wirth et al., "Isolation of overproducing recombinant mammalian cell lines by a fast and simple selection procedure," Gene, 1988, 73:419-426.

Wu et al., "Overexpression of Anion Exchanger 2 in Human Hepatocellular Carcinoma," Chinese Journal of Physiology, 2006, 49(4):192-198.

Yang et al., "Human Hepatitis B Viral e Antigen Interacts with Cellular Interleukin-1 Receptor Accessory Protein and Triggers Interleukin-1 Response," Journal of Biological Chemistry, Nov. 10, 2006, 281(45):34525-34536.

Office Action dated Sep. 21, 2012 in U.S. Appl. No. 13/368,945.

Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.

Office Action dated Feb. 27, 2013 in U.S. Appl. No. 13/138,909.

Final Office Action dated May 24, 2013 in U.S. Appl. No. 13/368,945.

Tanner et al., "The complete amino acid sequence of the human erythrocyte membrane anion-transport protein deduced from the cDNA sequence," Biochem. J., 1988, 256:703-712.

Beckmann et al., "Coexpression of band 3 mutants and Rh polypeptides: differential effects of band 3 on the expression of the Rh complex containing D polypeptide and the Rh complex containing CcEe polypeptide," Blood, Apr. 15, 2001, 97(8):2496-2505.

Han et al., "Regulation of TauT by cisplatin in LLC-PK1 renal cells," Pediatr. Nephrol., 2005, 20:1067-1072.

Ishiguro et al., "$CO_2$ permeability and bicarbonate transport in microperfused interlobular ducts isolated from guinea-pig pancreas," Journal of Physiology, 2000, 528.2:305-315.

Mount et al., "The SLC26 gene family of multifunctional anion exchangers," Pflugers Arch.—Eur. J. Physiol., 2004, 447:710-721.

Pushkin et al., "SLC4 base ($HCO_3^-$, $CO_3^{2-}$) transporters: classification, function, structure, genetic diseases, and knockout models," Am. J. Physiol. Renal Physiol., 2006, 290:F580-F599.

International Search Report mailed Sep. 2, 2008, in PCT/JP2008/064095, 5 pages.

Jhiang et al., "Cloning of the human taurine transporter and characterization of taurine uptake in thyroid cells," FEBS, 318(2):139-144, 1993.

\* cited by examiner

Fig. 8

Mean Viable Cell Density
( n=7 )

pHyg/TauT
( 9.28±3.27 )
x $10^5$ cells/ml
pHyg
( 5.69±2.09 )
x $10^5$ cells/ml t Test $P < 0.05$ Mean Lactate Concentration
( n=7 )

pHyg/TauT
( 1.54±0.20 ) g/L pHyg
( 1.75±0.15 ) g/L t Test  P <0.05

Mean Antibody Yield
( n=7 )

pHyg/TauT
( 397±69 ) mg/L pHyg
( 342±55 ) mg/L

SEQUENCE LISTING

<160> NUMBER OF SEQ ID NOS: 68

<210> SEQ ID NO 1
<211> LENGTH: 1491
<212> TYPE: DNA
<213> ORGANISM: Homo sapiens

<400> SEQUENCE: 1

```
atggcctcga gcacaggtga ccggagccag gcggtgaggc atggactgag ggcgaaggtg      60
ctgacgctgg acggcatgaa cccgcgtgtg cggagagtgg agtacgcagt gcgtggcccc     120
atagtgcagc gagccttgga gctggagcag gagctgcgcc agggtgtgaa gaagcctttc     180
accgaggtca tccgtgccaa catcggggac gcacaggcta tggggcagag gcccatcacc     240
ttcctgcgcc aggtcttggc cctctgtgtt aaccctgatc ttctgagcag ccccaacttc     300
cctgacgatg ccaagaaaag gcggagcgc atcttgcagg cgtgtggggg ccacagtctg      360
ggggcctaca gcgtcagctc cggcatccag ctgatccggg aggacgtggc gcggtacatt     420
gagaggcgtg acgaggcat ccctgcggac cccaacaacg tcttcctgtc cacaggggcc      480
agcgatgcca tcgtgacggt gctgaagctg ctggtggccg gcgagggcca cacacgcacg     540
ggtgtgctca tccccatccc ccagtaccca ctctactcgg ccacgctggc agagctgggc     600
gcagtgcagg tggattacta cctggacgag gagcgtgcct gggcgctgga cgtggccgag     660
cttcaccgtg cactgggcca ggcgcgtgac cactgccgcc tcgtgcgct ctgtgtcatc      720
aaccctggca ccccaccgg gcaggtgcag acccgcgagt gcatcgaggc cgtgatccgc      780
ttcgcctcg aagagcggct ctttctgctg gcggacgagg tgtaccagga caacgtgtac      840
gccgcgggtt cgcagttcca ctcattcaag aaggtgctca tggagatggg gccgccctac     900
gccgggcagc aggagcttgc ctccttccac tccacctcca agggctacat gggcgagtgc     960
gggttccgcg gcggctatgt ggaggtggtg aacatggacg ctgcagtgca gcagcagatg    1020
ctgaagctga tgagtgtgcg gctgtgcccg ccggtgccag acaggccct gctggacctg     1080
gtggtcagcc cgcccgcgcc caccgacccc tcctttgcgc agttccaggc tgagaagcag    1140
gcagtgctgg cagagctggc ggccaaggcc aagctcaccg agcaggtctt caatgaggct    1200
cctggcatca gctgcaaccc agtgcagggc gccatgtact ccttcccgcg cgtgcagctg    1260
ccccgcgggg cggtggagcg cgctcaggag ctgggcctgg ccccgatat gttcttctgc    1320
ctgcgcctcc tggaggagac cggcatctgc gtggtgccag ggagcggctt tgggcagcgg    1380
gaaggcacct accacttccg gatgaccatt ctgcccccct ggagaaact gcggctgctg    1440
ctggagaagc tgagcaggtt ccatgccaag ttcaccctcg agtactcctg a             1491
```

<210> SEQ ID NO 2
<211> LENGTH: 496
<212> TYPE: PRT
<213> ORGANISM: Homo sapiens

<400> SEQUENCE: 2

Met Ala Ser Ser Thr Gly Asp Arg Ser Gln Ala Val Arg His Gly Leu
1               5                   10                  15

Arg Ala Lys Val Leu Thr Leu Asp Gly Met Asn Pro Arg Val Arg Arg
                20                  25                  30

Val Glu Tyr Ala Val Arg Gly Pro Ile Val Gln Arg Ala Leu Glu Leu
            35                  40                  45

Glu Gln Glu Leu Arg Gln Gly Val Lys Lys Pro Phe Thr Glu Val Ile

```
                50                  55                  60
Arg Ala Asn Ile Gly Asp Ala Gln Ala Met Gly Gln Arg Pro Ile Thr
 65                  70                  75                  80

Phe Leu Arg Gln Val Leu Ala Leu Cys Val Asn Pro Asp Leu Leu Ser
                     85                  90                  95

Ser Pro Asn Phe Pro Asp Asp Ala Lys Lys Arg Ala Glu Arg Ile Leu
                    100                 105                 110

Gln Ala Cys Gly Gly His Ser Leu Gly Ala Tyr Ser Val Ser Ser Gly
                    115                 120                 125

Ile Gln Leu Ile Arg Glu Asp Val Ala Arg Tyr Ile Glu Arg Arg Asp
            130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                165                 170                 175

His Thr Arg Thr Gly Val Leu Ile Pro Ile Pro Gln Tyr Pro Leu Tyr
                180                 185                 190

Ser Ala Thr Leu Ala Glu Leu Gly Ala Val Gln Val Asp Tyr Tyr Leu
                195                 200                 205

Asp Glu Glu Arg Ala Trp Ala Leu Asp Val Ala Glu Leu His Arg Ala
210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
                260                 265                 270

Glu Val Tyr Gln Asp Asn Val Tyr Ala Ala Gly Ser Gln Phe His Ser
                275                 280                 285

Phe Lys Lys Val Leu Met Glu Met Gly Pro Pro Tyr Ala Gly Gln Gln
290                 295                 300

Glu Leu Ala Ser Phe His Ser Thr Ser Lys Gly Tyr Met Gly Glu Cys
305                 310                 315                 320

Gly Phe Arg Gly Gly Tyr Val Glu Val Val Asn Met Asp Ala Ala Val
                325                 330                 335

Gln Gln Gln Met Leu Lys Leu Met Ser Val Arg Leu Cys Pro Pro Val
                340                 345                 350

Pro Gly Gln Ala Leu Leu Asp Leu Val Val Ser Pro Pro Ala Pro Thr
                355                 360                 365

Asp Pro Ser Phe Ala Gln Phe Gln Ala Glu Lys Gln Ala Val Leu Ala
370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
                405                 410                 415

Arg Val Gln Leu Pro Pro Arg Ala Val Glu Arg Ala Gln Glu Leu Gly
                420                 425                 430

Leu Ala Pro Asp Met Phe Phe Cys Leu Arg Leu Leu Glu Glu Thr Gly
                435                 440                 445

Ile Cys Val Val Pro Gly Ser Gly Phe Gly Gln Arg Glu Gly Thr Tyr
                450                 455                 460

His Phe Arg Met Thr Ile Leu Pro Pro Leu Glu Lys Leu Arg Leu Leu
465                 470                 475                 480
```

Leu Glu Lys Leu Ser Arg Phe His Ala Lys Phe Thr Leu Glu Tyr Ser
            485                 490                 495

<210> SEQ ID NO 3
<211> LENGTH: 1572
<212> TYPE: DNA
<213> ORGANISM: Homo sapiens

<400> SEQUENCE: 3

| | |
|---|---|
| atgcagcggg cggcggcgct ggtccggcgg ggctgtggtc cccggacccc cagctcctgg | 60 |
| ggccgcagcc agagcagcgc ggccgccgag gcctcggcgg tgctcaaggt gcggcccgag | 120 |
| cgcagccggc gcgagcgcat cctcacgctg gagtccatga cccgcaggt gaaggcggtg | 180 |
| gagtacgccg tgcggggacc catcgtgctc aaggccggcg agatcgagct cgagctgcag | 240 |
| cggggtatca aaaagccatt cacagaggtc atccgagcca catcgggga cgcccaggct | 300 |
| atggggcagc agccaatcac cttcctccgg caggtgatgg cactatgcac ctacccaaac | 360 |
| ctgctggaca gccccagctt cccagaagat gctaagaaac gtgcccggcg gatcctgcag | 420 |
| gcttgtggcg ggaacagcct ggggtcctac agtgctagcc agggtgtcaa ctgcatccgt | 480 |
| gaagatgtgg ctgcctacat caccaggagg gatggcggtg tgcctgcgga ccccgacaac | 540 |
| atctacctga ccacgggagc tagtgacggc atttctacga tcctgaagat cctcgtctcc | 600 |
| ggggcggca agtcacggac aggtgtgatg atccccatcc cacaatatcc cctctattca | 660 |
| gctgtcatct ctgagctcga cgccatccag gtgaattact acctggacga ggagaactgc | 720 |
| tgggcgctga atgtgaatga ctccggcgg gcggtgcagg aggccaaaga ccactgtgat | 780 |
| cctaaggtgc tctgcataat caaccctggg aaccccacag gccaggtaca aagcagaaag | 840 |
| tgcatagaag atgtgatcca ctttgcctgg aagagaagc tctttctcct ggctgatgag | 900 |
| gtgtaccagg acaacgtgta ctctccagat tgcagattcc actccttcaa gaaggtgctg | 960 |
| tacgagatgg gcccgagta ctccagcaac gtggagctcg cctccttcca ctccacctcc | 1020 |
| aagggctaca tgggcgagtg tggttacaga ggaggctaca tggaggtgat caacctgcac | 1080 |
| cctgagatca agggccagct ggtgaagctg ctgtcggtgc gctgtgccc ccagtgtct | 1140 |
| gggcaggccg ccatggacat tgtcgtgaac ccccggtgg caggagagga gtcctttgag | 1200 |
| caattcagcc gagagaagga gtcggtcctg ggtaatctgg ccaaaaaagc aaagctgacg | 1260 |
| gaagacctgt ttaaccaagt cccaggaatt cactgcaacc ccttgcaggg ggccatgtac | 1320 |
| gccttccctc ggatcttcat tcctgccaaa gctgtggagg ctgctcaggc ccatcaaatg | 1380 |
| gctccagaca tgttctactg catgaagctc ctggaggaga ctggcatctg tgtcgtgccc | 1440 |
| ggcagtggct ttgggcagag ggaaggcact taccacttca ggatgactat cctccctcca | 1500 |
| gtggagaagc tgaaaacggt gctgcagaag gtgaaagact ccacatcaa cttcctggag | 1560 |
| aagtacgcgt ga | 1572 |

<210> SEQ ID NO 4
<211> LENGTH: 523
<212> TYPE: PRT
<213> ORGANISM: Homo sapiens

<400> SEQUENCE: 4

Met Gln Arg Ala Ala Ala Leu Val Arg Arg Gly Cys Gly Pro Arg Thr
1               5                   10                  15

Pro Ser Ser Trp Gly Arg Ser Gln Ser Ser Ala Ala Glu Ala Ser
            20                  25                  30

Ala Val Leu Lys Val Arg Pro Glu Arg Ser Arg Arg Glu Arg Ile Leu

```
            35                  40                  45
Thr Leu Glu Ser Met Asn Pro Gln Val Lys Ala Val Glu Tyr Ala Val
 50                  55                  60

Arg Gly Pro Ile Val Leu Lys Ala Gly Glu Ile Glu Leu Glu Leu Gln
 65                  70                  75                  80

Arg Gly Ile Lys Lys Pro Phe Thr Glu Val Ile Arg Ala Asn Ile Gly
                 85                  90                  95

Asp Ala Gln Ala Met Gly Gln Gln Pro Ile Thr Phe Leu Arg Gln Val
            100                 105                 110

Met Ala Leu Cys Thr Tyr Pro Asn Leu Leu Asp Ser Pro Ser Phe Pro
            115                 120                 125

Glu Asp Ala Lys Lys Arg Ala Arg Ile Leu Gln Ala Cys Gly Gly
            130                 135                 140

Asn Ser Leu Gly Ser Tyr Ser Ala Ser Gln Gly Val Asn Cys Ile Arg
145                 150                 155                 160

Glu Asp Val Ala Ala Tyr Ile Thr Arg Arg Asp Gly Val Pro Ala
                165                 170                 175

Asp Pro Asp Asn Ile Tyr Leu Thr Thr Gly Ala Ser Asp Gly Ile Ser
            180                 185                 190

Thr Ile Leu Lys Ile Leu Val Ser Gly Gly Lys Ser Arg Thr Gly
            195                 200                 205

Val Met Ile Pro Ile Pro Gln Tyr Pro Leu Tyr Ser Ala Val Ile Ser
            210                 215                 220

Glu Leu Asp Ala Ile Gln Val Asn Tyr Leu Asp Glu Glu Asn Cys
225                 230                 235                 240

Trp Ala Leu Asn Val Asn Glu Leu Arg Arg Ala Val Gln Glu Ala Lys
                245                 250                 255

Asp His Cys Asp Pro Lys Val Leu Cys Ile Ile Asn Pro Gly Asn Pro
            260                 265                 270

Thr Gly Gln Val Gln Ser Arg Lys Cys Ile Glu Asp Val Ile His Phe
            275                 280                 285

Ala Trp Glu Glu Lys Leu Phe Leu Leu Ala Asp Glu Val Tyr Gln Asp
            290                 295                 300

Asn Val Tyr Ser Pro Asp Cys Arg Phe His Ser Phe Lys Lys Val Leu
305                 310                 315                 320

Tyr Glu Met Gly Pro Glu Tyr Ser Ser Asn Val Glu Leu Ala Ser Phe
                325                 330                 335

His Ser Thr Ser Lys Gly Tyr Met Gly Glu Cys Gly Tyr Arg Gly Gly
            340                 345                 350

Tyr Met Glu Val Ile Asn Leu His Pro Glu Ile Lys Gly Gln Leu Val
            355                 360                 365

Lys Leu Leu Ser Val Arg Leu Cys Pro Pro Val Ser Gly Gln Ala Ala
            370                 375                 380

Met Asp Ile Val Val Asn Pro Pro Val Ala Gly Glu Glu Ser Phe Glu
385                 390                 395                 400

Gln Phe Ser Arg Glu Lys Glu Ser Val Leu Gly Asn Leu Ala Lys Lys
                405                 410                 415

Ala Lys Leu Thr Glu Asp Leu Phe Asn Gln Val Pro Gly Ile His Cys
            420                 425                 430

Asn Pro Leu Gln Gly Ala Met Tyr Ala Phe Pro Arg Ile Phe Ile Pro
            435                 440                 445

Ala Lys Ala Val Glu Ala Ala Gln Ala His Gln Met Ala Pro Asp Met
            450                 455                 460
```

Phe Tyr Cys Met Lys Leu Leu Glu Glu Thr Gly Ile Cys Val Val Pro
465                 470                 475                 480

Gly Ser Gly Phe Gly Gln Arg Glu Gly Thr Tyr His Phe Arg Met Thr
                485                 490                 495

Ile Leu Pro Pro Val Glu Lys Leu Lys Thr Val Leu Gln Lys Val Lys
            500                 505                 510

Asp Phe His Ile Asn Phe Leu Glu Lys Tyr Ala
        515                 520

<210> SEQ ID NO 5
<211> LENGTH: 1491
<212> TYPE: DNA
<213> ORGANISM: Mus musculus

<400> SEQUENCE: 5

```
atggcctcac aaaggaatga ccggatccag gcttcaagga atggactgaa ggggaaggtg      60
ctaactctgg ataccatgaa cccatgtgtg cggagggtgg agtatgcagt ccgaggcccc     120
atcgtgcaac gtgccttgga gctggagcag gagctgcgcc agggtgtgaa gaagcctttt     180
actgaggtta tccgtgccaa tattggggat gcacaagcca tggggcagag acccatcacc     240
ttcttccgcc aggtcctggc cctctgtgtc taccccaatc ttctgagcag tccggacttc     300
ccagaggatg ccaagagaag gcagaacgc atcttgcagg catgcggggg ccacagcctg      360
ggtgcctata gcattagctc tggaatccag ccgattcggg aggatgtggc gcaatatatt     420
gagaggagag acgaggcat ccctgcagac ccgaacaaca tatttctgtc cacaggggcc      480
agcgatgcca tcgtgaccat gctcaagctg ctggtagccg gcgagggccg tgcgcgaacc     540
ggtgtactca ttcccattcc tcagtaccca ctgtactcag ctgcgctggc tgagctggac     600
gccgtgcaag tggactacta cctggacgaa gagcgcgcct gggctcttga catcgctgag     660
ctgcggcgcg ctctgtgcca ggcacgtgac cgctgctgcc ctcgagtact atgcgtcatc     720
aaccccggca accccacggg gcaggtgcag acccgtgaat gcatcgaggc cgtaatccgc     780
tttgctttcg aagagggact cttcctgatg gctgatgagg tataccaaga caatgtatat     840
gccgagggct ctcagttcca ttcattcaag aaggtgctca cggagatggg gccaccatat     900
gccacgcagc aggagctcgc gtcttttcac tcagtctcta agggctacat gggcgagtgc     960
gggtttcgtg gtggctatgt ggaagtggta aacatggatg ccgaggtgca gaaacagatg    1020
gcgaaactga tgagcgtgcg gttgtgtcca ccagtgccgg ccaggctttt gatgggcatg    1080
gtggtcagtc cgccaacccc ctcggagccg tccttcaagc agtttcaagc agagaggcag    1140
gaggtgctgg ctgaactggc agccaaggct aaactcacgg agcaggtctt caacgaggcc    1200
cccgggatcc gctgcaaccc ggtgcagggc gctatgtatt ccttccctca aattcagctg    1260
cctttgaaag cagtgcagcg tgcgcaggac ctgggcctgg cccctgacat gttcttctgt    1320
ctgtgcctcc tggaagagac tggcatctgc gttgtgcctg ggagtggctt tgggcagcag    1380
gagggcacct atcatttccg gatgaccatt ctgccccca tggagaaact gcgggtgctg    1440
ctggagaaac tgaggcactt ccatgctaaa ttcactcatg agtactcctg a             1491
```

<210> SEQ ID NO 6
<211> LENGTH: 496
<212> TYPE: PRT
<213> ORGANISM: Mus musculus

<400> SEQUENCE: 6

Met Ala Ser Gln Arg Asn Asp Arg Ile Gln Ala Ser Arg Asn Gly Leu
1               5                   10                  15

```
Lys Gly Lys Val Leu Thr Leu Asp Thr Met Asn Pro Cys Val Arg Arg
             20                  25                  30

Val Glu Tyr Ala Val Arg Gly Pro Ile Val Gln Arg Ala Leu Glu Leu
             35                  40                  45

Glu Gln Glu Leu Arg Gln Gly Val Lys Lys Pro Phe Thr Glu Val Ile
         50                  55                  60

Arg Ala Asn Ile Gly Asp Ala Gln Ala Met Gly Gln Arg Pro Ile Thr
 65              70                  75                  80

Phe Phe Arg Gln Val Leu Ala Leu Cys Val Tyr Pro Asn Leu Leu Ser
             85                  90                  95

Ser Pro Asp Phe Pro Glu Asp Ala Lys Arg Arg Ala Glu Arg Ile Leu
             100                 105                 110

Gln Ala Cys Gly Gly His Ser Leu Gly Ala Tyr Ser Ile Ser Ser Gly
             115                 120                 125

Ile Gln Pro Ile Arg Glu Asp Val Ala Gln Tyr Ile Glu Arg Arg Asp
             130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ala Gly Glu Gly
                 165                 170                 175

Arg Ala Arg Thr Gly Val Leu Ile Pro Ile Pro Gln Tyr Pro Leu Tyr
             180                 185                 190

Ser Ala Ala Leu Ala Glu Leu Asp Ala Val Gln Val Asp Tyr Tyr Leu
             195                 200                 205

Asp Glu Glu Arg Ala Trp Ala Leu Asp Ile Ala Glu Leu Arg Arg Ala
             210                 215                 220

Leu Cys Gln Ala Arg Asp Arg Cys Cys Pro Arg Val Leu Cys Val Ile
225                 230                 235                 240

Asn Pro Gly Asn Pro Thr Gly Gln Val Gln Thr Arg Glu Cys Ile Glu
             245                 250                 255

Ala Val Ile Arg Phe Ala Phe Glu Glu Gly Leu Phe Leu Met Ala Asp
             260                 265                 270

Glu Val Tyr Gln Asp Asn Val Tyr Ala Glu Gly Ser Gln Phe His Ser
             275                 280                 285

Phe Lys Lys Val Leu Thr Glu Met Gly Pro Pro Tyr Ala Thr Gln Gln
290                 295                 300

Glu Leu Ala Ser Phe His Ser Val Ser Lys Gly Tyr Met Gly Glu Cys
305                 310                 315                 320

Gly Phe Arg Gly Gly Tyr Val Glu Val Val Asn Met Asp Ala Glu Val
             325                 330                 335

Gln Lys Gln Met Ala Lys Leu Met Ser Val Arg Leu Cys Pro Pro Val
             340                 345                 350

Pro Gly Gln Ala Leu Met Gly Met Val Val Ser Pro Pro Thr Pro Ser
             355                 360                 365

Glu Pro Ser Phe Lys Gln Phe Gln Ala Glu Arg Gln Glu Val Leu Ala
             370                 375                 380

Glu Leu Ala Ala Lys Ala Lys Leu Thr Glu Gln Val Phe Asn Glu Ala
385                 390                 395                 400

Pro Gly Ile Arg Cys Asn Pro Val Gln Gly Ala Met Tyr Ser Phe Pro
             405                 410                 415

Gln Ile Gln Leu Pro Leu Lys Ala Val Gln Arg Ala Gln Asp Leu Gly
             420                 425                 430

Leu Ala Pro Asp Met Phe Phe Cys Leu Cys Leu Leu Glu Glu Thr Gly
```

```
                435                 440                 445
Ile Cys Val Val Pro Gly Ser Gly Phe Gly Gln Gln Glu Gly Thr Tyr
                450                 455                 460

His Phe Arg Met Thr Ile Leu Pro Pro Met Glu Lys Leu Arg Val Leu
465                 470                 475                 480

Leu Glu Lys Leu Arg His Phe His Ala Lys Phe Thr His Glu Tyr Ser
                    485                 490                 495
```

<210> SEQ ID NO 7
<211> LENGTH: 1569
<212> TYPE: DNA
<213> ORGANISM: Mus musculus

<400> SEQUENCE: 7

| | |
|---|---|
| atgcagcggg cagcggtgct ggtgcggcgg ggctcctgcc cccgcgcctc gggcccctgg | 60 |
| ggccgtagtc acagcagcgc tgcagccgaa gcctcggcgg cgctcaaggt gcgaccggag | 120 |
| cgcagccctc gagaccgcat cctcaccctg gagtccatga cccgcaggt gaaggcggtg | 180 |
| gagtacgctg tgcggggacc catcgtgctc aaagccggcg agatcgagat ggagctgcag | 240 |
| cggggtatca aaaaccatt cactgaggta atccgagcca acattgggga tgcccatgct | 300 |
| atgggccagc agccaatcac cttcctccgt caggtgatgg cactctgcac ctacccaaac | 360 |
| ctactaaaca gccccagctt cccagaagac gctaagaaac gagcgcggcg gatcctgcag | 420 |
| gcttgtggtg aaacagctt gggatcttac agtgctagcc aaggcgttaa ctgtatccgt | 480 |
| gaagatgtgg cagcctttat caccaggaga tggtgtgc ctgcagaccc agacaacatt | 540 |
| tacctgacta ctggagctag cgacggtatt tctacaatcc tgaagctcct ggtctccggt | 600 |
| ggtggcaagt cacggaccgg cgtgatgatt cccatccccc agtatcccctt gtactccgcg | 660 |
| gtcatctctg agctcgacgc ggtgcaggtc aactactatc tggatgaaga aactgctgg | 720 |
| gctttgaatg tggacgagct ccggcgggca ttgcggcaag ccaaagacca ctgtgaccct | 780 |
| aaagttctct gcattatcaa ccccggaaac cccacaggcc aggtacaaag cagaaagtgc | 840 |
| atagaagatg tgattcactt tgcctgggaa gagaagcttt ttctcctggc tgatgaggtg | 900 |
| taccaggaca acgtgtactc tccagactgc agattccact cgtttaagaa agtgctttac | 960 |
| cagatggggc acgagtactc cagcaacgtg gagctcgcct ccttccactc cacctccaag | 1020 |
| ggctacatgg gcgagtgtgg ctacagaggg ggctacatgg aggtgatcaa tttgcacccc | 1080 |
| gagatcaaag gccagctggt gaagctactc tcggttcgcc tctgtccgcc agtgtcagga | 1140 |
| caggccgcca tggacattgt tgtgaatcca ccggaaccag gagaggagtc ctttgagcaa | 1200 |
| ttcagcaggg aaaaagaatt cgtccttggt aatctggcca aaaaagcaaa gctgacagaa | 1260 |
| gatctgttta ccaagtcccc agggatccag tgcaacccct gcaaggagc tatgtatgcg | 1320 |
| ttccctcgga ttctcatccc tgccaaggcc gtgaggcag ctcagtccca taaaatggct | 1380 |
| ccagacatgt tctactgcat gaagctcctg gaggagactg gcatctgtgt cgtgcctggc | 1440 |
| agtggctttg gcagcgaga aggcacttac cacttcagaa tgaccattct ccctccggtg | 1500 |
| gataaactga gaccgtgct ccacaaggtg aaagactttc acctgaagtt cctggagcag | 1560 |
| tactcatga | 1569 |

<210> SEQ ID NO 8
<211> LENGTH: 522
<212> TYPE: PRT
<213> ORGANISM: Mus musculus

<400> SEQUENCE: 8

-continued

```
Met Gln Arg Ala Ala Val Leu Val Arg Gly Ser Cys Pro Arg Ala
1               5                   10                  15

Ser Gly Pro Trp Gly Arg Ser His Ser Ser Ala Ala Glu Ala Ser
                20                  25                  30

Ala Ala Leu Lys Val Arg Pro Glu Arg Ser Pro Arg Asp Arg Ile Leu
            35                  40                  45

Thr Leu Glu Ser Met Asn Pro Gln Val Lys Ala Val Glu Tyr Ala Val
    50                  55                  60

Arg Gly Pro Ile Val Leu Lys Ala Gly Glu Ile Glu Met Glu Leu Gln
65                  70                  75                  80

Arg Gly Ile Lys Lys Pro Phe Thr Glu Val Ile Arg Ala Asn Ile Gly
                85                  90                  95

Asp Ala His Ala Met Gly Gln Gln Pro Ile Thr Phe Leu Arg Gln Val
            100                 105                 110

Met Ala Leu Cys Thr Tyr Pro Asn Leu Leu Asn Ser Pro Ser Phe Pro
            115                 120                 125

Glu Asp Ala Lys Lys Arg Ala Arg Arg Ile Leu Gln Ala Cys Gly Gly
            130                 135                 140

Asn Ser Leu Gly Ser Tyr Ser Ala Ser Gln Gly Val Asn Cys Ile Arg
145                 150                 155                 160

Glu Asp Val Ala Ala Phe Ile Thr Arg Arg Asp Gly Val Pro Ala Asp
                165                 170                 175

Pro Asp Asn Ile Tyr Leu Thr Thr Gly Ala Ser Asp Gly Ile Ser Thr
            180                 185                 190

Ile Leu Lys Leu Leu Val Ser Gly Gly Lys Ser Arg Thr Gly Val
            195                 200                 205

Met Ile Pro Ile Pro Gln Tyr Pro Leu Tyr Ser Ala Val Ile Ser Glu
210                 215                 220

Leu Asp Ala Val Gln Val Asn Tyr Tyr Leu Asp Glu Glu Asn Cys Trp
225                 230                 235                 240

Ala Leu Asn Val Asp Glu Leu Arg Arg Ala Leu Arg Gln Ala Lys Asp
                245                 250                 255

His Cys Asp Pro Lys Val Leu Cys Ile Ile Asn Pro Gly Asn Pro Thr
            260                 265                 270

Gly Gln Val Gln Ser Arg Lys Cys Ile Glu Asp Val Ile His Phe Ala
            275                 280                 285

Trp Glu Glu Lys Leu Phe Leu Leu Ala Asp Glu Val Tyr Gln Asp Asn
290                 295                 300

Val Tyr Ser Pro Asp Cys Arg Phe His Ser Phe Lys Lys Val Leu Tyr
305                 310                 315                 320

Gln Met Gly His Glu Tyr Ser Ser Asn Val Glu Leu Ala Ser Phe His
                325                 330                 335

Ser Thr Ser Lys Gly Tyr Met Gly Glu Cys Gly Tyr Arg Gly Gly Tyr
            340                 345                 350

Met Glu Val Ile Asn Leu His Pro Glu Ile Lys Gly Gln Leu Val Lys
            355                 360                 365

Leu Leu Ser Val Arg Leu Cys Pro Pro Val Ser Gly Gln Ala Ala Met
370                 375                 380

Asp Ile Val Val Asn Pro Pro Glu Pro Gly Glu Glu Ser Phe Glu Gln
385                 390                 395                 400

Phe Ser Arg Glu Lys Glu Phe Val Leu Gly Asn Leu Ala Lys Lys Ala
                405                 410                 415

Lys Leu Thr Glu Asp Leu Phe Asn Gln Val Pro Gly Ile Gln Cys Asn
```

```
                      420             425              430
Pro Leu Gln Gly Ala Met Tyr Ala Phe Pro Arg Ile Leu Ile Pro Ala
            435                 440                 445

Lys Ala Val Glu Ala Ala Gln Ser His Lys Met Ala Pro Asp Met Phe
        450                 455                 460

Tyr Cys Met Lys Leu Leu Glu Glu Thr Gly Ile Cys Val Val Pro Gly
465                 470                 475                 480

Ser Gly Phe Gly Gln Arg Glu Gly Thr Tyr His Phe Arg Met Thr Ile
                485                 490                 495

Leu Pro Pro Val Asp Lys Leu Lys Thr Val Leu His Lys Val Lys Asp
            500                 505                 510

Phe His Leu Lys Phe Leu Glu Gln Tyr Ser
        515                 520
```

<210> SEQ ID NO 9
<211> LENGTH: 1491
<212> TYPE: DNA
<213> ORGANISM: Rattus norvegicus

<400> SEQUENCE: 9

```
atggcctcac gggtgaatga tcaaagccag gcttcaagga atgggctgaa gggaaaggtg      60
ctaactctgg acactatgaa cccatgtgtg cggagggtgg agtatgcagt tcgaggaccc     120
attgtgcagc gtgccttgga gctggagcag gagctgcgtc agggtgtgaa gaagccgttt     180
actgaggtca tccgtgccaa cattggggat gcacaagcca tggggcagag acccatcacc     240
ttcttccgcc aggtcctggc cctctgtgtc taccccaatc ttctgagcag tcctgacttc     300
ccagaggatg ccaagagaag ggcagaacgc atcttgcagg cctgcggggg ccacagcctg     360
ggtgcctata gcattagctc tggaatccag ccgatccggg aggatgtggc gcaatacatt     420
gagagaagag acgaggcat ccccgcagac ccgaacaaca tatttctatc cacaggggcc     480
agcgatgcca tcgtgacaat gctcaagctg ctggtatctg gcgagggccg tgcacgaaca     540
ggtgtactca ttcccattcc tcagtaccca ctgtactcag ccgcgctggc tgaactggac     600
gccgtgcaag tggactacta cctggacgaa gagcgcgcct gggctctgga catcgcagag     660
ctgcggcgcg ctctgtgcca ggcacgtgac cgttgctgcc ctcgagtact gtgcgtcatc     720
aaccccggca accccactgg gcaggtgcag accgtgagt gcatcgaggc cgtaatccgc     780
tttgctttca agaaggact cttcttgatg gctgatgagg tataccagga caacgtgtat     840
gccgagggct ctcagttcca ttcattcaag aaggtgctca tggagatggg gccaccgtat     900
tccacgcagc aggagcttgc ttcttttcca tcagtctcta agggctacat gggcgagtgc     960
gggtttcgtg gtggctatgt ggaggtggta acatggatg ctgaggtgca gaaacagatg    1020
gggaagctga tgagtgtgcg gctgtgtcca ccagtgccag gccaggcctt gatggacatg    1080
gtggtcagtc cgccaacacc ctccgagccg tccttcaagc agtttcaagc agagagacag    1140
gaggtgctgg ctgaactggc agccaaggct aagctcacgg agcaggtctt caatgaggct    1200
cccgggatcc gctgcaaccc agtgcagggc gccatgtatt ccttccctca gtgcagctg    1260
cccttgaaag cggtgcagcg tgctcaggaa ctgggcctgg ccctgacat gttcttctgc    1320
ctgtgcctcc tggaagagac tggcatctgc gttgtgcccg ggagtggctt tgggcagcag    1380
gagggcacct atcatttccg gatgaccatt ctgccccca tggagaaact gcggctgctg    1440
ctggaaaaac tcagtcactt ccatgccaag ttcacccatg agtactcctg a             1491
```

<210> SEQ ID NO 10

<211> LENGTH: 496
<212> TYPE: PRT
<213> ORGANISM: Rattus norvegicus

<400> SEQUENCE: 10

```
Met Ala Ser Arg Val Asn Asp Gln Ser Gln Ala Ser Arg Asn Gly Leu
1               5                   10                  15

Lys Gly Lys Val Leu Thr Leu Asp Thr Met Asn Pro Cys Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Phe Arg Gln Val Leu Ala Leu Cys Val Tyr Pro Asn Leu Leu Ser
                85                  90                  95

Ser Pro Asp Phe Pro Glu Asp Ala Lys Arg Arg Ala Glu Arg Ile Leu
            100                 105                 110

Gln Ala Cys Gly Gly His Ser Leu Gly Ala Tyr Ser Ile Ser Ser Gly
        115                 120                 125

Ile Gln Pro Ile Arg Glu Asp Val Ala Gln Tyr Ile Glu Arg Arg Asp
    130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ser Gly Glu Gly
                165                 170                 175

Arg Ala Arg Thr Gly Val Leu Ile Pro Ile Pro Gln Tyr Pro Leu Tyr
            180                 185                 190

Ser Ala Ala Leu Ala Glu Leu Asp Ala Val Gln Val Asp Tyr Tyr Leu
        195                 200                 205

Asp Glu Glu Arg Ala Trp Ala Leu Asp Ile Ala Glu Leu Arg Arg Ala
    210                 215                 220

Leu Cys Gln Ala Arg Asp Arg Cys Cys Pro Arg Val Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Lys Glu Gly Leu Phe Leu Met Ala Asp
            260                 265                 270

Glu Val Tyr Gln Asp Asn Val Tyr Ala Glu Gly Ser Gln Phe His Ser
        275                 280                 285

Phe Lys Lys Val Leu Met Glu Met Gly Pro Pro Tyr Ser Thr Gln Gln
    290                 295                 300

Glu Leu Ala Ser Phe His Ser Val Ser Lys Gly Tyr Met Gly Glu Cys
305                 310                 315                 320

Gly Phe Arg Gly Gly Tyr Val Glu Val Val Asn Met Asp Ala Glu Val
                325                 330                 335

Gln Lys Gln Met Gly Lys Leu Met Ser Val Arg Leu Cys Pro Pro Val
            340                 345                 350

Pro Gly Gln Ala Leu Met Asp Met Val Val Ser Pro Thr Pro Ser
        355                 360                 365

Glu Pro Ser Phe Lys Gln Phe Gln Ala Glu Arg Gln Glu Val Leu Ala
    370                 375                 380

Glu Leu Ala Ala Lys Ala Lys Leu Thr Glu Gln Val Phe Asn Glu Ala
385                 390                 395                 400
```

```
Pro Gly Ile Arg Cys Asn Pro Val Gln Gly Ala Met Tyr Ser Phe Pro
            405                 410                 415

Gln Val Gln Leu Pro Leu Lys Ala Val Gln Arg Ala Gln Glu Leu Gly
        420                 425                 430

Leu Ala Pro Asp Met Phe Phe Cys Leu Cys Leu Leu Glu Glu Thr Gly
    435                 440                 445

Ile Cys Val Val Pro Gly Ser Gly Phe Gly Gln Gln Glu Gly Thr Tyr
450                 455                 460

His Phe Arg Met Thr Ile Leu Pro Pro Met Glu Lys Leu Arg Leu Leu
465                 470                 475                 480

Leu Glu Lys Leu Ser His His Ala Lys Phe Thr His Glu Tyr Ser
                485                 490                 495

<210> SEQ ID NO 11
<211> LENGTH: 1125
<212> TYPE: DNA
<213> ORGANISM: Canis familiaris

<400> SEQUENCE: 11
atgctggctc ttcacggggc cgtggttaag gtgaaacggg gccggctgcg tccagggctt      60
ggcgctacgc ctgatgccgg gatcgagggc ctgaccacct gttgcctcct ctttgctcag     120
ggtatcaaga aaccgttcac cgaggtcatc cgcgccaaca tcggggacgc ccaggccatg     180
ggccagcagc ctataacctt cctccgacag gtgatggcac tgtgcaccta ccccaacctg     240
ctggacagcc ccagcttccc agaagatgct aagaaacgag cccggaggat cctacaggct     300
tgtggcggga cagcctgggt cctacagt gccagccagg cgtcaactg catccgcgag        360 gacgtggccg cctacgtcac caggagggac ggcggggtgc ccgcgaccc cttcaacatt      420 tacctgacca ctggagccag cgacggcatt tctacgatcc tgaagatcct ggtgtccggg     480
ggtggcaagt cgcggacggg cgtgctgatc cccatcccac agtaccccct ctactcggcc     540
gtcatctccg agctcgacgc catccaggtg aactactact tggacgagga gaactgctgg     600
gccctcgacg tgaacgagct ccggcgggcc gtgcaggagg ctaaggacca ctgtaacccc     660
aaggtgctgt gcatcatcaa ccccgggaac cccacaggtc aggtgcaaag caggaagtgc     720
atagaggacg tcatccactt tgcctgggaa gagaagctct ttctcctggc agatgaggtg     780
taccaggaca acgtgtactc tccggactgc agattccact ccttcaagaa ggtgctctac     840
gagatggggc ccgagtactc gagcaacgtg gagcttgcgt ccttccactc tacctccaag     900
ggctacatgg gcgagtacgt tggccttggc ttcctcccgc ggccccacca tcggccctg      960 cccgctggcg gcctgctgcg cggggaacac ggggcccatc tcagggggcc tgtgcatgag    1020
ctcagccctg gtgcagggac gcccgtgcgg cgaggtcctg ctggggcccc gggctcccg     1080 cgcttcctgc cgggcccacg ctgctgccct gggactgaac cctga                    1125

<210> SEQ ID NO 12
<211> LENGTH: 374
<212> TYPE: PRT
<213> ORGANISM: Canis familiaris

<400> SEQUENCE: 12

Met Leu Ala Leu His Gly Ala Val Val Lys Val Lys Arg Gly Arg Leu
1               5                   10                  15

Arg Pro Gly Leu Gly Ala Thr Pro Asp Ala Gly Ile Glu Gly Leu Thr
            20                  25                  30

Thr Cys Cys Leu Leu Phe Ala Gln Gly Ile Lys Lys Pro Phe Thr Glu
```

```
                35                  40                  45
Val Ile Arg Ala Asn Ile Gly Asp Ala Gln Met Gly Gln Gln Pro
 50                  55                  60
Ile Thr Phe Leu Arg Gln Val Met Ala Leu Cys Thr Tyr Pro Asn Leu
 65                  70                  75                  80
Leu Asp Ser Pro Ser Phe Pro Glu Asp Ala Lys Lys Arg Ala Arg Arg
                 85                  90                  95
Ile Leu Gln Ala Cys Gly Gly Asn Ser Leu Gly Ser Tyr Ser Ala Ser
                100                 105                 110
Gln Gly Val Asn Cys Ile Arg Glu Asp Val Ala Ala Tyr Val Thr Arg
            115                 120                 125
Arg Asp Gly Gly Val Pro Ala Asp Pro Phe Asn Ile Tyr Leu Thr Thr
130                 135                 140
Gly Ala Ser Asp Gly Ile Ser Thr Ile Leu Lys Ile Leu Val Ser Gly
145                 150                 155                 160
Gly Gly Lys Ser Arg Thr Gly Val Leu Ile Pro Ile Pro Gln Tyr Pro
                165                 170                 175
Leu Tyr Ser Ala Val Ile Ser Glu Leu Asp Ala Ile Gln Val Asn Tyr
            180                 185                 190
Tyr Leu Asp Glu Glu Asn Cys Trp Ala Leu Asp Val Asn Glu Leu Arg
        195                 200                 205
Arg Ala Val Gln Glu Ala Lys Asp His Cys Asn Pro Lys Val Leu Cys
    210                 215                 220
Ile Ile Asn Pro Gly Asn Pro Thr Gly Gln Val Gln Ser Arg Lys Cys
225                 230                 235                 240
Ile Glu Asp Val Ile His Phe Ala Trp Glu Glu Lys Leu Phe Leu Leu
                245                 250                 255
Ala Asp Glu Val Tyr Gln Asp Asn Val Tyr Ser Pro Asp Cys Arg Phe
            260                 265                 270
His Ser Phe Lys Lys Val Leu Tyr Glu Met Gly Pro Glu Tyr Ser Ser
        275                 280                 285
Asn Val Glu Leu Ala Ser Phe His Ser Thr Ser Lys Gly Tyr Met Gly
    290                 295                 300
Glu Tyr Val Gly Leu Gly Phe Leu Pro Arg Pro His His Ser Ala Leu
305                 310                 315                 320
Pro Ala Gly Gly Leu Leu Arg Gly Glu Gly Ala His Leu Arg Gly
                325                 330                 335
Pro Val His Glu Leu Ser Pro Gly Ala Gly Thr Pro Val Arg Arg Gly
            340                 345                 350
Pro Ala Gly Ala Pro Gly Ser Pro Arg Phe Leu Pro Gly Pro Arg Cys
        355                 360                 365
Cys Pro Gly Thr Glu Pro
    370

<210> SEQ ID NO 13
<211> LENGTH: 1623
<212> TYPE: DNA
<213> ORGANISM: Xenopus laevis

<400> SEQUENCE: 13
atgagtattc tcaggggtgtc tctgaggggg gtgctggccc ccaatgcttc tgttgtgttt      60
aggagcagat tgccccccca gctcacttct gccctcctgt gccccctcag gtcgctgtcg     120
ggaacgccgc tggctgaacc ggacgggaaa gttactcgca agatgtctga gaacgggaca     180
tgcaaccgga tcctgactct ggactccatg aatccctgta tccagaaagt ggaatacgca     240
```

-continued

```
gtgaggggcc ccatcgtcat cagggctgtg gagctggaga aagaactgca gcagggggta    300
aagaagccat tcacagaagt gatcaaagcc aatattggag atgcccatgc aatgggtcag    360
aaacccgtta ctttcctgcg ccaggtgagt gccatctgtc tgtacccga gctcatgaat     420 gacaacaagt tcccggagga cgtgaagcag aaggcagcga ggatcctgca ggcgtgtggc    480
gggcacagca ttgggggccta cagcgccagc caagggattg aagtgatccg acaagatgtg   540
gccaagtaca ttgagagaag ggatgggggt atcctgtccg accccaacaa catctacctc    600
tccacggggg ccagtgactc tattgtgaca atgctgaagt tgctggtgtc tgggcaaggg    660
aaatcccgaa ctggggtgat gatcccgatc cctcaatacc cgctgtattc tgcggccctg    720
gcagagttgg atgccgtgca ggttaattat tatctggatg aggagaactg ctgggccctg    780
gacatcaacg agctgcggag agcactagcg gaggcccgaa acattgtga ccccaaagta     840 ctgtgcatta ttaacccagg aaaccctaca gggcaggtgc agagccgcaa gtgcattgag    900
gacgtgatcc gttttgctgc tgaagagaat ctttcctga tggcggatga ggtctaccaa     960
gataatgtct atgccaaggg ctgtgccttt cactccttca aaaaggttct ctttgagatg    1020
ggacccaagt attcagaaac gctggaactg gcttctttcc actccacatc caagggatac    1080
atgggagagt gcgggttcag aggggggttac atggaagtga tcaatatgga tcctgctgtc   1140
aagcaacaac taaccaagtt ggtgtctgtg cgtctgtgcc ccccagtgcc ggggcaagta    1200
ttacttgatg tgattgtgaa cccaccaaag cctggggagc cctcctacaa acagttcatt    1260
tctgagaaac aggctgtgct caataacctg gctgagaaag ctcgtctcac tgaggaaatc    1320
ctaaaccaag cgcctgggat ccgctgtaac ccagtccagg gagccatgta ctcgtttcca    1380
aggatccaca tcccagagaa ggccattaaa cttgcacagg ctgagggaca ggccccagac    1440
atgttcttct gtatgaagct gctggaagag actggcattt gtgtggtacc tggaagtgga    1500
tttggacaac gtgagggcac tcaccatttc aggatgacca tcctccctcc caccgataag    1560
ctgaagagcc tgttagagcg gctgaaggat ttccaccaga aatttatgga tgagtattcc    1620
tag                                                                  1623
```

<210> SEQ ID NO 14
<211> LENGTH: 540
<212> TYPE: PRT
<213> ORGANISM: Xenopus laevis

<400> SEQUENCE: 14

```
Met Ser Ile Leu Arg Gly Ser Leu Arg Gly Val Leu Ala Pro Asn Ala
1               5                   10                  15

Ser Val Val Phe Arg Ser Arg Leu Pro Pro Gln Leu Thr Ser Ala Leu
            20                  25                  30

Leu Cys Pro Leu Arg Ser Leu Ser Gly Thr Pro Leu Ala Glu Pro Asp
        35                  40                  45

Gly Lys Val Thr Arg Lys Met Ser Glu Asn Gly Thr Cys Asn Arg Ile
    50                  55                  60

Leu Thr Leu Asp Ser Met Asn Pro Cys Ile Gln Lys Val Glu Tyr Ala
65                  70                  75                  80

Val Arg Gly Pro Ile Val Ile Arg Ala Val Glu Leu Glu Lys Glu Leu
                85                  90                  95

Gln Gln Gly Val Lys Lys Pro Phe Thr Glu Val Ile Lys Ala Asn Ile
            100                 105                 110

Gly Asp Ala His Ala Met Gly Gln Lys Pro Val Thr Phe Leu Arg Gln
        115                 120                 125
```

```
Val Ser Ala Ile Cys Leu Tyr Pro Glu Leu Met Asn Asp Asn Lys Phe
    130                 135                 140

Pro Glu Asp Val Lys Gln Lys Ala Ala Arg Ile Leu Gln Ala Cys Gly
145                 150                 155                 160

Gly His Ser Ile Gly Ala Tyr Ser Ala Ser Gln Gly Ile Glu Val Ile
                165                 170                 175

Arg Gln Asp Val Ala Lys Tyr Ile Glu Arg Arg Asp Gly Gly Ile Leu
                180                 185                 190

Ser Asp Pro Asn Asn Ile Tyr Leu Ser Thr Gly Ala Ser Asp Ser Ile
            195                 200                 205

Val Thr Met Leu Lys Leu Leu Val Ser Gly Gln Gly Lys Ser Arg Thr
            210                 215                 220

Gly Val Met Ile Pro Ile Pro Gln Tyr Pro Leu Tyr Ser Ala Ala Leu
225                 230                 235                 240

Ala Glu Leu Asp Ala Val Gln Val Asn Tyr Tyr Leu Asp Glu Glu Asn
                245                 250                 255

Cys Trp Ala Leu Asp Ile Asn Glu Leu Arg Arg Ala Leu Ala Glu Ala
                260                 265                 270

Arg Lys His Cys Asp Pro Lys Val Leu Cys Ile Ile Asn Pro Gly Asn
            275                 280                 285

Pro Thr Gly Gln Val Gln Ser Arg Lys Cys Ile Glu Asp Val Ile Arg
            290                 295                 300

Phe Ala Ala Glu Glu Asn Leu Phe Leu Met Ala Asp Glu Val Tyr Gln
305                 310                 315                 320

Asp Asn Val Tyr Ala Lys Gly Cys Ala Phe His Ser Phe Lys Lys Val
                325                 330                 335

Leu Phe Glu Met Gly Pro Lys Tyr Ser Glu Thr Leu Glu Leu Ala Ser
                340                 345                 350

Phe His Ser Thr Ser Lys Gly Tyr Met Gly Glu Cys Gly Phe Arg Gly
            355                 360                 365

Gly Tyr Met Glu Val Ile Asn Met Asp Pro Ala Val Lys Gln Gln Leu
            370                 375                 380

Thr Lys Leu Val Ser Val Arg Leu Cys Pro Pro Val Pro Gly Gln Val
385                 390                 395                 400

Leu Leu Asp Val Ile Val Asn Pro Pro Lys Pro Gly Glu Pro Ser Tyr
                405                 410                 415

Lys Gln Phe Ile Ser Glu Lys Gln Ala Val Leu Asn Asn Leu Ala Glu
                420                 425                 430

Lys Ala Arg Leu Thr Glu Glu Ile Leu Asn Gln Ala Pro Gly Ile Arg
            435                 440                 445

Cys Asn Pro Val Gln Gly Ala Met Tyr Ser Phe Pro Arg Ile His Ile
            450                 455                 460

Pro Glu Lys Ala Ile Lys Leu Ala Gln Ala Glu Gly Gln Ala Pro Asp
465                 470                 475                 480

Met Phe Phe Cys Met Lys Leu Leu Glu Glu Thr Gly Ile Cys Val Val
                485                 490                 495

Pro Gly Ser Gly Phe Gly Gln Arg Glu Gly Thr His His Phe Arg Met
            500                 505                 510

Thr Ile Leu Pro Pro Thr Asp Lys Leu Lys Ser Leu Leu Glu Arg Leu
            515                 520                 525

Lys Asp Phe His Gln Lys Phe Met Asp Glu Tyr Ser
530                 535                 540
```

<210> SEQ ID NO 15
<211> LENGTH: 1707
<212> TYPE: DNA
<213> ORGANISM: Drosophila melanogaster

<400> SEQUENCE: 15

```
atgagtcgaa tgctaattaa acctgctgcc gccacagttt cggccgcatt gcagcagcac      60
cagcgccagc agcaacagta cgttattcgc cgctggaaat cgttcctgca caacaacagc     120
aacaatgcca atcgacgtgc ggcgaaatca acggcaacag caacggtgac ggcagcagcg     180
acgtcgcagc gccatggaac aagcggcgat tcattcaac cgttagacgt ccgccgttcc      240
ttttcaacca gccacaaaat gccgtcgtcg tcgaaagcgc tcacactgga taacataaat     300
cccaacttta ttgccatgga atatgccgtt cgcggtcctc tggtgattcg tgctggggaa     360
atcgagaagg aactggaaaa gggtgtcaag aagccattcg accaggtgat ccgtgccaac     420
atcggtgatt gccatgcgat gggccagcag cccttgacct tcctgcgaca gctgttggcg     480
ctgaccttcg agacacgtct gctggattca cccgattatc ccgaggacgt caagaagcgc     540
gcctgtgcca ttttgaacgg ctgccagggt caatcgtgg gctcgtacac cgactccgcc      600
ggtctggagg tggtgcgtcg ccaggttgct cagtacatcg agaaaaggga tggcggcatc     660
gcctccaatt ggcaggacat ctatctaacc ggcggtgcct ctcccggcat caagagcatt     720
ctctccatga tcaacgccga ggtgggatgc aaggcgcctg tgtcatggt gcccattccg      780
cagtacccac tgtactcggc caccatctcc gaatacggca tgaccaaggt ggattactat     840
ctggaggagg agaccggttg gagcctggac aggaaggagc tgcaacggtc ctacgatgag     900
gcgaagaagg tctgcaatcc gcgtgccctg gtcgtgatca atccgggcaa tcccaccgga     960
caggtactga cccgcgagaa catcgaggag atcattaagt tcgcacacga taacaaggtg    1020
ctggtgctgg ccgatgaggt gtaccaggac aatgtctacg acaagaactc caagttctgg    1080
tcgttcaaga aggtggccta cgaaatgggc gaccccatc gtaatctgga atggtcagt     1140
ttcctgtcca cctcgaaggg ctatctgggc gagtgcggca ttcgcggcgg ttacatggag    1200
gttctcaatc ttgatcccaa ggtcaaggcc atgctgacca gtcgataac ggcggcgctt     1260
tgcagcacca ccgctggcca ggtggccgtg agtgccctgg tcaatccacc gcagcccgga    1320
gagccatcat acgatctgta caagaaggag cgcgatggca ttctggccgc tctaaaagaa    1380
cgggccgagc tcgtccacaa ggcactgaac agcttcgaag gctacaaggt taaccccgta    1440
cagggcgcca tgtacgtctt tccacagatc gagatcccgc caaggcgat cgaggcggcc    1500
aaggccaagg gcatggcccc cgatgttttc tacgcatttg agctgctcga cgcgagcggc    1560
atttgcattg ttcctggcag tggatttggt cagaagcccg gcacgtggca tttccgaagc    1620
acgatcctcc cgcaaacgga caagctgaag ctgatgatgg agaagttccg tgtgttccac    1680
gccgagttca tgaagaagta caagtag                                        1707
```

<210> SEQ ID NO 16
<211> LENGTH: 568
<212> TYPE: PRT
<213> ORGANISM: Drosophila melanogaster

<400> SEQUENCE: 16

Met Ser Arg Met Leu Ile Lys Pro Ala Ala Ala Thr Val Ser Ala Ala
1               5                   10                  15

Leu Gln Gln His Gln Arg Gln Gln Gln Gln Tyr Val Ile Arg Arg Trp
            20                  25                  30

Lys Ser Phe Leu His Asn Asn Ser Asn Asn Ala Asn Arg Arg Ala Ala

```
                35                  40                  45
Lys Ser Thr Ala Thr Ala Thr Val Thr Ala Ala Thr Ser Gln Arg
        50                  55                  60
His Gly Thr Ser Gly Asp Phe Ile Gln Pro Leu Asp Val Arg Arg Ser
65                      70                  75                  80
Phe Ser Thr Ser His Lys Met Pro Ser Ser Lys Ala Leu Thr Leu
                85                  90                  95
Asp Asn Ile Asn Pro Asn Phe Ile Ala Met Glu Tyr Ala Val Arg Gly
                100                 105                 110
Pro Leu Val Ile Arg Ala Gly Glu Ile Glu Lys Glu Leu Glu Lys Gly
                115                 120                 125
Val Lys Lys Pro Phe Asp Gln Val Ile Arg Ala Asn Ile Gly Asp Cys
        130                 135                 140
His Ala Met Gly Gln Gln Pro Leu Thr Phe Leu Arg Gln Leu Leu Ala
145                 150                 155                 160
Leu Thr Phe Glu Thr Arg Leu Leu Asp Ser Pro Asp Tyr Pro Glu Asp
                165                 170                 175
Val Lys Lys Arg Ala Cys Ala Ile Leu Asn Gly Cys Gln Gly Gln Ser
                180                 185                 190
Val Gly Ser Tyr Thr Asp Ser Ala Gly Leu Glu Val Val Arg Arg Gln
        195                 200                 205
Val Ala Gln Tyr Ile Glu Lys Arg Asp Gly Gly Ile Ala Ser Asn Trp
        210                 215                 220
Gln Asp Ile Tyr Leu Thr Gly Gly Ala Ser Pro Gly Ile Lys Ser Ile
225                 230                 235                 240
Leu Ser Met Ile Asn Ala Glu Val Gly Cys Lys Ala Pro Gly Val Met
                245                 250                 255
Val Pro Ile Pro Gln Tyr Pro Leu Tyr Ser Ala Thr Ile Ser Glu Tyr
                260                 265                 270
Gly Met Thr Lys Val Asp Tyr Tyr Leu Glu Glu Thr Gly Trp Ser
                275                 280                 285
Leu Asp Arg Lys Glu Leu Gln Arg Ser Tyr Asp Glu Ala Lys Lys Val
        290                 295                 300
Cys Asn Pro Arg Ala Leu Val Val Ile Asn Pro Gly Asn Pro Thr Gly
305                 310                 315                 320
Gln Val Leu Thr Arg Glu Asn Ile Glu Glu Ile Lys Phe Ala His
                    325                 330                 335
Asp Asn Leu Val Leu Val Leu Ala Asp Glu Val Tyr Gln Asp Asn Val
                340                 345                 350
Tyr Asp Lys Asn Ser Lys Phe Trp Ser Phe Lys Lys Val Ala Tyr Glu
        355                 360                 365
Met Gly Asp Pro Tyr Arg Asn Leu Glu Met Val Ser Phe Leu Ser Thr
370                 375                 380
Ser Lys Gly Tyr Leu Gly Glu Cys Gly Ile Arg Gly Tyr Met Glu
385                 390                 395                 400
Val Leu Asn Leu Asp Pro Lys Val Lys Ala Met Leu Thr Lys Ser Ile
                405                 410                 415
Thr Ala Ala Leu Cys Ser Thr Thr Ala Gly Gln Val Ala Val Ser Ala
                420                 425                 430
Leu Val Asn Pro Pro Gln Pro Gly Glu Pro Ser Tyr Asp Leu Tyr Lys
            435                 440                 445
Lys Glu Arg Asp Gly Ile Leu Ala Ala Leu Lys Glu Arg Ala Glu Leu
    450                 455                 460
```

```
Val His Lys Ala Leu Asn Ser Phe Glu Gly Tyr Lys Val Asn Pro Val
465                 470                 475                 480

Gln Gly Ala Met Tyr Val Phe Pro Gln Ile Glu Ile Pro Pro Lys Ala
            485                 490                 495

Ile Glu Ala Ala Lys Ala Lys Gly Met Ala Pro Asp Val Phe Tyr Ala
        500                 505                 510

Phe Glu Leu Leu Glu Thr Ser Gly Ile Cys Ile Val Pro Gly Ser Gly
            515                 520                 525

Phe Gly Gln Lys Pro Gly Thr Trp His Phe Arg Ser Thr Ile Leu Pro
        530                 535                 540

Gln Thr Asp Lys Leu Lys Leu Met Met Glu Lys Phe Arg Val Phe His
545                 550                 555                 560

Ala Glu Phe Met Lys Lys Tyr Lys
                565
```

<210> SEQ ID NO 17
<211> LENGTH: 1515
<212> TYPE: DNA
<213> ORGANISM: Caenorhabditis elegans

<400> SEQUENCE: 17

```
atgcgaaccg tacaagcaat ttccggactc gtcacaagtc gcttttcgg cacatccact      60
agaatcatgg ctagcggaaa gactttgaac acctccaaca tcaatccaaa tgttatcaag    120
atggagtatg ctgttcgtgg accaatcgtg atccgtgccg tggagcttga aaagagctt     180
gcgaccggtg ctcagaagcc attcccaaat gtcatcaagg ctaatattgg agatgctcat    240
gctatgggtc aaaagccgat tactttcatt cgccagctcc tcgcgtgtat tgtcaaccca    300
gagatcatga aaacggacaa atcaattcca tctgatgtta cgaacatgc aaatgcattc    360
cttggaagtt gtggaggaaa atccgctgga gcatacagtc agagtacggg agtggaaatt    420
gtacgaaaac acgtgcaga gtatattaag agacgtgatg gaggaattcc atgcaattca    480
gaagatgtct gcttgtctgg aggagcttct gaatcaatcc gaaatgttct caaacttttt    540
atcaatcata caacgcaaa gaaagtcgga gtcatgattc caattccaca atatccactc    600
tattctgcca ctatcgaaga attcggactt ggacaagttg atactatttt gagtgaatcg    660
tctaattggt ccatggatga agctgaactt gaaagatctt tcaatgatca ctgcaaagaa    720
tacgatattc gagtttttgtg tatcatcaat ccaggaaatc ctaccggaca agcactttct    780
cgtgaaaata ttgagactat catcaagttt gcacaaaaga gaacctgtt ccttatgggct    840
gatgaggttt atcaagacaa cgtctacgct caaggatcgc aattccattc attcaagaag    900
gttcttgtgg agatgggaga gccatacaat aaaatggaat tggcttcttt ccattcggta    960
tccaaaggat acatgggaga atgcggaatg cgtggaggat atgttgaatt cttgaatctc   1020
gacccagaag tgtatgtcct ttcaaaaaaa atgatctctg ccaaattgtg ctccacagta   1080
ctcggacaag ccgtcattga tgccgttgtg aatccaccaa aggaaggaga tgcatcgtat   1140
gctctgtgga acaagaaaa ggatgcagta cttgcttctc ttaaggaacg tgctacactc   1200
gtcgagaagg catacagtag cattgatgga atcagctgta atccagttca aggagccatg   1260
tacgctttcc cgcaaatcac gattccacag agagctgttg aaaaagctca gtctttgaac   1320
caacaacctg atttcttcta tgctatgcaa cttcttgaga ccaccggaat ctgtatcgtg   1380
ccaggaagtg gatttggaca aaagacgga acttatcatt tcagaacgac aattcttcca   1440
cagccagaac tcttcaaaga catgctctcc cggttcactg atttccacca aaaattcctt   1500
gccgaataca agtag                                                    1515
```

<210> SEQ ID NO 18
<211> LENGTH: 504
<212> TYPE: PRT
<213> ORGANISM: Caenorhabditis elegans

<400> SEQUENCE: 18

```
Met Arg Thr Val Gln Ala Ile Ser Gly Leu Val Thr Ser Arg Phe Phe
1               5                   10                  15

Gly Thr Ser Thr Arg Ile Met Ala Ser Gly Lys Thr Leu Asn Thr Ser
            20                  25                  30

Asn Ile Asn Pro Asn Val Ile Lys Met Glu Tyr Ala Val Arg Gly Pro
        35                  40                  45

Ile Val Ile Arg Ala Val Glu Leu Glu Lys Glu Leu Ala Thr Gly Ala
    50                  55                  60

Gln Lys Pro Phe Pro Asn Val Ile Lys Ala Asn Ile Gly Asp Ala His
65                  70                  75                  80

Ala Met Gly Gln Lys Pro Ile Thr Phe Ile Arg Gln Leu Leu Ala Cys
                85                  90                  95

Ile Val Asn Pro Glu Ile Met Lys Thr Asp Lys Ser Ile Pro Ser Asp
            100                 105                 110

Val Ile Glu His Ala Asn Ala Phe Leu Gly Ser Cys Gly Gly Lys Ser
        115                 120                 125

Ala Gly Ala Tyr Ser Gln Ser Thr Gly Val Glu Ile Val Arg Lys His
    130                 135                 140

Val Ala Glu Tyr Ile Lys Arg Arg Asp Gly Gly Ile Pro Cys Asn Ser
145                 150                 155                 160

Glu Asp Val Cys Leu Ser Gly Gly Ala Ser Glu Ser Ile Arg Asn Val
                165                 170                 175

Leu Lys Leu Phe Ile Asn His Asn Asn Ala Lys Lys Val Gly Val Met
            180                 185                 190

Ile Pro Ile Pro Gln Tyr Pro Leu Tyr Ser Ala Thr Ile Glu Glu Phe
        195                 200                 205

Gly Leu Gly Gln Val Gly Tyr Tyr Leu Ser Glu Ser Ser Asn Trp Ser
    210                 215                 220

Met Asp Glu Ala Glu Leu Glu Arg Ser Phe Asn Asp His Cys Lys Glu
225                 230                 235                 240

Tyr Asp Ile Arg Val Leu Cys Ile Ile Asn Pro Gly Asn Pro Thr Gly
                245                 250                 255

Gln Ala Leu Ser Arg Glu Asn Ile Glu Thr Ile Ile Lys Phe Ala Gln
            260                 265                 270

Lys Lys Asn Leu Phe Leu Met Ala Asp Glu Val Tyr Gln Asp Asn Val
        275                 280                 285

Tyr Ala Gln Gly Ser Gln Phe His Ser Phe Lys Lys Val Leu Val Glu
    290                 295                 300

Met Gly Glu Pro Tyr Asn Lys Met Glu Leu Ala Ser Phe His Ser Val
305                 310                 315                 320

Ser Lys Gly Tyr Met Gly Glu Cys Gly Met Arg Gly Gly Tyr Val Glu
                325                 330                 335

Phe Leu Asn Leu Asp Pro Glu Val Tyr Val Leu Phe Lys Lys Met Ile
            340                 345                 350

Ser Ala Lys Leu Cys Ser Thr Val Leu Gly Gln Ala Val Ile Asp Ala
        355                 360                 365

Val Val Asn Pro Pro Lys Glu Gly Asp Ala Ser Tyr Ala Leu Trp Lys
    370                 375                 380
```

```
Gln Glu Lys Asp Ala Val Leu Ala Ser Leu Lys Glu Arg Ala Thr Leu
385                 390                 395                 400

Val Glu Lys Ala Tyr Ser Ser Ile Asp Gly Ile Ser Cys Asn Pro Val
            405                 410                 415

Gln Gly Ala Met Tyr Ala Phe Pro Gln Ile Thr Ile Pro Gln Arg Ala
        420                 425                 430

Val Glu Lys Ala Gln Ser Leu Asn Gln Gln Pro Asp Phe Phe Tyr Ala
    435                 440                 445

Met Gln Leu Leu Glu Thr Thr Gly Ile Cys Ile Val Pro Gly Ser Gly
        450                 455                 460

Phe Gly Gln Lys Asp Gly Thr Tyr His Phe Arg Thr Thr Ile Leu Pro
465                 470                 475                 480

Gln Pro Glu Leu Phe Lys Asp Met Leu Ser Arg Phe Thr Asp Phe His
            485                 490                 495

Gln Lys Phe Leu Ala Glu Tyr Lys
            500
```

<210> SEQ ID NO 19
<211> LENGTH: 1458
<212> TYPE: DNA
<213> ORGANISM: Oryza sativa japonica

<400> SEQUENCE: 19

```
atgttcggcg gcggcggcgg cggcgggagg aagccgctgg actacgagga gctgaacgag      60
aacgtgaaga aggtgcagta cgcggtgcgg ggggagctgt acctgcgcgc ctccgagctc     120
cagaaggagg gcaagaagat catcttcacc aacgtcggca acccacacgc gctcggccag     180
aagccgctca ccttccccg ccaggttgtg gcgctgtgcc aggcccccttt cctgctcgat     240
gatcccaacg tcggccttat cttccccgcc gacgccatcg cgcgggccaa gcactacctc     300
gccatggcac ccgtggact aggtgcttac agtgattccc gaggtatccc tggtattagg     360
aaggaagtcg ccgagttcat cgagaggcgt gatggttatc caagtgatcc agaacttatt     420
tacctcacag atggtgccag caaaggtgtg atgcaaatgc tgaataccat tatcagaaat     480
gagagagatg ggattctggt tcctgttcca caatacccgc tttattctgc tgccatttcc     540
ctctttggtg gttctctcgt gccatactac ttagaagaag aggctaactg gggacttgac     600
ttcgtcaatc tccgacagac tgtggcgtca gcgcggtcaa agggaatcac tgttcgagca     660
atggtgatta tcaacccagg aaaccctact ggccaatgcc ttagtgaagg aaacataaag     720
gaacttctca aattctgctt ccatgagaac ttagttctgc ttgcagatga agtctatcaa     780
cagaacattt atcaagatga cgcccatttt ataagtgcta gaaaggttct gtttgacatg     840
ggtcctccta tgagcaggga gttcagctg gtttctttcc atactgtgtc aaaaggatat     900
tgggggagt gtggacaacg tggagggtat tttgaaatga caaatcttcc tcccaagaca     960
gtagacgaga tctacaaggt tgcatcaatc gcactcagtc aaatgttcc tgggcagatc    1020
tttatgggtt taatggttaa ccctcctaag cctggagata tctcttatct gaagttttct    1080
gctgaaagca agtctatcct cgagtctttg aggaggagag cacgcctgat gacagatggt    1140
ttcaatagtt gccgaaatgt tgtctgcaat ttcacagaag gagctatgta ctctttcccc    1200
caaatacgct taccaccaaa agctatagat gcagccaaaa gggctggcaa gcggccgat    1260
gttttctact gcctcaagct tcttgaagca actggaatat ccactgttcc agggtcaggt    1320
ttcggacaaa aagaagggt gttccacctg aggacgacca cctgccagc tgaggaggac    1380
atgcctgcca tcatgaccag cttcaagaag ttcaacgaca ctttcatgga tcagtacgat    1440
```

```
ggctactcca ggatgtga                                                  1458
```

<210> SEQ ID NO 20
<211> LENGTH: 485
<212> TYPE: PRT
<213> ORGANISM: Oryza sativa japonica

<400> SEQUENCE: 20

```
Met Phe Gly Gly Gly Gly Gly Gly Arg Lys Pro Leu Asp Tyr Glu
1               5                   10                  15

Glu Leu Asn Glu Asn Val Lys Lys Val Gln Tyr Ala Val Arg Gly Glu
                20                  25                  30

Leu Tyr Leu Arg Ala Ser Glu Leu Gln Lys Glu Gly Lys Lys Ile Ile
            35                  40                  45

Phe Thr Asn Val Gly Asn Pro His Ala Leu Gly Gln Lys Pro Leu Thr
65      50              55                  60

Phe Pro Arg Gln Val Val Ala Leu Cys Gln Ala Pro Phe Leu Leu Asp
65              70                  75                  80

Asp Pro Asn Val Gly Leu Ile Phe Pro Ala Asp Ala Ile Ala Arg Ala
                85                  90                  95

Lys His Tyr Leu Ala Met Ala Pro Gly Gly Leu Gly Ala Tyr Ser Asp
            100                 105                 110

Ser Arg Gly Ile Pro Gly Ile Arg Lys Glu Val Ala Glu Phe Ile Glu
        115                 120                 125

Arg Arg Asp Gly Tyr Pro Ser Asp Pro Glu Leu Ile Tyr Leu Thr Asp
    130                 135                 140

Gly Ala Ser Lys Gly Val Met Gln Met Leu Asn Thr Ile Ile Arg Asn
145                 150                 155                 160

Glu Arg Asp Gly Ile Leu Val Pro Val Pro Gln Tyr Pro Leu Tyr Ser
                165                 170                 175

Ala Ala Ile Ser Leu Phe Gly Gly Ser Leu Val Pro Tyr Tyr Leu Glu
            180                 185                 190

Glu Glu Ala Asn Trp Gly Leu Asp Phe Val Asn Leu Arg Gln Thr Val
        195                 200                 205

Ala Ser Ala Arg Ser Lys Gly Ile Thr Val Arg Ala Met Val Ile Ile
    210                 215                 220

Asn Pro Gly Asn Pro Thr Gly Gln Cys Leu Ser Glu Gly Asn Ile Lys
225                 230                 235                 240

Glu Leu Leu Lys Phe Cys Phe His Glu Asn Leu Val Leu Leu Ala Asp
                245                 250                 255

Glu Val Tyr Gln Gln Asn Ile Tyr Gln Asp Glu Arg Pro Phe Ile Ser
            260                 265                 270

Ala Arg Lys Val Leu Phe Asp Met Gly Pro Pro Met Ser Arg Glu Val
        275                 280                 285

Gln Leu Val Ser Phe His Thr Val Ser Lys Gly Tyr Trp Gly Glu Cys
    290                 295                 300

Gly Gln Arg Gly Gly Tyr Phe Glu Met Thr Asn Leu Pro Pro Lys Thr
305                 310                 315                 320

Val Asp Glu Ile Tyr Lys Val Ala Ser Ile Ala Leu Ser Pro Asn Val
                325                 330                 335

Pro Gly Gln Ile Phe Met Gly Leu Met Val Asn Pro Pro Lys Pro Gly
            340                 345                 350

Asp Ile Ser Tyr Leu Lys Phe Ser Ala Glu Ser Lys Ser Ile Leu Glu
        355                 360                 365
```

```
Ser Leu Arg Arg Arg Ala Arg Leu Met Thr Asp Gly Phe Asn Ser Cys
        370                 375                 380

Arg Asn Val Val Cys Asn Phe Thr Glu Gly Ala Met Tyr Ser Phe Pro
385                 390                 395                 400

Gln Ile Arg Leu Pro Pro Lys Ala Ile Asp Ala Ala Lys Arg Ala Gly
                405                 410                 415

Lys Ala Ala Asp Val Phe Tyr Cys Leu Lys Leu Leu Glu Ala Thr Gly
                420                 425                 430

Ile Ser Thr Val Pro Gly Ser Gly Phe Gly Gln Lys Glu Gly Val Phe
                435                 440                 445

His Leu Arg Thr Thr Ile Leu Pro Ala Glu Glu Asp Met Pro Ala Ile
        450                 455                 460

Met Thr Ser Phe Lys Lys Phe Asn Asp Thr Phe Met Asp Gln Tyr Asp
465                 470                 475                 480

Gly Tyr Ser Arg Met
                485

<210> SEQ ID NO 21
<211> LENGTH: 1452
<212> TYPE: DNA
<213> ORGANISM: Oryza sativa japonica

<400> SEQUENCE: 21
atggctgctc ccagcgtcgc cgtcgacaac ctcaacccca aggttttgaa ttgtgagtat      60
gcagtgcgtg gagagattgt gatccatgct cagcgcctgc agcaacagct acagactcaa     120
ccagggtctc ttccttttga tgagatccta tactgcaaca ttgggaatcc ccagtctctt     180
ggtcagaagc cagttacatt cttcagggag gttattgctc tttgtgatca tccatgcttg     240
ttggaaaagg aggaaaccaa atcattgttc agtgctgatg ccatttctcg agcaacaaca     300
attcttgcct cgattcctgg aagagcaact ggagcataca gccacagcca gggcatcaaa     360
gggctgcgtg atgcaattgc tgctggaatt gcatcacgtg acggataccc tgcaaatgca     420
gacgacattt tccttactga cggagcaagc cctggagttc acatgatgat gcagttactg     480
ataaggaacg agaaagatgg cattctctgc ccaattcctc aatatccttt gtactcagcc     540
tccattgctc ttcatggtgg agctcttgtc ccgtattatc ttaatgaatc aacaggctgg     600
ggtttggaga tctctgacct taagaagcaa ctcgaagatt ctcggttgaa aggcattgat     660
gttagggctt tggtagttat caatccagga aatccaactg gcaggttcct gctgaggaa      720 aaccaacggg acatagtgaa gttctgcaaa atgagggac ttgttcttct ggctgatgag      780
gtgtaccaag agaacatcta tgttgacaac aagaaattta actcttttcaa gaagatagcg     840 agatccatgg gatacaacga ggatgatctc cctttagtat catttcaatc tgtttctaag     900
ggatattatg gtgaatgtgg caaaagagga ggctacatgg agattactgg cttcagtgct     960
ccagttagag agcagatcta caaagtggcg tcagtgaact tatgttccaa tatcactggc    1020
cagatccttg ccagcctcgt catgaatcca ccaaaggctg gagatgcatc atatgcttca    1080
tacaaggcag agaagatgg aatcctccaa tcattagctc gccgtgcaaa ggcattggag    1140
aatgctttca acagtcttga gggaattaca tgcaacaaaa ctgaaggagc aatgtacctc    1200
ttccctcagc ttagtctgcc acaaaaggca attgacgctg ctaaagctgc taacaaagca    1260
cctgatgctt tctatgccct tcgtctcctc gaggcaaccg gaattgttgt tgtccctgga    1320
tctggatttg gccaagttcc tggcacatgg cacatcagat gcacaatcct gccacaggag    1380
gagaagatcc ccgcgatcat ctcccgcttc aaggcattcg atgagggctt catggcagcg    1440
```
taccgcgact ga                                                                  1452

<210> SEQ ID NO 22
<211> LENGTH: 483
<212> TYPE: PRT
<213> ORGANISM: Oryza sativa japonica

<400> SEQUENCE: 22

Met Ala Ala Pro Ser Val Ala Val Asp Asn Leu Asn Pro Lys Val Leu
1               5                   10                  15

Asn Cys Glu Tyr Ala Val Arg Gly Glu Ile Val Ile His Ala Gln Arg
            20                  25                  30

Leu Gln Gln Gln Leu Gln Thr Gln Pro Gly Ser Leu Pro Phe Asp Glu
        35                  40                  45

Ile Leu Tyr Cys Asn Ile Gly Asn Pro Gln Ser Leu Gly Gln Lys Pro
    50                  55                  60

Val Thr Phe Phe Arg Glu Val Ile Ala Leu Cys Asp His Pro Cys Leu
65                  70                  75                  80

Leu Glu Lys Glu Glu Thr Lys Ser Leu Phe Ser Ala Asp Ala Ile Ser
                85                  90                  95

Arg Ala Thr Thr Ile Leu Ala Ser Ile Pro Gly Arg Ala Thr Gly Ala
            100                 105                 110

Tyr Ser His Ser Gln Gly Ile Lys Gly Leu Arg Asp Ala Ile Ala Ala
        115                 120                 125

Gly Ile Ala Ser Arg Asp Gly Tyr Pro Ala Asn Ala Asp Asp Ile Phe
    130                 135                 140

Leu Thr Asp Gly Ala Ser Pro Gly Val His Met Met Gln Leu Leu
145                 150                 155                 160

Ile Arg Asn Glu Lys Asp Gly Ile Leu Cys Pro Ile Pro Gln Tyr Pro
                165                 170                 175

Leu Tyr Ser Ala Ser Ile Ala Leu His Gly Gly Ala Leu Val Pro Tyr
            180                 185                 190

Tyr Leu Asn Glu Ser Thr Gly Trp Gly Leu Glu Ile Ser Asp Leu Lys
        195                 200                 205

Lys Gln Leu Glu Asp Ser Arg Leu Lys Gly Ile Asp Val Arg Ala Leu
    210                 215                 220

Val Val Ile Asn Pro Gly Asn Pro Thr Gly Gln Val Leu Ala Glu Glu
225                 230                 235                 240

Asn Gln Arg Asp Ile Val Lys Phe Cys Lys Asn Glu Gly Leu Val Leu
                245                 250                 255

Leu Ala Asp Glu Val Tyr Gln Glu Asn Ile Tyr Val Asp Asn Lys Lys
            260                 265                 270

Phe Asn Ser Phe Lys Lys Ile Ala Arg Ser Met Gly Tyr Asn Glu Asp
        275                 280                 285

Asp Leu Pro Leu Val Ser Phe Gln Ser Val Ser Lys Gly Tyr Tyr Gly
    290                 295                 300

Glu Cys Gly Lys Arg Gly Gly Tyr Met Glu Ile Thr Gly Phe Ser Ala
305                 310                 315                 320

Pro Val Arg Glu Gln Ile Tyr Lys Val Ala Ser Val Asn Leu Cys Ser
                325                 330                 335

Asn Ile Thr Gly Gln Ile Leu Ala Ser Leu Val Met Asn Pro Pro Lys
            340                 345                 350

Ala Gly Asp Ala Ser Tyr Ala Ser Tyr Lys Ala Glu Lys Asp Gly Ile
        355                 360                 365

Leu Gln Ser Leu Ala Arg Arg Ala Lys Ala Leu Glu Asn Ala Phe Asn

|   |   |   |   | 370 |   |   |   | 375 |   |   |   | 380 |   |
| - | - | - | - | - | - | - | - | - | - | - | - | - | - |
| Ser | Leu | Glu | Gly | Ile | Thr | Cys | Asn | Lys | Thr | Glu | Gly | Ala | Met | Tyr | Leu |
| 385 |   |   |   | 390 |   |   |   | 395 |   |   |   |   |   |   | 400 |

Phe Pro Gln Leu Ser Leu Pro Gln Lys Ala Ile Asp Ala Ala Lys Ala
               405               410               415

Ala Asn Lys Ala Pro Asp Ala Phe Tyr Ala Leu Arg Leu Leu Glu Ala
               420               425               430

Thr Gly Ile Val Val Pro Gly Ser Gly Phe Gly Gln Val Pro Gly
               435               440               445

Thr Trp His Ile Arg Cys Thr Ile Leu Pro Gln Glu Glu Lys Ile Pro
               450               455               460

Ala Ile Ile Ser Arg Phe Lys Ala Phe His Glu Gly Phe Met Ala Ala
465               470               475               480

Tyr Arg Asp

<210> SEQ ID NO 23
<211> LENGTH: 1722
<212> TYPE: DNA
<213> ORGANISM: Cyanidioschyzon merolae

<400> SEQUENCE: 23

```
atgcaacacg tgttggcggg tcgggtaggg cgtagaacgt ttgggctgct caatttcagt    60
tatctccgta tagggcgaag gaataggagc cacggtgtaa gcgcagggat gccgcacgaa   120
gccgacggga cgcgccggcg aaaagcgctc gacttgcgaa ccataaacca gcgcgtggta   180
gcggcgcagt acgctgtgcg tggtgaattg cccactcgcg ctgcgcgact gcaacagact   240
ctagaaaaag gaggaccaga agctgccgca ctgccgttta aggaaataat ttactgcaac   300
atcggaaatc cacaggcact tgggaacccg ccattcactt accaccggcg ggtcatggca   360
ctgtgcgact gtccggactt ggcagcggca ctccccgaga aggagcgtga aaaactgttc   420
cccgccgacg tgcgcgaagc gacggaacga atcctacgct ccgctggact cggcggtacg   480
ggagcgtact cggactccca gggagtgccg atcattcgac aagatgtggc agagttcatg   540
aacaagcggg acggcattca cgaggactcc gaatttgcag ctcgagtgaa ggatgtgttt   600
ttgacaaatg gttcatcgag cgcgatcctc atgctcatgg cgctgttgag cggttccgac   660
gcagcgctca gcgcggacgg taccaacggc gtatcgcatg gacgcgaaac acgttccatg   720
cgaccgggtg tgctgattcc agtgccacag tatccgattt actcggcgct ttgcacagtc   780
ctagggatcg aagcgctaca ctaccatctc gttcaggagc agaattggtc tattcaagtc   840
acggagctaa cggaacaggt tcgacaggca cgctcccgtg gcatcgaagc gcgcgccctg   900
gtcgtcatct caccggggaa tcctaccgga caattgcttc atccggcgaa catgcgagaa   960
ctgatggatt ttgcgtatcg agagggactc ctactcctgg ctgatgaggt ctatgcagac  1020
aacgtgtact tggatggtcg gaaattcgag tcgtttcgaa gagtgctgca ttcgagtatg  1080
ccggaggagg tccaggagtc gctggaactc gtgtcgctct actccgccag caaagggctt  1140
gtcgagagt gtggtcgccg cggcggctac atgctgttat caccgggcgt tacaaacgag  1200
gcacgtgaac aactcctgaa actcgctagt atcatgctct gcccaaacct cggcggacag  1260
gtcatgatcg actgtgtggt gcgcccgccg gagccgggcc aaccatcata tgagctctac  1320
cagaaagaga aacttgagcg ttatgaaagt ttgcggcgac gtgcgcatcg cgttgtagag  1380
gcatttaaga gtatgcgcgg tgtgcaatgc aaccctagtg agggcgccat gtacgccttt  1440
ccgagcatca ctgtgggcac gaaagcactc caggcagcgc aaaagtccaa tatgccgctg  1500
```

-continued

```
gatacgtttt actgtgtcag ccttttggaa cgaactggta tctgtgtggt gccgggcgca    1560
gggttcggca tgcattccaa tgaaccaaca tccagtgtcc cgaacggttc gtgtcggttt    1620
tacctgcgga cgactatttt gcctccggag gaaaagctcg aacccgtcat cgcgctgctt    1680
cgggctcatc acgaggagtt tcttcaaaag tatccccgg ac                        1722
```

<210> SEQ ID NO 24
<211> LENGTH: 574
<212> TYPE: PRT
<213> ORGANISM: Cyanidioschyzon merolae

<400> SEQUENCE: 24

```
Met Gln His Val Leu Ala Gly Arg Val Gly Arg Thr Phe Gly Leu
1               5                   10                  15

Leu Asn Phe Ser Tyr Leu Arg Ile Gly Arg Arg Asn Arg Ser His Gly
                20                  25                  30

Val Ser Ala Gly Met Pro His Glu Ala Asp Gly Thr Arg Arg Arg Lys
            35                  40                  45

Ala Leu Asp Leu Arg Thr Ile Asn Gln Arg Val Val Ala Ala Gln Tyr
        50                  55                  60

Ala Val Arg Gly Glu Leu Pro Thr Arg Ala Ala Arg Leu Gln Gln Thr
65                  70                  75                  80

Leu Glu Lys Gly Gly Pro Glu Ala Ala Ala Leu Pro Phe Lys Glu Ile
                85                  90                  95

Ile Tyr Cys Asn Ile Gly Asn Pro Gln Ala Leu Gly Asn Pro Pro Phe
            100                 105                 110

Thr Tyr His Arg Arg Val Met Ala Leu Cys Asp Cys Pro Asp Leu Ala
        115                 120                 125

Ala Ala Leu Pro Glu Lys Glu Arg Glu Lys Leu Phe Pro Ala Asp Val
    130                 135                 140

Arg Glu Ala Thr Glu Arg Ile Leu Arg Ser Ala Gly Leu Gly Gly Thr
145                 150                 155                 160

Gly Ala Tyr Ser Asp Ser Gln Gly Val Pro Ile Ile Arg Gln Asp Val
                165                 170                 175

Ala Glu Phe Met Asn Lys Arg Asp Gly Ile His Glu Asp Ser Glu Phe
            180                 185                 190

Ala Ala Arg Val Lys Asp Val Phe Leu Thr Asn Gly Ser Ser Ser Ala
        195                 200                 205

Ile Leu Met Leu Met Ala Leu Leu Ser Gly Ser Asp Ala Ala Leu Ser
    210                 215                 220

Ala Asp Gly Thr Asn Gly Val Ser His Gly Arg Glu Thr Arg Ser Met
225                 230                 235                 240

Arg Pro Gly Val Leu Ile Pro Val Pro Gln Tyr Pro Ile Tyr Ser Ala
                245                 250                 255

Leu Cys Thr Val Leu Gly Ile Glu Ala Leu His Tyr His Leu Val Gln
            260                 265                 270

Glu Gln Asn Trp Ser Ile Gln Val Thr Glu Leu Thr Glu Gln Val Arg
        275                 280                 285

Gln Ala Arg Ser Arg Gly Ile Glu Ala Arg Ala Leu Val Val Ile Ser
    290                 295                 300

Pro Gly Asn Pro Thr Gly Gln Leu Leu His Pro Ala Asn Met Arg Glu
305                 310                 315                 320

Leu Met Asp Phe Ala Tyr Arg Glu Gly Leu Leu Leu Ala Asp Glu
                325                 330                 335

Val Tyr Ala Asp Asn Val Tyr Leu Asp Gly Arg Lys Phe Glu Ser Phe
```

```
                340                 345                 350
Arg Arg Val Leu His Ser Ser Met Pro Glu Glu Val Gln Glu Ser Leu
                355                 360                 365
Glu Leu Val Ser Leu Tyr Ser Ala Ser Lys Gly Leu Val Gly Glu Cys
        370                 375                 380
Gly Arg Arg Gly Gly Tyr Met Leu Leu Ser Pro Gly Val Thr Asn Glu
385                 390                 395                 400
Ala Arg Glu Gln Leu Leu Lys Leu Ala Ser Ile Met Leu Cys Pro Asn
                405                 410                 415
Leu Gly Gly Gln Val Met Ile Asp Cys Val Val Arg Pro Pro Glu Pro
                420                 425                 430
Gly Gln Pro Ser Tyr Glu Leu Tyr Gln Lys Glu Lys Leu Glu Arg Tyr
            435                 440                 445
Glu Ser Leu Arg Arg Arg Ala His Arg Val Val Glu Ala Phe Lys Ser
        450                 455                 460
Met Arg Gly Val Gln Cys Asn Pro Ser Glu Gly Ala Met Tyr Ala Phe
465                 470                 475                 480
Pro Ser Ile Thr Val Gly Thr Lys Ala Leu Gln Ala Ala Gln Lys Ser
                485                 490                 495
Asn Met Pro Leu Asp Thr Phe Tyr Cys Val Ser Leu Leu Glu Arg Thr
                500                 505                 510
Gly Ile Cys Val Val Pro Gly Ala Gly Phe Gly Met His Ser Asn Glu
            515                 520                 525
Pro Thr Ser Ser Val Pro Asn Gly Ser Cys Arg Phe Tyr Leu Arg Thr
        530                 535                 540
Thr Ile Leu Pro Pro Glu Glu Lys Leu Glu Pro Val Ile Ala Leu Leu
545                 550                 555                 560
Arg Ala His His Glu Glu Phe Leu Gln Lys Tyr Pro Pro Asp
                565                 570

<210> SEQ ID NO 25
<211> LENGTH: 1779
<212> TYPE: DNA
<213> ORGANISM: Saccharomyces cerevisiae

<400> SEQUENCE: 25
atgttatcac tgtctgccaa aaatcacttc acagtgagta attctataac tcacgttatt    60
aagtcatatc atataaggac tctcacttca agcgcagaaa aaatgccaca tatcactact   120
ccttttccta cctcagccag tagtacaaag ttaaaagctt tcaggaaagt tagacccgtc   180
ctacagagac atagctcttc ctggattgtt gctcaaaatc atagacgttc attatctggt   240
caatcttcgc taaacgacct gcgtcatttg aatcgctttc cacaccacac gttgaaaact   300
tcgaataacg agttttatcc cgccgaacaa ttgactttgg aagacgtaaa tgaaaatgtc   360
ttgaaggcta agtacgccgt tagaggtgcc atcccaatga gagctgaaga attgaaagct   420
caactggaga aggatcctca atctctgcca tttgacagga ttatcaacgc aatattggt    480 aatcctcagc aactacaaca gaaacctctg acttactaca gacaggtctt gtctctctta   540
caatacccag aactattaaa ccaaaacgaa cagcagctag ttgattcgaa attgtttaaa   600
ctagatgcca ttaaacgtgc aaagagttta atggaagata tcggtggttc tgttggtgct   660
tactcttctt ctcaaggtgt agaaggtata aggaaaagtg tcgctgaatt tataacgaag   720
agggacgaag gcgagatatc ataccccagag gatattttcc taactgctgg tgcatccgca   780
gctgtcaatt acttgttatc aatttttctgt agagggccag aaacggggtgt cttgattcca   840
```

```
attcctcaat atccattata taccgctact ctagctttga caattctca agctttacca    900
tactatttag atgagaattc aggttggtca actaatccag aagaaattga aactgtcgtc    960
aaagaggcta tacagaacga aatcaaacct acagttctag tggttatcaa tccaggtaat   1020
cctacaggag ctgtcctatc acctgagtct atagctcaga tttttgaagt cgcagccaag   1080
tacggtacag tagtgatagc tgacgaagtt tatcaagaaa atatcttccc gggcaccaag   1140
ttccattcta tgaagaaaat tttgagacat ttacagaggg aacatccagg taaattcgat   1200
aatgttcagc tagcttcttt gcattcgact tctaagggtg tttctggtga atgtggtcaa   1260
agggtggct acatggaact cactggattc agccatgaga tgagacaagt tatcttgaaa   1320
ctagcctcga tttcattgtg tcccgttgtc acaggtcaag ctttggttga tttgatggtt   1380
cgtccaccag tggaagggga ggaatcattc gagtcggacc aagcagaacg taactccatc   1440
catgaaaagt taattacaag agcaatgaca ctgtatgaga catttaactc tttagaaggc   1500
attgaatgtc aaaagcctca aggtgccatg tatttattcc ctaagataga cttacctttc   1560
aaggcagttc aagaagctcg ccacttagag ttaactccgg atgaatttta ttgtaagaag   1620
ttgttagaat ctactggcat ttgcactgtt cccggttctg ggtttggtca agaacctggt   1680
acttaccatt taagaacaac attttttggca cctggtctgg aatggattaa gaaatgggaa   1740
agtttccata agaattttt tgaccaatac cgtgactga                            1779
```

<210> SEQ ID NO 26
<211> LENGTH: 592
<212> TYPE: PRT
<213> ORGANISM: Saccharomyces cerevisiae

<400> SEQUENCE: 26

```
Met Leu Ser Leu Ser Ala Lys Asn His Phe Thr Val Ser Asn Ser Ile
1               5                   10                  15

Thr His Val Ile Lys Ser Tyr His Ile Arg Thr Leu Thr Ser Ser Ala
            20                  25                  30

Glu Lys Met Pro His Ile Thr Thr Pro Phe Ser Thr Ala Ser Ser
        35                  40                  45

Thr Lys Leu Lys Ala Phe Arg Lys Val Arg Pro Val Leu Gln Arg His
    50                  55                  60

Ser Ser Ser Trp Ile Val Ala Gln Asn His Arg Arg Ser Leu Ser Gly
65                  70                  75                  80

Gln Ser Ser Leu Asn Asp Leu Arg His Leu Asn Arg Phe Pro His His
                85                  90                  95

Thr Leu Lys Thr Ser Asn Asn Glu Phe Tyr Pro Ala Glu Gln Leu Thr
            100                 105                 110

Leu Glu Asp Val Asn Glu Asn Val Leu Lys Ala Lys Tyr Ala Val Arg
        115                 120                 125

Gly Ala Ile Pro Met Arg Ala Glu Leu Lys Ala Gln Leu Glu Lys
    130                 135                 140

Asp Pro Gln Ser Leu Pro Phe Asp Arg Ile Ile Asn Ala Asn Ile Gly
145                 150                 155                 160

Asn Pro Gln Gln Leu Gln Gln Lys Pro Leu Thr Tyr Tyr Arg Gln Val
                165                 170                 175

Leu Ser Leu Leu Gln Tyr Pro Glu Leu Leu Asn Gln Asn Glu Gln Gln
            180                 185                 190

Leu Val Asp Ser Lys Leu Phe Lys Leu Asp Ala Ile Lys Arg Ala Lys
        195                 200                 205

Ser Leu Met Glu Asp Ile Gly Gly Ser Val Gly Ala Tyr Ser Ser Ser
```

```
                210                 215                 220
Gln Gly Val Glu Gly Ile Arg Lys Ser Val Ala Glu Phe Ile Thr Lys
225                 230                 235                 240

Arg Asp Glu Gly Glu Ile Ser Tyr Pro Glu Asp Ile Phe Leu Thr Ala
                245                 250                 255

Gly Ala Ser Ala Ala Val Asn Tyr Leu Leu Ser Ile Phe Cys Arg Gly
                260                 265                 270

Pro Glu Thr Gly Val Leu Ile Pro Ile Pro Gln Tyr Pro Leu Tyr Thr
                275                 280                 285

Ala Thr Leu Ala Leu Asn Asn Ser Gln Ala Leu Pro Tyr Tyr Leu Asp
290                 295                 300

Glu Asn Ser Gly Trp Ser Thr Asn Pro Glu Glu Ile Glu Thr Val Val
305                 310                 315                 320

Lys Glu Ala Ile Gln Asn Glu Ile Lys Pro Thr Val Leu Val Ile
                325                 330                 335

Asn Pro Gly Asn Pro Thr Gly Ala Val Leu Ser Pro Glu Ser Ile Ala
                340                 345                 350

Gln Ile Phe Glu Val Ala Ala Lys Tyr Gly Thr Val Val Ile Ala Asp
                355                 360                 365

Glu Val Tyr Gln Glu Asn Ile Phe Pro Gly Thr Lys Phe His Ser Met
370                 375                 380

Lys Lys Ile Leu Arg His Leu Gln Arg Glu His Pro Gly Lys Phe Asp
385                 390                 395                 400

Asn Val Gln Leu Ala Ser Leu His Ser Thr Ser Lys Gly Val Ser Gly
                405                 410                 415

Glu Cys Gly Gln Arg Gly Gly Tyr Met Glu Leu Thr Gly Phe Ser His
                420                 425                 430

Glu Met Arg Gln Val Ile Leu Lys Leu Ala Ser Ile Ser Leu Cys Pro
                435                 440                 445

Val Val Thr Gly Gln Ala Leu Val Asp Leu Met Val Arg Pro Pro Val
                450                 455                 460

Glu Gly Glu Glu Ser Phe Glu Ser Asp Gln Ala Glu Arg Asn Ser Ile
465                 470                 475                 480

His Glu Lys Leu Ile Thr Arg Ala Met Thr Leu Tyr Glu Thr Phe Asn
                485                 490                 495

Ser Leu Glu Gly Ile Glu Cys Gln Lys Pro Gln Gly Ala Met Tyr Leu
                500                 505                 510

Phe Pro Lys Ile Asp Leu Pro Phe Lys Ala Val Gln Glu Ala Arg His
                515                 520                 525

Leu Glu Leu Thr Pro Asp Glu Phe Tyr Cys Lys Lys Leu Leu Glu Ser
530                 535                 540

Thr Gly Ile Cys Thr Val Pro Gly Ser Gly Phe Gly Gln Glu Pro Gly
545                 550                 555                 560

Thr Tyr His Leu Arg Thr Thr Phe Leu Ala Pro Gly Leu Glu Trp Ile
                565                 570                 575

Lys Lys Trp Glu Ser Phe His Lys Glu Phe Phe Asp Gln Tyr Arg Asp
                580                 585                 590

<210> SEQ ID NO 27
<211> LENGTH: 1524
<212> TYPE: DNA
<213> ORGANISM: Saccharomyces cerevisiae

<400> SEQUENCE: 27
atgacaatga cacaccaaca ggatttgaaa ggtgtgttca ccgcaaagga tttggatttt    60
```

```
aagcccgctg gcaagattac taaaaaagat ttgaatacag gtgtcactaa ggcagaatat    120
gctgtaagag gagctattcc aaccagagct gacgagctaa agaggaatt gaaaaaaaac    180 ccagaagttt tgcctttcga tgatattatc aatgcgaaca ttggtaatcc gcagcaactg   240
gatcagaagc ctttgaccct taccaggcaa gtactggcca tcctggagta cccggaaatt   300
ttacgagtag gccataatga actggcttct tgaacttgt tttccaggga cgccttggaa    360
agagctgagc gcctcttgaa tgatattggc ggttctatag gggcatattc gcattctcaa   420
ggtgtgccag gaataaggca aacagttgct gacttcatta ctagaagaga cggcggtgag   480
cccgctacac cggaagatat ttatttaacc actggcgctt cgtccgcggc aacttctttg   540
ttatctttat tgtgtaaaga ttctcaaaca ggcctgctga ttccaattcc gcagtatccg   600
ctttatactg catccgcatc tcttttcaat gcacaagtgc tgccatacta cttagatgag   660
gagtcaaatt ggtctacaaa cagcgacgaa attgaaaaag tagtgcaaga tgcttttgaaa   720 aaacagatca gaccatctgt gctgatagtt attaatccag gtaacccaac cggtgcagtt   780
ctttctgaag aaaccattgc caggatctgt tgatcgctg cgaaatacgg cattacaatc    840
atttctgatg aggtctatca agaaaacatt ttcaacgatg ttaaatttca ttcgatgaag   900
aaagtcctaa gaaaattgca gcatctttat ccaggaaaat tcgataacgt tcagctcgcc   960
tctttacact ccatttctaa aggattcatg gatgagtgcg gccaaagagg cggttacatg  1020
gaaattattg ggttttctca agaaataaga gatgctcttt tcaaactcat gtctatatcc  1080
atatgttctg ttgtcacagg acaagctgtg gttgatttaa tggtcaaacc accccagcct  1140
ggagacgagt cctatgaaca agatcatgac gaaaggctga aaatttttca tgaaatgcgt  1200
acgagagcaa acttattgta cgagacgttt aaggaactag agggtatcga atgccaaaaa  1260
cctcagggtg caatgtatct tttccctagg cttgttttac ctaagaaagc tctttgtgaa  1320
agcgaacgcc ttggcatcga acctgatgag ttctattgca catctttgct agaatctaca  1380
ggtatttgta ctgtcccagg gtctgggttc ggacaaagac ccgggactta tcatgtgcga  1440
acaacgtttt tggctccagg gactaaatgg attcaagact ggaaagaatt tcatcaagat  1500
ttcttcagca agtatcgtaa ttga                                         1524
```

<210> SEQ ID NO 28
<211> LENGTH: 507
<212> TYPE: PRT
<213> ORGANISM: Saccharomyces cerevisiae

<400> SEQUENCE: 28

```
Met Thr Met Thr His Gln Gln Asp Leu Lys Gly Val Phe Thr Ala Lys
1               5                   10                  15

Asp Leu Asp Phe Lys Pro Ala Gly Lys Ile Thr Lys Lys Asp Leu Asn
            20                  25                  30

Thr Gly Val Thr Lys Ala Glu Tyr Ala Val Arg Gly Ala Ile Pro Thr
        35                  40                  45

Arg Ala Asp Glu Leu Lys Glu Glu Leu Lys Lys Asn Pro Glu Val Leu
    50                  55                  60

Pro Phe Asp Asp Ile Ile Asn Ala Asn Ile Gly Asn Pro Gln Gln Leu
65                  70                  75                  80

Asp Gln Lys Pro Leu Thr Phe Thr Arg Gln Val Leu Ala Ile Leu Glu
                85                  90                  95

Tyr Pro Glu Ile Leu Arg Val Gly His Asn Glu Leu Ala Ser Leu Asn
            100                 105                 110
```

Leu Phe Ser Arg Asp Ala Leu Glu Arg Ala Glu Arg Leu Leu Asn Asp
         115                 120                 125

Ile Gly Gly Ser Ile Gly Ala Tyr Ser His Ser Gln Gly Val Pro Gly
130                 135                 140

Ile Arg Gln Thr Val Ala Asp Phe Ile Thr Arg Arg Asp Gly Gly Glu
145                 150                 155                 160

Pro Ala Thr Pro Glu Asp Ile Tyr Leu Thr Gly Ala Ser Ser Ala
                165                 170                 175

Ala Thr Ser Leu Leu Ser Leu Leu Cys Lys Asp Ser Gln Thr Gly Leu
                180                 185                 190

Leu Ile Pro Ile Pro Gln Tyr Pro Leu Tyr Thr Ala Ser Ala Ser Leu
            195                 200                 205

Phe Asn Ala Gln Val Leu Pro Tyr Tyr Leu Asp Glu Glu Ser Asn Trp
210                 215                 220

Ser Thr Asn Ser Asp Glu Ile Glu Lys Val Val Gln Asp Ala Leu Lys
225                 230                 235                 240

Lys Gln Ile Arg Pro Ser Val Leu Ile Val Ile Asn Pro Gly Asn Pro
                245                 250                 255

Thr Gly Ala Val Leu Ser Glu Glu Thr Ile Ala Arg Ile Cys Leu Ile
            260                 265                 270

Ala Ala Lys Tyr Gly Ile Thr Ile Ile Ser Asp Glu Val Tyr Gln Glu
        275                 280                 285

Asn Ile Phe Asn Asp Val Lys Phe His Ser Met Lys Lys Val Leu Arg
    290                 295                 300

Lys Leu Gln His Leu Tyr Pro Gly Lys Phe Asp Asn Val Gln Leu Ala
305                 310                 315                 320

Ser Leu His Ser Ile Ser Lys Gly Phe Met Asp Glu Cys Gly Gln Arg
                325                 330                 335

Gly Gly Tyr Met Glu Ile Ile Gly Phe Ser Gln Glu Ile Arg Asp Ala
            340                 345                 350

Leu Phe Lys Leu Met Ser Ile Ser Ile Cys Ser Val Val Thr Gly Gln
        355                 360                 365

Ala Val Val Asp Leu Met Val Lys Pro Pro Gln Pro Gly Asp Glu Ser
    370                 375                 380

Tyr Glu Gln Asp His Asp Glu Arg Leu Lys Ile Phe His Glu Met Arg
385                 390                 395                 400

Thr Arg Ala Asn Leu Leu Tyr Glu Thr Phe Lys Glu Leu Glu Gly Ile
                405                 410                 415

Glu Cys Gln Lys Pro Gln Gly Ala Met Tyr Leu Phe Pro Arg Leu Val
            420                 425                 430

Leu Pro Lys Lys Ala Leu Cys Glu Ser Glu Arg Leu Gly Ile Glu Pro
        435                 440                 445

Asp Glu Phe Tyr Cys Thr Ser Leu Leu Glu Ser Thr Gly Ile Cys Thr
    450                 455                 460

Val Pro Gly Ser Gly Phe Gly Gln Arg Pro Gly Thr Tyr His Val Arg
465                 470                 475                 480

Thr Thr Phe Leu Ala Pro Gly Thr Lys Trp Ile Gln Asp Trp Lys Glu
                485                 490                 495

Phe His Gln Asp Phe Phe Ser Lys Tyr Arg Asn
            500                 505

<210> SEQ ID NO 29
<211> LENGTH: 1566
<212> TYPE: DNA
<213> ORGANISM: Ashbya gossypii

<400> SEQUENCE: 29

```
atggcaatag ggatgctgag aagaaatagc agcggcaccg ccgtgagcgt tctacagggg      60
cgtgtgcttc gcactcgtag attgagctca gtaaaggacg ggtcgcggtt tgtgcctgcg     120
gaaccgatga cactagcgga cgtgaacgaa acgtggtca  aggcgaagta cgcggtgcgg     180
gggaagattc caacgcgtgc agaggagctg gagcggcggc tggaggagca cccgggctcg     240
ctgccgttca gcaaaatcat ccaagcgaac atcggcaatc cgcagcagct gggccagaag     300
ccgctgacat tctaccggca agtgatctcg ctgatgcaga tccacagtt  gctggagatg     360
cccgcagaat ggctgcagca ggcgttcaag gcggatgtgg tggtgcgtgc gcggaggatg     420
ctgcaggacg ccggaggctc cgtgggagcg tactcggcgt cgcagggtgt gaaaggctac     480
cggcgcacgg ttgcgcagtt tattgagcgg cgcgatggga tcccagcgaa tccagacaac     540
gtgtacctga ccgcgggtgc gtcctctgct gtgtcttgtc tgctgtcgac attctgcaag     600
ggaccggaga caggcgtgtt gatcccaatc cctcagtacc cgctgtacac tgctacgatc     660
acacagaata acgcggttgc gctgccgtac tacctaaatg aggctgatgg gtggtctacg     720
aatccagatg agatggaacg tgtcatcctc gattctaaga gaggaacat  cgcgcccaaa     780
tgtctggttg tgattaaccc tgggaatccc actggttccg tactgtctgt aaaggatatg     840
gaggctattc taaacacttgc tgcgaagtat gggattgtcg ttattgcgga cgaggtatac     900
caggataatg tgtttggcga tgccaagttc cactctatgc gtaaggtgct gaaaaacctt     960
caactcagag agccaacgct ctacaagaat gtccagttag cctctcttca ctcgatctcg    1020
aaggggctct ccggcgaatg tggccagcgt ggtggctaca tggaattgat cggtttccgt    1080
gaggagctca ggaaggtttt cgttaagttg gcttctatat ctctttgtcc agtggttacc    1140
ggacaagctc tagtcgacct tatggttggg cctcccagcc aaggggatcc atcctatgag    1200
caatataccc aggaaacaag gagtatctat cacgaattgg aggaacggtc gcaactgctg    1260
tggaaaacgt tctgttcctt ggagggtata gaatgcaata tgccacaagg tgctctatat    1320
ctattcccta gttgcatct  tccacagaaa gctattgaag cggcgcaaaa gctgggtata    1380
ccagcggatg agctctactg tagcgaatta cttgatgaaa caggcatctg cactgtccct    1440
ggaactggtt tcggccaaat cccgggcaca tatcacgtta gaactacgtt tttgccacct    1500
ggtactaagt ggatcgaaag ttggaaggac ttccacaaga aattttatga caagtatagg    1560
gactaa                                                                1566
```

<210> SEQ ID NO 30
<211> LENGTH: 521
<212> TYPE: PRT
<213> ORGANISM: Ashbya gossypii

<400> SEQUENCE: 30

```
Met Ala Ile Gly Met Leu Arg Arg Asn Ser Ser Gly Thr Ala Val Ser
1               5                   10                  15

Val Leu Gln Gly Arg Val Leu Arg Thr Arg Arg Leu Ser Ser Val Lys
            20                  25                  30

Asp Gly Ser Arg Phe Val Pro Ala Glu Pro Met Thr Leu Ala Asp Val
        35                  40                  45

Asn Glu Asn Val Val Lys Ala Lys Tyr Ala Val Arg Gly Lys Ile Pro
    50                  55                  60

Thr Arg Ala Glu Glu Leu Glu Arg Arg Leu Glu Glu His Pro Gly Ser
65                  70                  75                  80
```

-continued

```
Leu Pro Phe Ser Lys Ile Ile Gln Ala Asn Ile Gly Asn Pro Gln Gln
                 85                  90                  95

Leu Gly Gln Lys Pro Leu Thr Phe Tyr Arg Gln Val Ile Ser Leu Met
            100                 105                 110

Gln Asn Pro Gln Leu Leu Glu Met Pro Ala Glu Trp Leu Gln Gln Ala
        115                 120                 125

Phe Lys Ala Asp Val Val Arg Ala Arg Met Leu Gln Asp Ala
    130                 135                 140

Gly Gly Ser Val Gly Ala Tyr Ser Ala Ser Gln Gly Val Lys Gly Tyr
145                 150                 155                 160

Arg Arg Thr Val Ala Gln Phe Ile Glu Arg Arg Asp Gly Ile Pro Ala
                165                 170                 175

Asn Pro Asp Asn Val Tyr Leu Thr Ala Gly Ala Ser Ser Ala Val Ser
            180                 185                 190

Cys Leu Leu Ser Thr Phe Cys Lys Gly Pro Glu Thr Gly Val Leu Ile
            195                 200                 205

Pro Ile Pro Gln Tyr Pro Leu Tyr Thr Ala Thr Ile Thr Gln Asn Asn
210                 215                 220

Ala Val Ala Leu Pro Tyr Tyr Leu Asn Glu Ala Asp Gly Trp Ser Thr
225                 230                 235                 240

Asn Pro Asp Glu Met Glu Arg Val Ile Leu Asp Ser Lys Lys Arg Asn
                245                 250                 255

Ile Ala Pro Lys Cys Leu Val Val Ile Asn Pro Gly Asn Pro Thr Gly
                260                 265                 270

Ser Val Leu Ser Val Lys Asp Met Glu Ala Ile Leu Thr Leu Ala Ala
            275                 280                 285

Lys Tyr Gly Ile Val Val Ile Ala Asp Glu Val Tyr Gln Asp Asn Val
290                 295                 300

Phe Gly Asp Ala Lys Phe His Ser Met Arg Lys Val Leu Lys Asn Leu
305                 310                 315                 320

Gln Leu Arg Glu Pro Thr Leu Tyr Lys Asn Val Gln Leu Ala Ser Leu
                325                 330                 335

His Ser Ile Ser Lys Gly Leu Ser Gly Glu Cys Gly Gln Arg Gly Gly
            340                 345                 350

Tyr Met Glu Leu Ile Gly Phe Arg Glu Glu Leu Arg Lys Val Phe Val
            355                 360                 365

Lys Leu Ala Ser Ile Ser Leu Cys Pro Val Val Thr Gly Gln Ala Leu
370                 375                 380

Val Asp Leu Met Val Gly Pro Pro Ser Gln Gly Asp Pro Ser Tyr Glu
385                 390                 395                 400

Gln Tyr Thr Gln Glu Thr Arg Ser Ile Tyr His Glu Leu Glu Glu Arg
                405                 410                 415

Ser Gln Leu Leu Trp Lys Thr Phe Cys Ser Leu Glu Gly Ile Glu Cys
            420                 425                 430

Asn Met Pro Gln Gly Ala Leu Tyr Leu Phe Pro Lys Leu His Leu Pro
        435                 440                 445

Gln Lys Ala Ile Glu Ala Ala Gln Lys Leu Gly Ile Pro Ala Asp Glu
    450                 455                 460

Leu Tyr Cys Ser Glu Leu Leu Asp Glu Thr Gly Ile Cys Thr Val Pro
465                 470                 475                 480

Gly Thr Gly Phe Gly Gln Ile Pro Gly Thr Tyr His Val Arg Thr Thr
                485                 490                 495

Phe Leu Pro Pro Gly Thr Lys Trp Ile Glu Ser Trp Lys Asp Phe His
            500                 505                 510
```

Lys Lys Phe Tyr Asp Lys Tyr Arg Asp
        515                 520

<210> SEQ ID NO 31
<211> LENGTH: 1563
<212> TYPE: DNA
<213> ORGANISM: Candida albicans

<400> SEQUENCE: 31

| | | | | | |
|---|---|---|---|---|---|
| atgcttagag | taaattcacg | attattaact | actcgaaaat | ctcaatttat | gttcacttct | 60 |
| aattccttaa | ggttttagc | aacctttaaa | cctgcggatc | cattgactac | tcatgatatc | 120 |
| aacccacaaa | cggtcgaggc | aaaatacgct | gtacgtggga | aaatcccaat | tattgccgat | 180 |
| gaattgaatg | aattgattca | aaagcaacca | cagctgcatg | gattaccatt | tagcaaaatc | 240 |
| attaatgcca | acattggtaa | cccacagcaa | ttggaacaac | gtccattgac | atggtatcgt | 300 |
| caagtattgt | ctcttttaca | atacccggat | ttattgaaaa | atggagaccc | tgaaaccgtt | 360 |
| aaatcacttt | atcctgaaga | tgtgattgag | cgagcacaat | caattttgaa | acacattgga | 420 |
| tcaataggg | catactctca | ttctcagggt | gccagttatt | ccgacaatc | tattgctgaa | 480 |
| tttataacta | accgtgatgg | tggttatgta | tcccacgcca | acaacatttt | tttaacttcc | 540 |
| ggggcatcaa | ctgcagtgtc | gtatttatta | caaattttgt | ctgtcaatga | aaactccggg | 600 |
| ttcttaattc | cgatcccaca | gtatcctttg | tatactgcca | ctattgcctt | gaataatgcc | 660 |
| aagccaattg | ttattatct | cgatgagtcg | aaccattggt | caaccaatcc | tcaagagatt | 720 |
| agagaattga | tcgaaaccaa | tcaactgcaa | ggtattaaca | tcaaggcatt | ggtggtgatt | 780 |
| aacccgggga | acccaacggg | ggcaatttta | tcatcacaag | ataattga | attgatagat | 840 |
| attgctgctg | aatatggaat | tgtattaatt | gccgatgagg | tttatcaaga | aaatattttc | 900 |
| aaagggaaat | ttgtttcatt | caagaagatt | ttgtcggaat | taattgagca | agaccctcaa | 960 |
| acttataaac | atgttcaatt | agcatcatta | cactcgacat | cgaaaggtgt | tagtggagaa | 1020 |
| tgtggacaac | gtggtggata | tatgaatta | gttgggttca | aaccggaagt | taaagatgtg | 1080 |
| gttttcaaat | tggcatcgat | taatttatgt | tctgttgtct | ctggtcaagc | attaatggag | 1140 |
| ttaatgatta | tcctcctca | agaaggtgat | cctagttacc | ccttgtacaa | agcgaaacc | 1200 |
| gaatcaatcc | ataacgattt | ggaatcaaga | gcagaatcac | tctatcaagc | ttttttacaa | 1260 |
| atggaagata | tcaaatgtaa | taaaccaatg | ggggccatgt | atattttccc | cactttagat | 1320 |
| tttgatccag | cccgatacca | taagttatat | tcgagagcta | agaattccaa | tttacaaatt | 1380 |
| gatgatatt | attgtatcga | gttattagaa | ggtacaggta | tttgttgtgt | tcctggtaat | 1440 |
| ggatttggtc | agaaaccaga | tacttatcat | ttaagaacaa | cattttttacc | accaggtaaa | 1500 |
| gaatggattg | ataaatggat | aaatttccat | aaatcattta | ttaaaaaata | taagatgaa | 1560 |
| tag | | | | | | 1563 |

<210> SEQ ID NO 32
<211> LENGTH: 520
<212> TYPE: PRT
<213> ORGANISM: Candida albicans

<400> SEQUENCE: 32

Met Leu Arg Val Asn Ser Arg Leu Leu Thr Thr Arg Lys Ser Gln Phe
1               5                   10                  15

Met Phe Thr Ser Asn Ser Leu Arg Phe Leu Ala Thr Phe Lys Pro Ala
            20                  25                  30

-continued

```
Asp Pro Leu Thr Thr His Asp Ile Asn Pro Gln Thr Val Glu Ala Lys
        35                  40                  45

Tyr Ala Val Arg Gly Lys Ile Pro Ile Ala Asp Glu Leu Asn Glu
 50                  55                  60

Leu Ile Gln Lys Gln Pro Gln Ser His Gly Leu Pro Phe Ser Lys Ile
 65                  70                  75                  80

Ile Asn Ala Asn Ile Gly Asn Pro Gln Gln Leu Glu Gln Arg Pro Leu
                 85                  90                  95

Thr Trp Tyr Arg Gln Val Leu Ser Leu Leu Gln Tyr Pro Asp Leu Leu
                100                 105                 110

Lys Asn Gly Asp Pro Glu Thr Val Lys Ser Leu Tyr Pro Glu Asp Val
                115                 120                 125

Ile Glu Arg Ala Gln Ser Ile Leu Lys His Ile Gly Ser Ile Gly Ala
            130                 135                 140

Tyr Ser His Ser Gln Gly Ala Ser Tyr Phe Arg Gln Ser Ile Ala Glu
145                 150                 155                 160

Phe Ile Thr Asn Arg Asp Gly Gly Tyr Val Ser His Ala Asn Asn Ile
                165                 170                 175

Phe Leu Thr Ser Gly Ala Ser Thr Ala Val Ser Tyr Leu Leu Gln Ile
                180                 185                 190

Leu Ser Val Asn Glu Asn Ser Gly Phe Leu Ile Pro Ile Pro Gln Tyr
                195                 200                 205

Pro Leu Tyr Thr Ala Thr Ile Ala Leu Asn Asn Ala Lys Pro Ile Gly
210                 215                 220

Tyr Tyr Leu Asp Glu Ser Asn His Trp Ser Thr Asn Pro Gln Glu Ile
225                 230                 235                 240

Arg Glu Leu Ile Glu Thr Asn Gln Ser Gln Gly Ile Asn Ile Lys Ala
                245                 250                 255

Leu Val Val Ile Asn Pro Gly Asn Pro Thr Gly Ala Ile Leu Ser Ser
                260                 265                 270

Gln Asp Ile Ile Glu Leu Ile Asp Ile Ala Ala Glu Tyr Gly Ile Val
            275                 280                 285

Leu Ile Ala Asp Glu Val Tyr Gln Glu Asn Ile Phe Lys Gly Lys Phe
290                 295                 300

Val Ser Phe Lys Lys Ile Leu Ser Glu Leu Ile Glu Gln Asp Pro Gln
305                 310                 315                 320

Thr Tyr Lys His Val Gln Leu Ala Ser Leu His Ser Thr Ser Lys Gly
                325                 330                 335

Val Ser Gly Glu Cys Gly Gln Arg Gly Gly Tyr Met Glu Leu Val Gly
                340                 345                 350

Phe Lys Pro Glu Val Lys Asp Val Val Phe Lys Leu Ala Ser Ile Asn
                355                 360                 365

Leu Cys Ser Val Val Ser Gly Gln Ala Leu Met Glu Leu Met Ile Asn
370                 375                 380

Pro Pro Gln Glu Gly Asp Pro Ser Tyr Pro Leu Tyr Lys Ser Glu Thr
385                 390                 395                 400

Glu Ser Ile His Asn Asp Leu Glu Ser Arg Ala Glu Ser Leu Tyr Gln
                405                 410                 415

Ala Phe Leu Gln Met Glu Asp Ile Lys Cys Asn Lys Pro Met Gly Ala
            420                 425                 430

Met Tyr Ile Phe Pro Thr Leu Asp Phe Asp Pro Ala Arg Tyr His Lys
                435                 440                 445

Leu Tyr Ser Arg Ala Lys Asn Ser Asn Leu Gln Ile Asp Asp Ile Tyr
450                 455                 460
```

```
Cys Ile Glu Leu Leu Glu Gly Thr Gly Ile Cys Cys Val Pro Gly Asn
465                 470                 475                 480

Gly Phe Gly Gln Lys Pro Asp Thr Tyr His Leu Arg Thr Thr Phe Leu
            485                 490                 495

Pro Pro Gly Lys Glu Trp Ile Asp Lys Trp Ile Asn Phe His Lys Ser
        500                 505                 510

Phe Ile Lys Lys Tyr Lys Asp Glu
        515                 520

<210> SEQ ID NO 33
<211> LENGTH: 1518
<212> TYPE: DNA
<213> ORGANISM: Schizosaccharomyces pombe

<400> SEQUENCE: 33
atgtttacag attatccaaa tgatattaac tgtgagtctc caagaatgtc ggaccttgat      60
ggattttgtc aaaatgcgtt ctcagacctt aattctttga tcaacaagt atttaaggca     120
aattacgccg tccgtggagc tttagccatt cttgcggacg agatccaaga tgatttactt     180
gaaaatcctt cttcatatcc tttcagtgag atcgtctatg caaacatcgg taatcctcag     240
cagatgggac agtctcctat tacattcgtt cgacaggttt atctctttg ccagtaccct      300
accttgttag accatgctga ggaaaagtgg tttcaaaatt gttccctac ggatgtcgta      360
caacgatcca aaatgctctt aaaggaatct ggaagtttgg gtgcctatag tgcttctcaa     420
ggtattccgc ttgtaaggcg acatgttgcg gatttcatta gagcgagaga tggatttgat     480
tgcgagccat ctgacatata tttgactagt ggtgcctcac acgctgcccg gcttataatg     540
actttgataa tcgctaggcc aacagatggt gtaatggttc ccgctcctca atatcctttg     600
tacggtgccc aaattgatct catgagtgga tctatggtat cttacagcct ctccgaggaa     660
aataattggg acattgattt tgaccaattt aaaaaatcat ttgatgaagc atctaaaaaa     720
ggtatcaacg ttcgtttatg cgtggttatt aatcccggta atcctactgg agcttgcatt     780
tctgaaaata gcatggaaaa agttttgcgc tttgctaagg caaagggcat agtattgctt     840
gccgacgaag tctatcaaaa caatatttac caaaacaagt ttcattcttt taggagaaaa     900
cttggtgaat aagagaaaaa ggaacccgac aatcattggg accaagtttc gcttatttcc     960
gtaaattctg ttagcaaagg tcaatttggt gaatgtggtc aaagaggtgg atatttggac    1020
gttgttaata ttccagagcc cgctaaggat caaatcctca aactagctac cattgacatt    1080
tgtccaccag ttgctggtca attattagta gacatgctag taaatcctcc taaacctggt    1140
gatcccagtt atgatttgtt catcaaagaa gttgatgaga ttcatgaagc actgcgttta    1200
caatgccgtc agctctacga gggaacaaag cgcatgaaga gagtttcatg tttagaaccc    1260
cacggggcca tgtatttgca tcccagcgtc tcacttcccg aaaagttaat cactacagcc    1320
aaagctcaga aaattcaacc tgacgaattc tatgcgatag aattgcttaa gcgttcaggt    1380
atatgtgttg ttcctggaag tggatttggg caaccagaag gtgattatca tattcgaatc    1440
acgtttttgg ctaaaggaac tgaatacatt gaacgatttg tcaaagctca taatgaaata    1500
atggacctct atgaataa                                                  1518

<210> SEQ ID NO 34
<211> LENGTH: 505
<212> TYPE: PRT
<213> ORGANISM: Schizosaccharomyces pombe

<400> SEQUENCE: 34
```

-continued

```
Met Phe Thr Asp Tyr Pro Asn Asp Ile Asn Cys Glu Ser Pro Arg Met
1               5                   10                  15

Ser Asp Leu Asp Gly Phe Cys Gln Asn Ala Phe Ser Asp Leu Asn Ser
            20                  25                  30

Leu Asn Gln Gln Val Phe Lys Ala Asn Tyr Ala Val Arg Gly Ala Leu
        35                  40                  45

Ala Ile Leu Ala Asp Glu Ile Gln Asp Leu Leu Glu Asn Pro Ser
    50                  55                  60

Ser Tyr Pro Phe Ser Glu Ile Val Tyr Ala Asn Ile Gly Asn Pro Gln
65              70                  75                  80

Gln Met Gly Gln Ser Pro Ile Thr Phe Val Arg Gln Val Leu Ser Leu
                85                  90                  95

Cys Gln Tyr Pro Thr Leu Leu Asp His Ala Glu Glu Lys Trp Phe Gln
                100                 105                 110

Asn Leu Phe Pro Thr Asp Val Val Gln Arg Ser Lys Met Leu Leu Lys
                115                 120                 125

Glu Ser Gly Ser Leu Gly Ala Tyr Ser Ala Ser Gln Gly Ile Pro Leu
    130                 135                 140

Val Arg Arg His Val Ala Asp Phe Ile Arg Ala Arg Asp Gly Phe Asp
145                 150                 155                 160

Cys Glu Pro Ser Asp Ile Tyr Leu Thr Ser Gly Ala Ser His Ala Ala
                165                 170                 175

Arg Leu Ile Met Thr Leu Ile Ile Ala Arg Pro Thr Asp Gly Val Met
                180                 185                 190

Val Pro Ala Pro Gln Tyr Pro Leu Tyr Gly Ala Gln Ile Asp Leu Met
        195                 200                 205

Ser Gly Ser Met Val Ser Tyr Ser Leu Ser Glu Asn Asn Trp Asp
    210                 215                 220

Ile Asp Phe Asp Gln Phe Lys Lys Ser Phe Asp Glu Ala Ser Lys Lys
225                 230                 235                 240

Gly Ile Asn Val Arg Leu Cys Val Val Ile Asn Pro Gly Asn Pro Thr
                245                 250                 255

Gly Ala Cys Ile Ser Glu Asn Ser Met Glu Lys Val Leu Arg Phe Ala
                260                 265                 270

Lys Ala Lys Gly Ile Val Leu Leu Ala Asp Glu Val Tyr Gln Asn Asn
            275                 280                 285

Ile Tyr Gln Asn Lys Phe His Ser Phe Arg Arg Lys Leu Gly Glu Leu
    290                 295                 300

Arg Glu Lys Glu Pro Asp Asn His Trp Asp Gln Val Ser Leu Ile Ser
305                 310                 315                 320

Val Asn Ser Val Ser Lys Gly Gln Phe Gly Glu Cys Gly Gln Arg Gly
                325                 330                 335

Gly Tyr Leu Asp Val Val Asn Ile Pro Glu Pro Ala Lys Asp Gln Ile
            340                 345                 350

Leu Lys Leu Ala Thr Ile Asp Ile Cys Pro Pro Val Ala Gly Gln Leu
        355                 360                 365

Leu Val Asp Met Leu Val Asn Pro Pro Lys Pro Gly Asp Pro Ser Tyr
    370                 375                 380

Asp Leu Phe Ile Lys Glu Val Asp Glu Ile His Glu Ala Leu Arg Leu
385                 390                 395                 400

Gln Cys Arg Gln Leu Tyr Glu Gly Thr Lys Arg Met Lys Arg Val Ser
                405                 410                 415

Cys Leu Glu Pro His Gly Ala Met Tyr Leu His Pro Ser Val Ser Leu
```

```
                420            425            430
Pro Glu Lys Leu Ile Thr Thr Ala Lys Ala Gln Lys Ile Gln Pro Asp
            435                440                445

Glu Phe Tyr Ala Ile Glu Leu Leu Lys Arg Ser Gly Ile Cys Val Val
    450                455                460

Pro Gly Ser Gly Phe Gly Gln Pro Glu Gly Asp Tyr His Ile Arg Ile
465                470                475                480

Thr Phe Leu Ala Lys Gly Thr Glu Tyr Ile Glu Arg Phe Val Lys Ala
                485                490                495

His Asn Glu Ile Met Asp Leu Tyr Glu
            500                505

<210> SEQ ID NO 35
<211> LENGTH: 1500
<212> TYPE: DNA
<213> ORGANISM: Aspergillus nidulans

<400> SEQUENCE: 35
atgacgaccc gaacgacagt tcctaatgcc tcgcaacgcg ctctatccac tgcggctgtt      60
cgttgcctga ccctagacaa catcaattcg aacgtcaagg ctgccaagta tgctgttcgt     120
ggagaactcg ccgttaaggc ggaggaatac cgtgtgaggc tggctcaggg agacaagaca     180
ctgccgtttg acagcgttat tttcgccaac atcggcaatc tcagcagct cgaccaaaag      240 cccatcactt tcttccgtca gtcctcagt cttatggaaa accctctact gttaagcaac      300
aaagatgccc ttcgtacgtc tttcggctat caggatgatg ttatcgagcg ggccgagaag     360
cttctggccg aagtccagag tgttggtgca tacagtcaca gccaaggtgc tcccctgatt     420
cgcgagagtg tggccaagtt cattgaagaa cgtgatggct ccccgccga ccctcagtcg      480 ctttacctta ctggtggtgc ctcttccggt gtaaacacca ttctgaacgt catttgtaat     540
gggccaaatg ctggtgtcct agttccgatt ccccagtatc tctgtacac agccacttta     600 tccctcttga atgctcagtg tgttccttac cacttagaag agcagaaggc ttggggtacc     660
gacatcggta caatcaagaa gtcattgaa caggccaagg ctgcaggcac tgacgttcgc     720
gccattgttg ttatcaaccc tggcaaccgc acgggcgctt ctttgagtcc agctgatatc     780
aagagcgtcc ttgacatcgc cgcggaagag aagctcgtcg taattgcgga cgaggtatac     840
cagacaaatg tgtttatcgg agaattcaca tcgttcaaaa agaggctccg ggagctgcag     900
caagaagtac ctggtaaata cgacaatgtc gagcttgttt cccttcacag tacttccaag     960
ggtatggttg gtgaatgtgg ccatcgcgga ggttacttcg aactggttgg atttgatccc    1020
ttggttgctg cccaggtcta caagttcatc agcatcatgc tctgccctcc tgtcatcggg    1080
caatgtttgg ttgaactgat ggtgaaccct ccaaaggagg cgagcccag ccatgagttg     1140 tatcagaagg agtacaacgg catccgggaa ggactcgcc agcgcgcctt tgccctctat     1200
gaagcttttc aacggatgga gggtgtcgag tgccaagagc tcagggtgc catgtacctt     1260 ttccctacta tctcactgcc tcccaaggct attgaagccg ctgccgctga aaccgcgcc     1320 gcagacgaat tctactgcct ccgtctcctt gacgccactg tgtttgcgt cgtccctggc     1380 tccggcttcg gtcagaagga gaacacgctc cacttccgca ctactttcct cgcaccaggc     1440
acggactggg tggagcgtat cgtgaagttc cattccgagt tcatggccaa atacaaatag     1500

<210> SEQ ID NO 36
<211> LENGTH: 499
<212> TYPE: PRT
<213> ORGANISM: Aspergillus nidulans
```

<400> SEQUENCE: 36

```
Met Thr Thr Arg Thr Thr Val Pro Asn Ala Ser Gln Arg Ala Leu Ser
1               5                   10                  15

Thr Ala Ala Val Arg Cys Leu Thr Leu Asp Asn Ile Asn Ser Asn Val
            20                  25                  30

Lys Ala Ala Lys Tyr Ala Val Arg Gly Glu Leu Ala Val Lys Ala Glu
        35                  40                  45

Glu Tyr Arg Val Arg Leu Ala Gln Gly Asp Lys Thr Leu Pro Phe Asp
    50                  55                  60

Ser Val Ile Phe Ala Asn Ile Gly Asn Pro Gln Gln Leu Asp Gln Lys
65                  70                  75                  80

Pro Ile Thr Phe Phe Arg Gln Val Leu Ser Leu Met Glu Asn Pro Leu
                85                  90                  95

Leu Leu Ser Asn Lys Asp Ala Leu Arg Thr Ser Phe Gly Tyr Gln Asp
            100                 105                 110

Asp Val Ile Glu Arg Ala Glu Lys Leu Leu Ala Glu Val Gln Ser Val
        115                 120                 125

Gly Ala Tyr Ser His Ser Gln Gly Ala Pro Leu Ile Arg Glu Ser Val
130                 135                 140

Ala Lys Phe Ile Glu Glu Arg Asp Gly Phe Pro Ala Asp Pro Gln Ser
145                 150                 155                 160

Leu Tyr Leu Thr Gly Gly Ala Ser Ser Gly Val Asn Thr Ile Leu Asn
                165                 170                 175

Val Ile Cys Asn Gly Pro Asn Ala Gly Val Leu Val Pro Ile Pro Gln
            180                 185                 190

Tyr Pro Leu Tyr Thr Ala Thr Leu Ser Leu Leu Asn Ala Gln Cys Val
        195                 200                 205

Pro Tyr His Leu Glu Glu Gln Lys Ala Trp Gly Thr Asp Ile Gly Thr
    210                 215                 220

Ile Lys Lys Ser Leu Glu Gln Ala Lys Ala Ala Gly Thr Asp Val Arg
225                 230                 235                 240

Ala Ile Val Val Ile Asn Pro Gly Asn Pro Thr Gly Ala Ser Leu Ser
                245                 250                 255

Pro Ala Asp Ile Lys Ser Val Leu Asp Ile Ala Ala Glu Glu Lys Leu
            260                 265                 270

Val Val Ile Ala Asp Glu Val Tyr Gln Thr Asn Val Phe Ile Gly Glu
        275                 280                 285

Phe Thr Ser Phe Lys Lys Arg Leu Arg Glu Leu Gln Glu Val Pro
    290                 295                 300

Gly Lys Tyr Asp Asn Val Glu Leu Val Ser Leu His Ser Thr Ser Lys
305                 310                 315                 320

Gly Met Val Gly Glu Cys Gly His Arg Gly Gly Tyr Phe Glu Leu Val
                325                 330                 335

Gly Phe Asp Pro Leu Val Ala Ala Gln Val Tyr Lys Phe Ile Ser Ile
            340                 345                 350

Met Leu Cys Pro Pro Val Ile Gly Gln Cys Leu Val Glu Leu Met Val
        355                 360                 365

Asn Pro Pro Lys Glu Gly Glu Pro Ser His Glu Leu Tyr Gln Lys Glu
370                 375                 380

Tyr Asn Gly Ile Arg Glu Gly Leu Arg Gln Arg Ala Phe Ala Leu Tyr
                385                 390                 395                 400

Glu Ala Phe Gln Arg Met Glu Gly Val Glu Cys Gln Glu Pro Gln Gly
                405                 410                 415
```

Ala Met Tyr Leu Phe Pro Thr Ile Ser Leu Pro Pro Lys Ala Ile Glu
            420                 425                 430

Ala Ala Ala Ala Glu Asn Arg Ala Ala Asp Glu Phe Tyr Cys Leu Arg
        435                 440                 445

Leu Leu Asp Ala Thr Gly Val Cys Val Val Pro Gly Ser Gly Phe Gly
    450                 455                 460

Gln Lys Glu Asn Thr Leu His Phe Arg Thr Thr Phe Leu Ala Pro Gly
465                 470                 475                 480

Thr Asp Trp Val Glu Arg Ile Val Lys Phe His Ser Glu Phe Met Ala
                485                 490                 495

Lys Tyr Lys

<210> SEQ ID NO 37
<211> LENGTH: 1506
<212> TYPE: DNA
<213> ORGANISM: Aspergillus fumigatus

<400> SEQUENCE: 37

```
atgatcacag aacccaccat gaccgtgcca tataccacca agcggaccgc ttctgatctc      60
ggccctcgtc gtctccgtgc cgataatatc aatcccaacg tcaaggcggc caagtatgct     120
gtccgtggtg agcttgccgt caaggcggag gaataccgtg tgagattggc caagggagac     180
aagtctttgc cctttgacag tgtcattttc gccaatattg caaccccca gcagctggat      240 caaaaaccca tcaccttctt ccgtcaagta ctcagtcttc tcgagaacac cgcattgctt     300
gaaaaaccgg aggtcctgcg gtcgtctttc ggctacaacc aggacgtcat tgaccgggct     360
aagaagcttc ttgcggacat tcagagcgtc ggtgcctaca gtcacagcca gggagcacca     420
gtaattcggg agagcgtggc caaattcatc gaggagcgtg atggcttccc cgccaacccg     480
caagacctgt acctctgcgc tggtgcgtcg tccggtgtta gcacgctgct gaatgtcatc     540
tgcaacggtc ccaccgccgg tgtccttgtg ccgattcccc aatatcctct gtacaccgcc     600
accctgtccc ttctcaatgc acagtgcgtc ccataccatt tagaggagga caaggcctgg     660
ggtaccgacg tggaggccat ccggcaatct ctggtgcgcg ccaaggccga gggcactgag     720
gttcgtgcta tcgtcgtcat caaccccggt aacccgacgg tgcctcgct cagccccgag      780 gacatcaaga gcgtgcttga catcgccgcc gaggagaagc tggtcgtcat cgccgacgag     840
gtgtaccaga ccaacgtctt cgtgggcgag ttcacatcct tcaagaagag actgcgccaa     900
ctccagcagg aggtgcctgg caagtacgac aatgtcgaac ttgcttctct gcacagtgtg     960
tccaagggta tggtgggcga atgcggtcac cgaggcggtt actttgaact cgtcggattc    1020 gacccctgg tcgcggccga gatttacaag tttgttagca ttatgctgtg cccgccggtg     1080
atcggtcagt gcctggtcga acttatggtg aacccaccca agaagggcga gcccagttac    1140
gagttgtatc agaaggagta caacagcatt agcgatggcc tacacaagcg tgccctcgcc    1200
ctgtacgaag ccttcaagca gatggagggc gttgaatgcc aggagcctca gggcgccatg    1260
tacctcttcc ccagcatcac cctgcccccc aaggccgtcg aagccgccgc tgccgaaggt    1320
cggaacgccg acgaattcta ctgtctgcgc ctcctcgacg caacgggtgt tgcgtggtc     1380 cccggttccg gctttggaca gaaggagaac acgctccact tccgcacaac cttccttgcc    1440
cccggcactg actgggtcga gcggatcgtc aagttccacg ccgagttcat ggccaagtat    1500
aaatag                                                              1506
```

<210> SEQ ID NO 38

<211> LENGTH: 501
<212> TYPE: PRT
<213> ORGANISM: Aspergillus fumigatus

<400> SEQUENCE: 38

```
Met Ile Thr Glu Pro Thr Met Thr Val Pro Tyr Thr Thr Lys Arg Thr
1               5                   10                  15

Ala Ser Asp Leu Gly Pro Arg Leu Arg Ala Asp Asn Ile Asn Pro
            20                  25                  30

Asn Val Lys Ala Ala Lys Tyr Ala Val Arg Gly Glu Leu Ala Val Lys
            35                  40                  45

Ala Glu Glu Tyr Arg Val Arg Leu Ala Lys Gly Asp Lys Ser Leu Pro
        50                  55                  60

Phe Asp Ser Val Ile Phe Ala Asn Ile Gly Asn Pro Gln Gln Leu Asp
65                  70                  75                  80

Gln Lys Pro Ile Thr Phe Phe Arg Gln Val Leu Ser Leu Leu Glu Asn
                85                  90                  95

Thr Ala Leu Leu Glu Lys Pro Glu Val Leu Arg Ser Ser Phe Gly Tyr
            100                 105                 110

Asn Gln Asp Val Ile Asp Arg Ala Lys Lys Leu Leu Ala Asp Ile Gln
            115                 120                 125

Ser Val Gly Ala Tyr Ser His Ser Gln Gly Ala Pro Val Ile Arg Glu
        130                 135                 140

Ser Val Ala Lys Phe Ile Glu Glu Arg Asp Gly Phe Pro Ala Asn Pro
145                 150                 155                 160

Gln Asp Leu Tyr Leu Cys Ala Gly Ala Ser Ser Gly Val Ser Thr Leu
                165                 170                 175

Leu Asn Val Ile Cys Asn Gly Pro Thr Ala Gly Val Leu Val Pro Ile
            180                 185                 190

Pro Gln Tyr Pro Leu Tyr Thr Ala Thr Leu Ser Leu Leu Asn Ala Gln
            195                 200                 205

Cys Val Pro Tyr His Leu Glu Glu Asp Lys Ala Trp Gly Thr Asp Val
        210                 215                 220

Glu Ala Ile Arg Gln Ser Leu Val Arg Ala Lys Ala Glu Gly Thr Glu
225                 230                 235                 240

Val Arg Ala Ile Val Val Ile Asn Pro Gly Asn Pro Thr Gly Ala Ser
                245                 250                 255

Leu Ser Pro Glu Asp Ile Lys Ser Val Leu Asp Ile Ala Ala Glu Glu
            260                 265                 270

Lys Leu Val Val Ile Ala Asp Glu Val Tyr Gln Thr Asn Val Phe Val
            275                 280                 285

Gly Glu Phe Thr Ser Phe Lys Lys Arg Leu Arg Gln Leu Gln Gln Glu
        290                 295                 300

Val Pro Gly Lys Tyr Asp Asn Val Glu Leu Ala Ser Leu His Ser Val
305                 310                 315                 320

Ser Lys Gly Met Val Gly Glu Cys Gly His Arg Gly Gly Tyr Phe Glu
                325                 330                 335

Leu Val Gly Phe Asp Pro Leu Val Ala Ala Glu Ile Tyr Lys Phe Val
            340                 345                 350

Ser Ile Met Leu Cys Pro Pro Val Ile Gly Gln Cys Leu Val Glu Leu
            355                 360                 365

Met Val Asn Pro Pro Lys Lys Gly Glu Pro Ser Tyr Glu Leu Tyr Gln
        370                 375                 380

Lys Glu Tyr Asn Ser Ile Ser Asp Gly Leu His Lys Arg Ala Leu Ala
385                 390                 395                 400
```

```
Leu Tyr Glu Ala Phe Lys Gln Met Glu Gly Val Glu Cys Gln Glu Pro
            405                 410                 415
Gln Gly Ala Met Tyr Leu Phe Pro Ser Ile Thr Leu Pro Pro Lys Ala
        420                 425                 430
Val Glu Ala Ala Ala Glu Gly Arg Asn Ala Asp Glu Phe Tyr Cys
            435                 440                 445
Leu Arg Leu Leu Asp Ala Thr Gly Val Cys Val Pro Gly Ser Gly
450                 455                 460
Phe Gly Gln Lys Glu Asn Thr Leu His Phe Arg Thr Thr Phe Leu Ala
465                 470                 475                 480
Pro Gly Thr Asp Trp Val Glu Arg Ile Val Lys Phe His Ala Glu Phe
            485                 490                 495
Met Ala Lys Tyr Lys
            500

<210> SEQ ID NO 39
<211> LENGTH: 1497
<212> TYPE: DNA
<213> ORGANISM: Aspergillus oryzae

<400> SEQUENCE: 39
```

| | | |
|---|---|---|
| atggcgactc agactacagt gtcctacact actacacgca ccttgtccac cccggctcgt | 60 |
| tgcctgaacc ctgataacat caaccccac gtcacggagg ccaagtatgc cgtccgtggt | 120 |
| gagcttgctg tcaaggccga ggagtaccgc gtgaaactgg ccaatggaga caaatcgtta | 180 |
| cctttcgaca gtgtcatctt tgccaacatc ggcaatcccc aacagctcga ccagaaaccc | 240 |
| atcaccttct ccgccaagt actcagtctc ctcgagaacc ctcaactgtt gaacaacacg | 300 |
| gaagcacttc gtacatcctt tttttatgaa caagatgtcg ttgaccgggc caagaagctc | 360 |
| ctcgcggatg tccagagcgt tggtgcttac agtcacagcc agggagcgcc tgtgatccgc | 420 |
| caaagtatcg ccaaattcat tgaggagcgt gatggattcc cggccaaccc tcaggatttg | 480 |
| ttctgctgcg ctggtgcctc gtctggcgtc agcaccattc tcaatatcat ctgcaacggc | 540 |
| ccccaggccg tgtcctcgt ccctattccg caataccctc tttacactgc caccctttct | 600 |
| ctcctgaatg cgcaatgtgt acccctacctc ctcgaagagc aaaaggcttg gggtaccgat | 660 |
| gtgactgcca tccgtaactc gttggcgcag gcccggtcta ccggcactga cgttcgttcg | 720 |
| attgtggtca tcaaccccgg taaccctact ggtgcctctt tgagcgccga ggatatcaag | 780 |
| aatgttcttg accttgctgc ggaggagaag cttgttgtta ttgcggacga ggtttaccag | 840 |
| acgaacgttt tcgagggcga gttcatttcg ttcaagaaga ggcttcgtca gctgcaacag | 900 |
| gagacaccag gcaagtatga ttatgtggag ttggtctctc ttcacagtgt gtctaaaggt | 960 |
| atggtgggcg agtgtggcca ccgtggtggc tactttgagc tggttggatt cgaccctgag | 1020 |
| gttcaggccc agatctacaa gcttgtgagc atcggacttt gcccaccagt cattggacag | 1080 |
| tgtttgcttg agcttatggt gaacccaccc aaggagggcg aaggcagcta tgagctgtac | 1140 |
| cagaaggagt acaatggaat cagcgaggga ctgcacaagc gcgcctttgc cttatacgag | 1200 |
| gccttccaac agatggaggg cgttgagtgt cagaaacctc agggtgccat gtatctcttc | 1260 |
| cccaccatca ctctcccacc caaggccatt gaggctgcca ggctgagaa ccgtgccgcc | 1320 |
| gatgagttct actgcttgcg tctcctcgac gctaccggtg tctgtgttgt ccctggctcc | 1380 |
| ggcttcggcc agaaggagaa cactctgcac ttccgcacaa ctttcctggc ccctggcact | 1440 |
| gattgggttg aacggatcgt caagttccac tccgaattta tggccaagta caaataa | 1497 |

<210> SEQ ID NO 40
<211> LENGTH: 498
<212> TYPE: PRT
<213> ORGANISM: Aspergillus oryzae

<400> SEQUENCE: 40

```
Met Ala Thr Gln Thr Thr Val Ser Tyr Thr Thr Thr Arg Thr Leu Ser
 1               5                  10                  15

Thr Pro Ala Arg Cys Leu Asn Pro Asp Asn Ile Asn Pro His Val Thr
            20                  25                  30

Glu Ala Lys Tyr Ala Val Arg Gly Glu Leu Ala Val Lys Ala Glu Glu
        35                  40                  45

Tyr Arg Val Lys Leu Ala Asn Gly Asp Lys Ser Leu Pro Phe Asp Ser
    50                  55                  60

Val Ile Phe Ala Asn Ile Gly Asn Pro Gln Gln Leu Asp Gln Lys Pro
65                  70                  75                  80

Ile Thr Phe Phe Arg Gln Val Leu Ser Leu Leu Glu Asn Pro Gln Leu
                85                  90                  95

Leu Asn Asn Thr Glu Ala Leu Arg Thr Ser Phe Phe Tyr Glu Gln Asp
            100                 105                 110

Val Val Asp Arg Ala Lys Lys Leu Leu Ala Asp Val Gln Ser Val Gly
        115                 120                 125

Ala Tyr Ser His Ser Gln Gly Ala Pro Val Ile Arg Gln Ser Ile Ala
    130                 135                 140

Lys Phe Ile Glu Glu Arg Asp Gly Phe Pro Ala Asn Pro Gln Asp Leu
145                 150                 155                 160

Phe Cys Cys Ala Gly Ala Ser Ser Gly Val Ser Thr Ile Leu Asn Ile
                165                 170                 175

Ile Cys Asn Gly Pro Gln Ala Gly Val Leu Val Pro Ile Pro Gln Tyr
            180                 185                 190

Pro Leu Tyr Thr Ala Thr Leu Ser Leu Leu Asn Ala Gln Cys Val Pro
    195                 200                 205

Tyr Leu Leu Glu Glu Gln Lys Ala Trp Gly Thr Asp Val Thr Ala Ile
    210                 215                 220

Arg Asn Ser Leu Ala Gln Ala Arg Ser Thr Gly Thr Asp Val Arg Ser
225                 230                 235                 240

Ile Val Val Ile Asn Pro Gly Asn Pro Thr Gly Ala Ser Leu Ser Ala
                245                 250                 255

Glu Asp Ile Lys Asn Val Leu Ala Leu Ala Glu Glu Lys Leu Val
            260                 265                 270

Val Ile Ala Asp Glu Val Tyr Gln Thr Asn Val Phe Glu Gly Glu Phe
    275                 280                 285

Ile Ser Phe Lys Lys Arg Leu Arg Gln Leu Gln Gln Glu Thr Pro Gly
    290                 295                 300

Lys Tyr Asp Tyr Val Glu Leu Val Ser Leu His Ser Val Ser Lys Gly
305                 310                 315                 320

Met Val Gly Glu Cys Gly His Arg Gly Gly Tyr Phe Glu Leu Val Gly
                325                 330                 335

Phe Asp Pro Glu Val Gln Ala Gln Ile Tyr Lys Leu Val Ser Ile Gly
            340                 345                 350

Leu Cys Pro Pro Val Ile Gly Gln Cys Leu Leu Glu Leu Met Val Asn
    355                 360                 365

Pro Pro Lys Glu Gly Glu Gly Ser Tyr Glu Leu Tyr Gln Lys Glu Tyr
    370                 375                 380
```

-continued

Asn Gly Ile Ser Glu Gly Leu His Lys Arg Ala Phe Ala Leu Tyr Glu
385                 390                 395                 400

Ala Phe Gln Gln Met Glu Gly Val Glu Cys Gln Lys Pro Gln Gly Ala
            405                 410                 415

Met Tyr Leu Phe Pro Thr Ile Thr Leu Pro Pro Lys Ala Ile Glu Ala
            420                 425                 430

Ala Lys Ala Glu Asn Arg Ala Ala Asp Glu Phe Tyr Cys Leu Arg Leu
        435                 440                 445

Leu Asp Ala Thr Gly Val Cys Val Val Pro Gly Ser Gly Phe Gly Gln
    450                 455                 460

Lys Glu Asn Thr Leu His Phe Arg Thr Thr Phe Leu Ala Pro Gly Thr
465                 470                 475                 480

Asp Trp Val Glu Arg Ile Val Lys Phe His Ser Glu Phe Met Ala Lys
                485                 490                 495

Tyr Lys

<210> SEQ ID NO 41
<211> LENGTH: 1542
<212> TYPE: DNA
<213> ORGANISM: Cryptococcus neoformans

<400> SEQUENCE: 41
atgcccagac ttagcaacgt ctattgtccc aaatcactct acaacgtca gaccatccaa      60 atcaggtcat tcagtcagac tatgtcacct ttcaaaccccg cgcttactct tgataccatc    120
aaccccgcgg ttcaggctgt tcactatgct gtccgaggcg agctcgcgat caaggcggac    180
aaatatgtcc aagtccttgc cgatataact cacaagcctt gccgtttga aagatcgtc      240 actgccaaca tcggtaatcc ccaacaacaa ggtcttgatc aagttcctct cacttattgg    300
cgacaaatta tttccttatt ggagtatccc gatctgatgc agaaacatga gcagttggcc    360
aagcagattt accctggaga tgtgattgag cgagccaggg cgttacataa cgaaattgga    420
agtacgggtg cgtacactca ttccaagggt gtgttgggta tcagaaagag agtcgccaag    480
tttattgaag aacgcgacgg ttacccggcg gaccctcaaa atatcttcct caccgccggt    540
gcttctgccg tgttgcttc gatccttggt gtcgccctcc gcagaggtga tggctgcatg    600
atccccatcc cccaatatcc cctctatacc gccacccctcg cttacctcga gtctgagcct    660
ctgccatact acctttctga agcggacgac tggtcgatga ccacgattc tttgctcaag    720 agcgtggagg aaggcaagaa gaagggtatc cccatcaagg cgcttgtaat cattaacccc    780
ggaaacccta ccggcgcatg tttgagccaa gaggcgatgg aggcggttgt gcatctctgt    840
tatgaggaag gtatcgtcct cctcgcagac gaggtttacc agatgaacgt ctttgacccc    900
gaacagcgac cgttcatttc tttcaaaaag gttttgatgg atatgcccaa ggagatcagg    960
gaaagtgtgg aactggtatc tttccattcg atctcaaaag gtgttagtgg agaatgtgga   1020
aggagaggtg gatactttga atgtgtcaac attgataagg atgtgatgga ccaggtttac   1080
aagatggcga gtgtcacttt atgtcctccc gtctcaggcc agatcggtgt cgacctcatg   1140
gtctcccctc cgaaacccgg agacgaatct taccccttat ggaaagaaga aaccgatctg   1200
atccaaaaca atctcaagtc ccgatcatat ctcatggctg agcatttcaa caaaatggaa   1260
ggtgtttctt gcaacaatgc ggaaggagcc atgtacttgt tcccgaggat taatatccct   1320
cccaaagctg tagaggcggc gaagaagttg ggtaaggaac cggatgtgat gtatgctttg   1380
gatcttcttg atgcgaccgg tatctgtgcg gtggcaggca gcggttttgg ccaagaaccg   1440
gggacgttcc atttgcgagt gactgccctg tgtcccgata ctgctgaatt tatcggtcga   1500
ttccaaaagt tcaacaagga atttatggaa aagtatgcct aa        1542

<210> SEQ ID NO 42
<211> LENGTH: 480
<212> TYPE: PRT
<213> ORGANISM: Cryptococcus neoformans

<400> SEQUENCE: 42

Met Pro Arg Leu Ser Asn Val Tyr Cys Pro Lys Ser Leu Leu Gln Arg
1               5                   10                  15

Gln Thr Ile Gln Ile Arg Ser Phe Ser Gln Thr Met Ser Pro Phe Lys
            20                  25                  30

Pro Ala Leu Thr Leu Asp Thr Ile Asn Pro Ala Val Gln Ala Val His
        35                  40                  45

Tyr Ala Val Arg Gly Glu Leu Ala Ile Lys Ala Asp Lys Tyr Val Gln
    50                  55                  60

Val Leu Ala Asp Ile Thr His Lys Pro Leu Pro Phe Glu Lys Ile Val
65                  70                  75                  80

Thr Ala Asn Ile Gly Asn Pro Gln Gln Gln Gly Leu Asp Gln Val Pro
                85                  90                  95

Leu Thr Tyr Trp Arg Gln Ile Ile Ser Leu Leu Glu Tyr Pro Asp Leu
            100                 105                 110

Met Gln Lys His Glu Gln Leu Ala Lys Gln Ile Tyr Pro Gly Asp Val
        115                 120                 125

Ile Glu Arg Ala Arg Ala Leu His Asn Glu Ile Gly Ser Thr Gly Ala
    130                 135                 140

Tyr Thr His Ser Lys Gly Val Leu Gly Ile Arg Lys Arg Val Ala Lys
145                 150                 155                 160

Phe Ile Glu Glu Arg Asp Gly Tyr Pro Ala Asp Pro Gln Asn Ile Phe
                165                 170                 175

Leu Thr Ala Gly Ala Ser Ala Gly Val Ala Ser Ile Leu Gly Val Ala
            180                 185                 190

Leu Arg Arg Gly Asp Gly Cys Met Ile Pro Ile Pro Gln Tyr Pro Leu
        195                 200                 205

Tyr Thr Ala Thr Leu Ala Tyr Leu Glu Ser Glu Pro Leu Pro Tyr Tyr
    210                 215                 220

Leu Ser Glu Ala Asp Asp Trp Ser Met Asn His Asp Ser Leu Leu Lys
225                 230                 235                 240

Ser Val Glu Glu Gly Lys Lys Lys Gly Ile Pro Ile Lys Ala Leu Val
                245                 250                 255

Ile Ile Asn Pro Gly Asn Pro Thr Gly Ala Cys Leu Ser Gln Glu Ala
            260                 265                 270

Met Glu Ala Val Val His Leu Cys Tyr Glu Glu Gly Ile Val Leu Leu
        275                 280                 285

Ala Asp Glu Val Tyr Gln Met Asn Val Phe Asp Pro Gln Arg Pro
    290                 295                 300

Phe Ile Ser Phe Lys Lys Val Leu Met Asp Met Pro Lys Glu Ile Arg
305                 310                 315                 320

Glu Ser Val Glu Leu Val Ser Phe His Ser Ile Ser Lys Gly Val Ser
                325                 330                 335

Gly Glu Cys Gly Arg Arg Gly Tyr Phe Glu Cys Val Asn Ile Asp
        340                 345                 350

Lys Asp Val Met Asp Gln Val Tyr Lys Met Ala Ser Val Thr Leu Cys
    355                 360                 365

```
Pro Pro Val Ser Gly Gln Ile Gly Val Asp Leu Met Val Ser Pro Pro
        370                 375                 380

Lys Pro Gly Asp Glu Ser Tyr Pro Leu Trp Lys Glu Glu Thr Asp Leu
385                 390                 395                 400

Ile Gln Asn Asn Leu Lys Ser Arg Ser Tyr Leu Met Ala Glu His Phe
                405                 410                 415

Asn Lys Met Glu Gly Val Ser Cys Asn Asn Ala Glu Gly Ala Met Tyr
            420                 425                 430

Leu Phe Pro Arg Ile Asn Ile Pro Pro Lys Ala Val Glu Ala Ala Lys
                435                 440                 445

Lys Leu Gly Lys Glu Pro Asp Val Met Tyr Ala Leu Asp Leu Leu Asp
450                 455                 460

Ala Thr Gly Ile Cys Ala Val Ala Gly Ser Gly Phe Gly Gln Glu Pro
465                 470                 475                 480

<210> SEQ ID NO 43
<211> LENGTH: 1605
<212> TYPE: DNA
<213> ORGANISM: Dictyostelium discoideum

<400> SEQUENCE: 43
atgttcaaaa gaagtttaaa agttttatta tcaaatccac ccatcaacag agtaaagccc      60
tcttcaacaa ttattcaacc actttcaaat actactacaa caacaataat taataataat     120
aatataacta attttgaaaa aatgacacat aaaaaatcta tgacaattga taatatttgc     180
caaaatgtaa gaaatgcaca atatgcagta cgtggtgaat tagttattcg tgcagaagca     240
atttcacatc aattacaaaa acaaaaaaca gaaggcacaa aaacattacc atttgaagag     300
attgtctatt gtaatattgg taatccacaa caattgaaac aaaaaccatt aacttatttc     360
cgtcaagttg tatcattagt tgaatgtcca gatttattag ataatccata cgttgaaaag     420
atatatccag ccgatgttat ctcacgtgct aaagagatat taggatcaat taataataca     480
acaggtgcct attccaatag tcaaggtatt ggtttagttt taagatcagt tgcagatttc     540
atagagagac gtgatggaca taatctgat ccatccgaaa ttttccttac agatggtgca     600
tcagttggtg tacaacgtat tttgaaactt ttaattaaag atcgttcaga cggtatctta     660
attccaattc cacaatatcc actctacagt gccaccattg aattatataa tggcagtcaa     720
ttagggtacc tattaaatga agagaaaggt tggtcactcg agatctccca attggagcat     780
tcctacaatg atgcagtttc aaagggtatt aatccacgtg cactcgttat catcaatcca     840
ggtaatccaa ctggtcaatg tttagataga gcaaatatgg aagagattgt caagttttgt     900
ttagaaaaga atgtagtatt attggctgat gaagtctatc aagagaatgt ttatgtcaaa     960
gagagtaaac cattcatctc attcaaaaag gttgtcaaag atatgggtgg tgattatgca    1020
gatttagaga tggttttcatt ccattcagtt agtaaaggtt tcgttggtga atgtggtaaa    1080
cgtggtggtt atatggaatt aaatggtgtc actcaagatg ttaaagctga aatttataaa    1140
ctcgcatcaa ttggtttatg tccaaatgtt attggtcaat ggttgttga tttaatggtt    1200
cgtccaccag ttgctggtga acaatcacat gatctctacc ttaaagaaag agataatatc    1260
tatgaatctt taaaaaaacg tgcaaatctc ttaacaaatg ctttaaataa tcttgaaggt    1320
gtaacttgta atccatcaga aggtgcaatg tatgctttcc cacaaattcg tcttccagct    1380
aaagctgtag aatatgcaaa ttcaattggt aaagcaccag atgcttacta ttgtattcaa    1440
ttactcgaag ccactggtat ctgtgttgta ccaggtagtg gtttcggtca aaaagatggt    1500
acttggcatt ttagaactac cttcttacct tctgaagaag caattgaagg tgtttgtaag    1560
```
agaatcgctg atttccatca atcatttatg aataaatata aataa                    1605

<210> SEQ ID NO 44
<211> LENGTH: 534
<212> TYPE: PRT
<213> ORGANISM: Dictyostelium discoideum

<400> SEQUENCE: 44

Met Phe Lys Arg Ser Leu Lys Val Leu Leu Ser Asn Pro Pro Ile Asn
1               5                   10                  15

Arg Val Lys Pro Ser Ser Thr Ile Ile Gln Pro Leu Ser Asn Thr Thr
                20                  25                  30

Thr Thr Thr Ile Ile Asn Asn Asn Ile Thr Asn Phe Glu Lys Met
            35                  40                  45

Thr His Lys Lys Ser Met Thr Ile Asp Asn Ile Cys Gln Asn Val Arg
    50                  55                  60

Asn Ala Gln Tyr Ala Val Arg Gly Glu Leu Val Ile Arg Ala Glu Ala
65                  70                  75                  80

Ile Ser His Gln Leu Gln Lys Gln Lys Thr Glu Gly Thr Lys Thr Leu
                85                  90                  95

Pro Phe Glu Glu Ile Val Tyr Cys Asn Ile Gly Asn Pro Gln Gln Leu
            100                 105                 110

Lys Gln Lys Pro Leu Thr Tyr Phe Arg Gln Val Val Ser Leu Val Glu
        115                 120                 125

Cys Pro Asp Leu Leu Asp Asn Pro Tyr Val Lys Ile Tyr Pro Ala
    130                 135                 140

Asp Val Ile Ser Arg Ala Lys Glu Ile Leu Gly Ser Ile Asn Asn Thr
145                 150                 155                 160

Thr Gly Ala Tyr Ser Asn Ser Gln Gly Ile Gly Leu Val Leu Arg Ser
                165                 170                 175

Val Ala Asp Phe Ile Glu Arg Arg Asp Gly His Lys Ser Asp Pro Ser
            180                 185                 190

Glu Ile Phe Leu Thr Asp Gly Ala Ser Val Gly Val Gln Arg Ile Leu
        195                 200                 205

Lys Leu Leu Ile Lys Asp Arg Ser Asp Gly Ile Leu Ile Pro Ile Pro
    210                 215                 220

Gln Tyr Pro Leu Tyr Ser Ala Thr Ile Glu Leu Tyr Asn Gly Ser Gln
225                 230                 235                 240

Leu Gly Tyr Leu Leu Asn Glu Glu Lys Gly Trp Ser Leu Glu Ile Ser
                245                 250                 255

Gln Leu Glu His Ser Tyr Asn Asp Ala Val Ser Lys Gly Ile Asn Pro
            260                 265                 270

Arg Ala Leu Val Ile Ile Asn Pro Gly Asn Pro Thr Gly Gln Cys Leu
        275                 280                 285

Asp Arg Ala Asn Met Glu Glu Ile Val Lys Phe Cys Leu Glu Lys Asn
    290                 295                 300

Val Val Leu Leu Ala Asp Glu Val Tyr Gln Glu Asn Val Tyr Val Lys
305                 310                 315                 320

Glu Ser Lys Pro Phe Ile Ser Phe Lys Lys Val Val Lys Asp Met Gly
                325                 330                 335

Gly Asp Tyr Ala Asp Leu Glu Met Val Ser Phe His Ser Val Ser Lys
            340                 345                 350

Gly Phe Val Gly Glu Cys Gly Lys Arg Gly Gly Tyr Met Glu Leu Asn
        355                 360                 365

```
Gly Val Thr Gln Asp Val Lys Ala Glu Ile Tyr Lys Leu Ala Ser Ile
            370                 375                 380

Gly Leu Cys Pro Asn Val Ile Gly Gln Leu Val Asp Leu Met Val
385                 390                 395                 400

Arg Pro Pro Val Ala Gly Glu Gln Ser His Asp Leu Tyr Leu Lys Glu
                405                 410                 415

Arg Asp Asn Ile Tyr Glu Ser Leu Lys Lys Arg Ala Asn Leu Leu Thr
                420                 425                 430

Asn Ala Leu Asn Asn Leu Glu Gly Val Thr Cys Asn Pro Ser Glu Gly
            435                 440                 445

Ala Met Tyr Ala Phe Pro Gln Ile Arg Leu Pro Ala Lys Ala Val Glu
        450                 455                 460

Tyr Ala Asn Ser Ile Gly Lys Ala Pro Asp Ala Tyr Tyr Cys Ile Gln
465                 470                 475                 480

Leu Leu Glu Ala Thr Gly Ile Cys Val Val Pro Gly Ser Gly Phe Gly
                485                 490                 495

Gln Lys Asp Gly Thr Trp His Phe Arg Thr Thr Phe Leu Pro Ser Glu
            500                 505                 510

Glu Ala Ile Glu Gly Val Cys Lys Arg Ile Ala Asp Phe His Gln Ser
        515                 520                 525

Phe Met Asn Lys Tyr Lys
    530
```

<210> SEQ ID NO 45
<211> LENGTH: 1710
<212> TYPE: DNA
<213> ORGANISM: Trypanosoma brucei

<400> SEQUENCE: 45

```
atggatatat atttattttc cgtttggttt atacagaacg aggaaaagtg tttggatttt      60
ctaaacatta gtaagaagaa caaagccaag tcgagcgtac aacacattgg cgggttagcg     120
cgaaaacaga atcctgaacc cacaaaatca attttgtgt cgagatacgg agcacgatca      180
ctgaagacct cgacaatgaa aggtaaccag gaattttttc agaagggtgg ggcccacgtt     240
tccaagggcg ttcacatcaa cccacgcgta agaaggctc agtatgccgt gcgcgggctt     300
gtgccgatgc gagccgacga aatcagggag gaaatccgtt caggcacggg gaagtcgaag     360
ttctccttca acgaactggt ttactgcaac attggcaacc cccaagccct ggagcagaag     420
ccgcttacct tcaccgcca agtgatgtcg cttatcgatg ctccatttct gcttgaggat      480
aacgccgtcg tctctcgata tccctctgat gctgtttccc gtgcgcgtct ctacttgggc     540
cacatcggcc aacgtactgg cgcctacacg gactccgcag gctatgcctt tgtacgtgac     600
atcgtcgcgc agtatgtgaa tgagcgtgac gcctatgtaa aaccgcttca ggaggcatcg     660
tcgattgtgc ttacagacgg cgcaagcact ggtgtgcgca taatcttaca gacgcttgtg     720
ggcgatgaga aggacgctgt gatgattccc atcccgcagt atccgctgta cacggcacag     780
attgcattgt tgggaggtac ccccgcgatg tattaccttc gtgagagcga aggctgggcg     840
ctgaacgttg gagagctcga ggcagtatac aaagactgtg tggcgaacgg aaacgcgacg     900
ccccgcgtgc tcgtcgtgat taaccctggt aaccctacag gtggcgtgtt ggagcgcact     960
gtgatggagg aggttgccaa gttctgttgc gatcacggtt tgtgctcat ggccgatgag     1020 gtttaccagg aaaatatcta caccgcgacc aagcggtttg agagttttcg gaagattgtg    1080
ctcgaacttc caccaccata caacaccgac accgtgcttg tttccttgca ctccgtgtcg    1140
aagggtatta tcggtgagtg tggtcgccgt ggtgggtact tcacactcac aaacgctccg    1200
```

```
cctgagttag tggagcaggt gatgaaattg tgctctatta acctctgcag caacgtcaac    1260
ggtcagctta tgacggcact gatgtgctcc ccgccgaaac ctggcgatgc gagcttcgac    1320
cactacacgg cagagtacag tggcattttt gaaagcctta agcgccgtgc tgacctgctt    1380
gcaaaggaac tgaacaacat ccgtggtttc aagtcccaat ctgttgaggg cgccatgtac    1440
gctttcccca ctattgagct ccctcccaag tacgtgaagc acaacgatga gatgaactca    1500
aaggagggcc gacagcttgc gccggacgcg cgttgggcac tggagcttct cgagagcacc    1560
ggtattgttg tggtgccggg ttctggcttt gggcagcagc ctgggacact gcacttccgc    1620
acgacgatcc tcccacccga agcgcatatg gagcgtgtgg tgaaggctct gcgccagttc    1680
caggagggca tttgggccaa gtatgcataa                                     1710
```

<210> SEQ ID NO 46
<211> LENGTH: 569
<212> TYPE: PRT
<213> ORGANISM: Trypanosoma brucei

<400> SEQUENCE: 46

```
Met Asp Ile Tyr Leu Phe Ser Val Trp Phe Ile Gln Asn Glu Glu Lys
1               5                  10                  15

Cys Leu Asp Phe Leu Asn Ile Ser Lys Lys Asn Lys Ala Lys Ser Ser
            20                  25                  30

Val Gln His Ile Gly Gly Leu Ala Arg Lys Gln Asn Pro Glu Pro Thr
        35                  40                  45

Lys Ser Ile Phe Val Ser Arg Tyr Gly Ala Arg Ser Leu Lys Thr Ser
    50                  55                  60

Thr Met Lys Gly Asn Gln Glu Phe Phe Gln Lys Gly Ala His Val
65                  70                  75                  80

Ser Lys Gly Val His Ile Asn Pro Arg Val Lys Lys Ala Gln Tyr Ala
                85                  90                  95

Val Arg Gly Leu Val Pro Met Arg Ala Asp Glu Ile Arg Glu Ile
            100                 105                 110

Arg Ser Gly Thr Gly Lys Ser Lys Phe Ser Phe Asn Glu Leu Val Tyr
        115                 120                 125

Cys Asn Ile Gly Asn Pro Gln Ala Leu Glu Gln Lys Pro Leu Thr Phe
    130                 135                 140

His Arg Gln Val Met Ser Leu Ile Asp Ala Pro Phe Leu Leu Glu Asp
145                 150                 155                 160

Asn Ala Val Val Ser Arg Tyr Pro Ser Asp Ala Val Ser Arg Ala Arg
                165                 170                 175

Leu Tyr Leu Gly His Ile Gly Gln Arg Thr Gly Ala Tyr Thr Asp Ser
            180                 185                 190

Ala Gly Tyr Ala Phe Val Arg Asp Ile Val Ala Gln Tyr Val Asn Glu
        195                 200                 205

Arg Asp Ala Tyr Val Lys Pro Leu Gln Glu Ala Ser Ser Ile Val Leu
    210                 215                 220

Thr Asp Gly Ala Ser Thr Gly Val Arg Ile Ile Leu Gln Thr Leu Val
225                 230                 235                 240

Gly Asp Glu Lys Asp Ala Val Met Ile Pro Ile Pro Gln Tyr Pro Leu
                245                 250                 255

Tyr Thr Ala Gln Ile Ala Leu Leu Gly Gly Thr Pro Ala Met Tyr Tyr
            260                 265                 270

Leu Arg Glu Ser Glu Gly Trp Ala Leu Asn Val Gly Glu Leu Glu Ala
        275                 280                 285
```

Val Tyr Lys Asp Cys Val Ala Asn Gly Asn Ala Thr Pro Arg Val Leu
    290                 295                 300

Val Val Ile Asn Pro Gly Asn Pro Thr Gly Gly Val Leu Glu Arg Thr
305                 310                 315                 320

Val Met Glu Glu Val Ala Lys Phe Cys Cys Asp His Gly Val Val Leu
                325                 330                 335

Met Ala Asp Glu Val Tyr Gln Glu Asn Ile Tyr Thr Ala Thr Lys Arg
            340                 345                 350

Phe Glu Ser Phe Arg Lys Ile Val Leu Glu Leu Pro Pro Tyr Asn
        355                 360                 365

Thr Asp Thr Val Leu Val Ser Leu His Ser Val Ser Lys Gly Ile Ile
    370                 375                 380

Gly Glu Cys Gly Arg Arg Gly Gly Tyr Phe Thr Leu Thr Asn Ala Pro
385                 390                 395                 400

Pro Glu Leu Val Glu Gln Val Met Lys Leu Cys Ser Ile Asn Leu Cys
                405                 410                 415

Ser Asn Val Asn Gly Gln Leu Met Thr Ala Leu Met Cys Ser Pro Pro
            420                 425                 430

Lys Pro Gly Asp Ala Ser Phe Asp His Tyr Thr Ala Glu Tyr Ser Gly
        435                 440                 445

Ile Phe Glu Ser Leu Lys Arg Arg Ala Asp Leu Leu Ala Lys Glu Leu
    450                 455                 460

Asn Asn Ile Arg Gly Phe Lys Ser Gln Ser Val Glu Gly Ala Met Tyr
465                 470                 475                 480

Ala Phe Pro Thr Ile Glu Leu Pro Pro Lys Tyr Val Lys His Asn Asp
                485                 490                 495

Glu Met Asn Ser Lys Gly Arg Gln Leu Ala Pro Asp Ala Arg Trp
            500                 505                 510

Ala Leu Glu Leu Leu Glu Ser Thr Gly Ile Val Val Pro Gly Ser
        515                 520                 525

Gly Phe Gly Gln Gln Pro Gly Thr Leu His Phe Arg Thr Thr Ile Leu
    530                 535                 540

Pro Pro Glu Ala His Met Glu Arg Val Val Lys Ala Leu Arg Gln Phe
545                 550                 555                 560

Gln Glu Gly Ile Trp Ala Lys Tyr Ala
                565

<210> SEQ ID NO 47
<211> LENGTH: 1494
<212> TYPE: DNA
<213> ORGANISM: Leishmania major

<400> SEQUENCE: 47
atgctgcgcc acgctgctcg ttgcttttca ccaaggcaat gctacgtaag ccctcgcgtc      60
atggaggcgg aatacgccgt gcggggggctg atcccggcgc gcgcggatga gatcaaggcg     120
gacttggcta caggccacgg cacctactcg ttcgaaagcc tcgtgtactg caacatcggc     180
aacccgcagt cagtggggca gatgccgcta acgttctacc acaagtgat ggtgctcgtc      240 gatgcgccgt tcctgctgga ggatgcggaa atcgttgcgc ggctgccaga ggacgccgtt     300
gcacgcgcgc gcaggtacct ttcggagatc gggacgggca ccggcgcgta cagagtctt     360 ttcggcttcc ggtttgcccg cgctgccgtt gcggcgcaca tcaacgagct cgaccatggc    420
gtgagcccgg ctgcgacggt gaacgatatc tgtctgacag acggcgcgag catgggtgcg    480
aagctgttcc tgcagctcct tgtgggcggc gcgagcgatg ctgtgatgat cccggttccg    540

-continued

```
cagtatccgc tatactctgc gcagattgct ttacttggcg gggtgaaggt gccctacggc    600
ctgcacgagt ctgaggggtg ggtaatgaag ttgtcggacc ttgttgccgc gtacgagcgg    660
tgcgtgaccg agagcggcgc gacgccgcgc ttgtttgtgt gcatcaaccc cgggaacccg    720
acggggaacg tactggagcg ctgcgtgatg gaggacgtcg tgcggttctg ccacgagcgc    780
ggcatgctgc tgcttgcaga cgaggtgtac caggagaacg tgtacgacac gcgacgccgg    840
tttttgagct tccgcgaggt tgtgcttggg atgcctgagc cgtactgctc ggagacgatg    900
cttgtgtcac tgcactcgac atcgaaaggg gtgattggtg aatgcgggcg gcgcggcggg    960
tatttctgca tgacgaacct gcctgctgcg ctgcgccagc aggttgtgaa gctgtgctcg   1020
atcaacctgt gtgcaaacgt gaacgggcag ttgatgactg cgctgatgtg ctcgccgccg   1080
cgcgagggcg aagcgagcta cgcgctgcac cggcgcgagt acgacgagat ctttacgggc   1140
atgaaggagc gcgctgagct gctggcgcgc gagcttgggg ctgtgcgcgg gctctcgtgc   1200
caaccggtgg agggcgcaat gtacgcgttc ccgagaattg tgttgcctga gcggtacgcc   1260
cagcggaacg aggagctgaa cgcgaaggag ggtcggcagc ttgcgctgga cgcgcggtgg   1320
gcgctggagc tgctggagtc gagcgggatc gttgttgtgc ccgggtctgg gttcgggcag   1380
gaacccggga cgctgcactt tcggatcacg attctcccgc ctcttgaaca gattgatcgg   1440
atggtgcgtg cgatccgcga gttccaggac cggatctacg agcagtacgc ttaa          1494
```

<210> SEQ ID NO 48
<211> LENGTH: 497
<212> TYPE: PRT
<213> ORGANISM: Leishmania major

<400> SEQUENCE: 48

```
Met Leu Arg His Ala Ala Arg Cys Phe Ser Pro Arg Gln Cys Tyr Val
1               5                   10                  15

Ser Pro Arg Val Met Glu Ala Glu Tyr Ala Val Arg Gly Leu Ile Pro
            20                  25                  30

Ala Arg Ala Asp Glu Ile Lys Ala Asp Leu Ala Thr Gly His Gly Thr
        35                  40                  45

Tyr Ser Phe Glu Ser Leu Val Tyr Cys Asn Ile Gly Asn Pro Gln Ser
    50                  55                  60

Val Gly Gln Met Pro Leu Thr Phe Tyr Arg Gln Val Met Val Leu Val
65                  70                  75                  80

Asp Ala Pro Phe Leu Leu Glu Asp Ala Glu Ile Val Ala Arg Leu Pro
                85                  90                  95

Glu Asp Ala Val Ala Arg Ala Arg Tyr Leu Ser Glu Ile Gly Thr
            100                 105                 110

Gly Thr Gly Ala Tyr Thr Glu Ser Phe Gly Phe Arg Phe Ala Arg Ala
        115                 120                 125

Ala Val Ala Ala His Ile Asn Glu Leu Asp His Gly Val Ser Pro Ala
    130                 135                 140

Ala Thr Val Asn Asp Ile Cys Leu Thr Asp Gly Ala Ser Met Gly Ala
145                 150                 155                 160

Lys Leu Phe Leu Gln Leu Leu Val Gly Gly Ala Ser Asp Ala Val Met
                165                 170                 175

Ile Pro Val Pro Gln Tyr Pro Leu Tyr Ser Ala Gln Ile Ala Leu Leu
            180                 185                 190

Gly Gly Val Lys Val Pro Tyr Gly Leu His Glu Ser Glu Gly Trp Val
        195                 200                 205
```

```
Met Lys Leu Ser Asp Leu Val Ala Ala Tyr Glu Arg Cys Val Thr Glu
            210                 215                 220
Ser Gly Ala Thr Pro Arg Leu Phe Val Cys Ile Asn Pro Gly Asn Pro
225                 230                 235                 240
Thr Gly Asn Val Leu Glu Arg Cys Val Met Glu Asp Val Val Arg Phe
                245                 250                 255
Cys His Glu Arg Gly Met Leu Leu Ala Asp Glu Val Tyr Gln Glu
                260                 265                 270
Asn Val Tyr Asp Thr Arg Arg Phe Leu Ser Phe Arg Glu Val Val
                275                 280                 285
Leu Gly Met Pro Glu Pro Tyr Cys Ser Glu Thr Met Leu Val Ser Leu
            290                 295                 300
His Ser Thr Ser Lys Gly Val Ile Gly Glu Cys Gly Arg Arg Gly Gly
305                 310                 315                 320
Tyr Phe Cys Met Thr Asn Leu Pro Ala Ala Leu Arg Gln Gln Val Val
                    325                 330                 335
Lys Leu Cys Ser Ile Asn Leu Cys Ala Asn Val Asn Gly Gln Leu Met
                340                 345                 350
Thr Ala Leu Met Cys Ser Pro Pro Arg Glu Gly Glu Ala Ser Tyr Ala
            355                 360                 365
Leu His Arg Arg Glu Tyr Asp Glu Ile Phe Thr Gly Met Lys Glu Arg
            370                 375                 380
Ala Glu Leu Leu Ala Arg Glu Leu Gly Ala Val Arg Gly Leu Ser Cys
385                 390                 395                 400
Gln Pro Val Glu Gly Ala Met Tyr Ala Phe Pro Arg Ile Val Leu Pro
                405                 410                 415
Glu Arg Tyr Ala Gln Arg Asn Glu Glu Leu Asn Ala Lys Glu Gly Arg
                420                 425                 430
Gln Leu Ala Leu Asp Ala Arg Trp Ala Leu Glu Leu Leu Glu Ser Ser
            435                 440                 445
Gly Ile Val Val Pro Gly Ser Gly Phe Gly Gln Glu Pro Gly Thr
            450                 455                 460
Leu His Phe Arg Ile Thr Ile Leu Pro Pro Leu Glu Gln Ile Asp Arg
465                 470                 475                 480
Met Val Arg Ala Ile Arg Glu Phe Gln Asp Arg Ile Tyr Glu Gln Tyr
                485                 490                 495
Ala

<210> SEQ ID NO 49
<211> LENGTH: 1455
<212> TYPE: DNA
<213> ORGANISM: Entamoeba histolytica

<400> SEQUENCE: 49
atgaaagcat tttcaagaca aagtattaat ccttgtatca ttgcaactca atatgctgtt      60
agaggaaaat tagtattaga ggcaaatgag attcaaaaag aaattgaaga agcaagaaaa     120
aaaggaaaaa ataatcctta tccatttgag aaagtagttt attgtaatat tggtaatcca     180
cagatatgta accaacagcc attaacatat ccaaggcaga ttatctcaat agttgaatat     240
cctgagcttt taaatcatac aacccttttt ccgaaagatg ttatcaccca tgctaaaaaa     300
attattaata gtcttggttg tactggaaca agtggtgcat atactaattc tatgggagtt     360
attcaattca gaaatcaat ttgtaaattt ataaaacata gagatggaac tgctccatcc     420
cctgatgacg tatttataac cgatggagca tctactggaa taaaaatgat tttaaatatg     480
```

```
ttgatttcac atcctcttca tggaattatg attcctattc cacaataccc attatacagt    540
gcttcaatat ctcaattcgg aggttttcaa attaattact ttctagatga atcaaaaaaa    600
tggtcaacag atatgcatc cgtaagaaaa gtttatgaac aagcggttga aaaaggtatt    660
caagtgaaag gatttgtttg tattaaccca ggtaatccaa ctggacaagt tcttacagtc    720
caaaatatga agaaattat agaattttgc tatgaaaaaa aaatttgttt attagctgat    780
gaagtatatc aagagaatat ctacggtgaa ataccattta catcattcag aaaggtattg    840
aagtcaatga gggatgaggt gaaaaatagt gttgagctaa tctcattttt tagtgtttca    900
aaaggatttt atggtgaatg tggaaagcga ggtggatatt tccagataga aaatattaat    960
tcatttgctc gttctcagat gtataaaata gcatctacca atttatgttc aaatgtagtt   1020
ggtcaagaga tggttgaaat aatttgcaac ccaccaaaag aaggtgatga atcttatcca   1080
aaatacatga atgaaaaaat gtctatttta aactctttga aaagaaaagc caagttactc   1140
tattctgttc taaatgagtg tgaaggaatt tcttgtaatg aagctatggg tgctctttat   1200
cttttcccaa agattacatt cccaaacaaa tatattgatg agtgtaaaag aaaggatcaa   1260
aaaccagatg aattgtattg tttaaggatg ttaaaaagta tagggggtgtg tgttgttcca   1320 ggatctggtt ttggtcaaaa agataatacg tatcatttta gaattgccat tctaccacca   1380
gaaaatgaaa tacagaatat tgccgtcaaa ataaaaactt ttcatacatc ttttatgaag   1440
gactattgtc actaa                                                    1455
```

<210> SEQ ID NO 50
<211> LENGTH: 484
<212> TYPE: PRT
<213> ORGANISM: Entamoeba histolytica

<400> SEQUENCE: 50

```
Met Lys Ala Phe Ser Arg Gln Ser Ile Asn Pro Cys Ile Ile Ala Thr
1               5                   10                  15

Gln Tyr Ala Val Arg Gly Lys Leu Val Leu Glu Ala Asn Glu Ile Gln
            20                  25                  30

Lys Glu Ile Glu Glu Ala Arg Lys Lys Gly Lys Asn Asn Pro Tyr Pro
        35                  40                  45

Phe Glu Lys Val Val Tyr Cys Asn Ile Gly Asn Pro Gln Ile Cys Asn
    50                  55                  60

Gln Gln Pro Leu Thr Tyr Pro Arg Gln Ile Ile Ser Ile Val Glu Tyr
65                  70                  75                  80

Pro Glu Leu Leu Asn His Thr Thr Leu Phe Pro Lys Asp Val Ile Thr
                85                  90                  95

His Ala Lys Lys Ile Ile Asn Ser Leu Gly Cys Thr Gly Thr Ser Gly
            100                 105                 110

Ala Tyr Thr Asn Ser Met Gly Val Ile Gln Phe Arg Lys Ser Ile Cys
        115                 120                 125

Lys Phe Ile Lys His Arg Asp Gly Thr Ala Pro Ser Pro Asp Asp Val
    130                 135                 140

Phe Ile Thr Asp Gly Ala Ser Thr Gly Ile Lys Met Ile Leu Asn Met
145                 150                 155                 160

Leu Ile Ser His Pro Leu His Gly Ile Met Ile Pro Ile Pro Gln Tyr
                165                 170                 175

Pro Leu Tyr Ser Ala Ser Ile Ser Gln Phe Gly Gly Phe Gln Ile Asn
            180                 185                 190

Tyr Phe Leu Asp Glu Ser Lys Lys Trp Ser Thr Asp Met Thr Ser Val
        195                 200                 205
```

Arg Lys Val Tyr Glu Gln Ala Val Glu Lys Gly Ile Gln Val Lys Gly
    210                 215                 220

Phe Val Cys Ile Asn Pro Gly Asn Pro Thr Gly Gln Val Leu Thr Val
225                 230                 235                 240

Gln Asn Met Lys Glu Ile Ile Glu Phe Cys Tyr Glu Lys Lys Ile Cys
                245                 250                 255

Leu Leu Ala Asp Glu Val Tyr Gln Glu Asn Ile Tyr Gly Glu Ile Pro
            260                 265                 270

Phe Thr Ser Phe Arg Lys Val Leu Lys Ser Met Arg Asp Glu Val Lys
        275                 280                 285

Asn Ser Val Glu Leu Ile Ser Phe Phe Ser Val Ser Lys Gly Phe Tyr
    290                 295                 300

Gly Glu Cys Gly Lys Arg Gly Tyr Phe Gln Ile Glu Asn Ile Asn
305                 310                 315                 320

Ser Phe Ala Arg Ser Gln Met Tyr Lys Ile Ala Ser Thr Asn Leu Cys
                325                 330                 335

Ser Asn Val Val Gly Gln Glu Met Val Glu Ile Ile Cys Asn Pro Pro
            340                 345                 350

Lys Glu Gly Asp Glu Ser Tyr Pro Lys Tyr Met Asn Glu Lys Met Ser
        355                 360                 365

Ile Leu Asn Ser Leu Lys Arg Lys Ala Lys Leu Leu Tyr Ser Val Leu
    370                 375                 380

Asn Glu Cys Glu Gly Ile Ser Cys Asn Glu Ala Met Gly Ala Leu Tyr
385                 390                 395                 400

Leu Phe Pro Lys Ile Thr Phe Pro Asn Lys Tyr Ile Asp Glu Cys Lys
                405                 410                 415

Arg Lys Asp Gln Lys Pro Asp Glu Leu Tyr Cys Leu Arg Met Leu Lys
            420                 425                 430

Ser Ile Gly Val Cys Val Val Pro Gly Ser Gly Phe Gly Gln Lys Asp
        435                 440                 445

Asn Thr Tyr His Phe Arg Ile Ala Ile Leu Pro Pro Glu Asn Glu Ile
    450                 455                 460

Gln Asn Ile Ala Val Lys Ile Lys Thr Phe His Thr Ser Phe Met Lys
465                 470                 475                 480

Asp Tyr Cys His

<210> SEQ ID NO 51
<211> LENGTH: 1452
<212> TYPE: DNA
<213> ORGANISM: Entamoeba histolytica

<400> SEQUENCE: 51
atgagatcat tcgctagtga aaatattagt ccagatgtag ttgcattcca atttgctgta      60
cgtggtaaaa ttgctattgt ttcagaagaa attgataatg ctattaaaaa agcaaaagca     120
gaaggtaaac caaatcctta tccatttgaa aaagttgtta atgtaatag tggtaatcct     180 caattattaa atcaaaaacc attaactttt gttagagaaa ttacttctat ggtagaatat     240
cctcctctta cagaacatcc agaacttttc catgctgatg ctgttgctcg tgctaaagaa     300
attattaaag ctactggttg taatggaaca actggtgctt actcaccatc taaaggtctt     360
gcttatgtta gacaaacaat tgcacgtttc ttagaagaaa gagataatgt tccaatgtcc     420
ccagaagata tttatttaac tgatggtgct ctattgcta ttaagattgt tatgcaatta     480
atgctttcac atccacttca tggtattatg attccaaatc cacaatatcc attatatggt     540

-continued

```
gcttgtattc aacaattagg aggaaaaaca tgtcattata atttaaacga agataattat    600
tggttaccag acattaatga tattaaggaa caatatgaaa aatatcagaa tgaaggaatt    660
aaaattaagg cattagttgt tattaatcca ggaaatccat gtggagaagt tttaccagtt    720
gacactataa aagaaattat tagattctgt aacgaaaaga agatttgttt aatggctgat    780
gaagtatatc aagaaatat ttggactgat gttccattca actcatttag aaaaattctt    840
gctacaatgg aaccagaaat tgcacatgga cttgaattaa tttctttcca ttctatttca    900
aaaggattct atggagaatg tggtaagaga ggaggaatgt ttgcatgtac caatattcca    960
gaatttgctc gtttaatgat gtataaaatt atttctacta ctttatgttc taatgttgta   1020
ggacaagttg taatgtctat aatttgtaat cttccaaaag aaggagaccc atcctatcca   1080
ttatttaaac aagaaagaga tgaaatcctt ggctctttaa aacgtaaagc agaatattta   1140
tgtgatattt tcaataagtg tgaaggtatg tcttgtaata gagctgctgg agctatgtat   1200
cttttcccaa gaattacatt accagaaaaa ttcataaaag aatgtcatga agacatgaa    1260 gatccaaatg aaacatattg tattgaaatg ttaaaaaaga ctggaattgc tgttgtaaaa   1320
gggtctggat ttggtcagaa aaagggtaca tatcatttta gaattgcttt gttaccacca   1380
gaaaatgaaa ttgaagaagt tggaaaaaga attcaagtat tccataattc tttttattcaa   1440 caatacaagt aa                                                       1452
```

<210> SEQ ID NO 52
<211> LENGTH: 483
<212> TYPE: PRT
<213> ORGANISM: Entamoeba histolytica

<400> SEQUENCE: 52

```
Met Arg Ser Phe Ala Ser Glu Asn Ile Ser Pro Asp Val Val Ala Phe
1               5                   10                  15

Gln Phe Ala Val Arg Gly Lys Ile Ala Ile Val Ser Glu Glu Ile Asp
            20                  25                  30

Asn Ala Ile Lys Lys Ala Lys Ala Glu Gly Lys Pro Asn Pro Tyr Pro
        35                  40                  45

Phe Glu Lys Val Val Lys Cys Asn Ser Gly Asn Pro Gln Leu Leu Asn
    50                  55                  60

Gln Lys Pro Leu Thr Phe Val Arg Glu Ile Thr Ser Met Val Glu Tyr
65                  70                  75                  80

Pro Pro Leu Thr Glu His Pro Glu Leu Phe His Ala Asp Ala Val Ala
                85                  90                  95

Arg Ala Lys Glu Ile Ile Lys Ala Thr Gly Cys Asn Gly Thr Thr Gly
            100                 105                 110

Ala Tyr Ser Pro Ser Lys Gly Leu Ala Tyr Val Arg Gln Thr Ile Ala
        115                 120                 125

Arg Phe Leu Glu Glu Arg Asp Asn Val Pro Met Ser Pro Glu Asp Ile
    130                 135                 140

Tyr Leu Thr Asp Gly Ala Ser Ile Ala Ile Lys Ile Val Met Gln Leu
145                 150                 155                 160

Met Leu Ser His Pro Leu His Gly Ile Met Ile Pro Asn Pro Gln Tyr
                165                 170                 175

Pro Leu Tyr Gly Ala Cys Ile Gln Gln Leu Gly Gly Lys Thr Cys His
            180                 185                 190

Tyr Asn Leu Asn Glu Asp Asn Tyr Trp Leu Pro Asp Ile Asn Asp Ile
        195                 200                 205

Lys Glu Gln Tyr Glu Lys Tyr Gln Asn Glu Gly Ile Lys Ile Lys Ala
```

```
                210                 215                 220
Leu Val Val Ile Asn Pro Gly Asn Pro Cys Gly Glu Val Leu Pro Val
225                 230                 235                 240

Asp Thr Ile Lys Glu Ile Ile Arg Phe Cys Asn Glu Lys Lys Ile Cys
                245                 250                 255

Leu Met Ala Asp Glu Val Tyr Gln Glu Asn Ile Trp Thr Asp Val Pro
                260                 265                 270

Phe Asn Ser Phe Arg Lys Ile Leu Ala Thr Met Glu Pro Glu Ile Ala
                275                 280                 285

His Gly Leu Glu Leu Ile Ser Phe His Ser Ile Ser Lys Gly Phe Tyr
                290                 295                 300

Gly Glu Cys Gly Lys Arg Gly Gly Met Phe Ala Cys Thr Asn Ile Pro
305                 310                 315                 320

Glu Phe Ala Arg Leu Met Met Tyr Lys Ile Ile Ser Thr Thr Leu Cys
                325                 330                 335

Ser Asn Val Val Gly Gln Val Val Met Ser Ile Ile Cys Asn Leu Pro
                340                 345                 350

Lys Glu Gly Asp Pro Ser Tyr Pro Leu Phe Lys Gln Glu Arg Asp Glu
                355                 360                 365

Ile Leu Gly Ser Leu Lys Arg Lys Ala Glu Tyr Leu Cys Asp Ile Phe
370                 375                 380

Asn Lys Cys Glu Gly Met Ser Cys Asn Arg Ala Gly Ala Met Tyr
385                 390                 395                 400

Leu Phe Pro Arg Ile Thr Leu Pro Glu Lys Phe Ile Lys Glu Cys His
                405                 410                 415

Glu Arg His Glu Asp Pro Asn Glu Thr Tyr Cys Ile Glu Met Leu Lys
                420                 425                 430

Lys Thr Gly Ile Ala Val Val Lys Gly Ser Gly Phe Gly Gln Lys Lys
                435                 440                 445

Gly Thr Tyr His Phe Arg Ile Ala Leu Leu Pro Pro Glu Asn Glu Ile
                450                 455                 460

Glu Glu Val Gly Lys Arg Ile Gln Val Phe His Asn Ser Phe Ile Gln
465                 470                 475                 480

Gln Tyr Lys

<210> SEQ ID NO 53
<211> LENGTH: 1482
<212> TYPE: DNA
<213> ORGANISM: Trypanosoma cruzi

<400> SEQUENCE: 53
atgtctgggt cacgaaagga aattcgcatc aaccccgtg tggtggcggc agagtatgcg      60
gtgcgtggga tgctccccat gcgtgcggac gagatcaggg cggccctggc gacaccggag     120
gggaaggcca agtacccctt ctccagcatt gtgtactgca acattgggaa cccgcaggca     180
ctggaacaga agccgctgac gttcttccgg caggtgatgt cgctgattga cgcgccgttc     240
ctgctggaga acgagaaggt tacgtcgcag ttcccggcgg atgcggtggc gcgtgcgagg     300
gagtatcttc gccacatcgg cgatcgcacg ggcgcctaca cggactctgc gggctacgcc     360
tttgtccgtg acatcgtggc gcggcaaatc aatgaacgcg accacgagat aaagccgctg     420
gtggacgcat cctctatttt tctgacggac ggcgcgagct cgggcgtgcg tcttttgctg     480
caggttctcg tgggtgacgc gagtgatgcg gtgatggttc ccattccgca gtacccgctg     540
tacacggcgc agcttacgct tcttggcggc acgcccgcga tgtactacct gtgtgagaag     600
```

-continued

```
gataactggg cactgaacgt ggaggagctg gcgtcggtgt acgacgagtg cgtggcgaag    660
aataatgcga ccccgcgcgt gctcgttgtg atcaaccctg gaacccgac tggcggcgtg     720 ctggatcgcg acgtgatgga ggccgtggcg aaattctgct gcgaccgcgg cattgtgctg    780
atggcggacg aggtgtacca ggagaacgtg tacgcggcgg gaaagcgttt cttgagcttc    840
cgggaagtgg tgcttgggct gccggcgccg tacaacacgg acacggtgct ggcctcgctg    900
cactcgacgt cgaagggcat cattggtgag tgcgggcgcc gcggcgggta cttctgcctc    960
acaaacttcc ccgcgccggt cgggagcag gtgttaaaga tgtgctccat ggttccgtgc    1020
agcagcgtga atgggcagtt gatgacggca ctgatgtgct cgccaccgcg gcccggtgac   1080
gcgagctatg agtcatactg ggcggagtac aatgggatct ttgcgagtct aaagaagcgc   1140
gccctgctgc ttgcgaagga gctgagcacg attcgcggtt tttcttgcca gccggtggaa   1200
ggggcgatgt acgcgtttcc gacgattgag ctgccggaga agtactttca gcacaatgag   1260
gagctgaacg cgaaggaggg gcgaaagctt gggcccgaca cgcgatgggc gttggagctt   1320
ctggagagca gcggggttgt tgttgtggcc ggctctgggt ttggtcagca gcccaacacg   1380
ctgcacttcc gcacgacgat cctgccgccg gagcagcaga tggaacggat ggtgaaggcg   1440
atgcgcacat tccaggaggg catttgggca aagtacgggt aa                     1482
```

<210> SEQ ID NO 54
<211> LENGTH: 493
<212> TYPE: PRT
<213> ORGANISM: Trypanosoma cruzi

<400> SEQUENCE: 54

```
Met Ser Gly Ser Arg Lys Glu Ile Arg Ile Asn Pro Arg Val Val Ala
1               5                   10                  15

Ala Glu Tyr Ala Val Arg Gly Met Leu Pro Met Arg Ala Asp Glu Ile
            20                  25                  30

Arg Ala Ala Leu Ala Thr Pro Glu Gly Lys Ala Lys Tyr Pro Phe Ser
        35                  40                  45

Ser Ile Val Tyr Cys Asn Ile Gly Asn Pro Gln Ala Leu Glu Gln Lys
    50                  55                  60

Pro Leu Thr Phe Phe Arg Gln Val Met Ser Leu Ile Asp Ala Pro Phe
65                  70                  75                  80

Leu Leu Glu Asn Glu Lys Val Thr Ser Gln Phe Pro Ala Asp Ala Val
                85                  90                  95

Ala Arg Ala Arg Glu Tyr Leu Arg His Ile Gly Asp Arg Thr Gly Ala
            100                 105                 110

Tyr Thr Asp Ser Ala Gly Tyr Ala Phe Val Arg Asp Ile Val Ala Arg
        115                 120                 125

Gln Ile Asn Glu Arg Asp His Glu Ile Lys Pro Leu Val Asp Ala Ser
    130                 135                 140

Ser Ile Phe Leu Thr Asp Gly Ala Ser Ser Gly Val Arg Leu Leu Leu
145                 150                 155                 160

Gln Val Leu Val Gly Asp Ala Ser Asp Ala Val Met Val Pro Ile Pro
                165                 170                 175

Gln Tyr Pro Leu Tyr Thr Ala Gln Leu Thr Leu Leu Gly Gly Thr Pro
            180                 185                 190

Ala Met Tyr Tyr Leu Cys Glu Lys Asp Asn Trp Ala Leu Asn Val Glu
        195                 200                 205

Glu Leu Ala Ser Val Tyr Asp Glu Cys Val Ala Lys Asn Asn Ala Thr
    210                 215                 220
```

Pro Arg Val Leu Val Val Ile Asn Pro Gly Asn Pro Thr Gly Gly Val
225                 230                 235                 240

Leu Asp Arg Asp Val Met Glu Ala Val Ala Lys Phe Cys Cys Asp Arg
            245                 250                 255

Gly Ile Val Leu Met Ala Asp Glu Val Tyr Gln Glu Asn Val Tyr Ala
        260                 265                 270

Ala Gly Lys Arg Phe Leu Ser Phe Arg Glu Val Val Leu Gly Leu Pro
    275                 280                 285

Ala Pro Tyr Asn Thr Asp Thr Val Leu Ala Ser Leu His Ser Thr Ser
290                 295                 300

Lys Gly Ile Ile Gly Glu Cys Gly Arg Gly Gly Tyr Phe Cys Leu
305                 310                 315                 320

Thr Asn Phe Pro Ala Pro Val Arg Glu Gln Val Leu Lys Met Cys Ser
            325                 330                 335

Met Val Pro Cys Ser Ser Val Asn Gly Gln Leu Met Thr Ala Leu Met
        340                 345                 350

Cys Ser Pro Pro Arg Pro Gly Asp Ala Ser Tyr Glu Ser Tyr Trp Ala
    355                 360                 365

Glu Tyr Asn Gly Ile Phe Ala Ser Leu Lys Lys Arg Ala Leu Leu Leu
370                 375                 380

Ala Lys Glu Leu Ser Thr Ile Arg Gly Phe Ser Cys Gln Pro Val Glu
385                 390                 395                 400

Gly Ala Met Tyr Ala Phe Pro Thr Ile Glu Leu Pro Glu Lys Tyr Phe
            405                 410                 415

Gln His Asn Glu Glu Leu Asn Ala Lys Glu Gly Arg Lys Leu Gly Pro
        420                 425                 430

Asp Thr Arg Trp Ala Leu Glu Leu Leu Glu Ser Ser Gly Val Val Val
    435                 440                 445

Val Ala Gly Ser Gly Phe Gly Gln Gln Pro Asn Thr Leu His Phe Arg
450                 455                 460

Thr Thr Ile Leu Pro Pro Glu Gln Gln Met Glu Arg Met Val Lys Ala
465                 470                 475                 480

Met Arg Thr Phe Gln Glu Gly Ile Trp Ala Lys Tyr Gly
            485                 490

<210> SEQ ID NO 55
<211> LENGTH: 1494
<212> TYPE: DNA
<213> ORGANISM: Trypanosoma cruzi

<400> SEQUENCE: 55
atgctgcgca aaactctttt tggattcagg gccattcgca tcaaccccg tgtggtggcg    60 gcagagtatg cggtgcgtgg gatgctccca atgcgtgcgg acgagatcag ggcggccctg   120
gcgacaccgg aggggaaggc caagtatccc ttccccagca ttgtgtactg caacattggg   180
aacccgcagg cactggaaca gaagccgctg acgttcttcc ggcaggtgat gtcgctgatt   240
gacgcgccgt cctgctggaa aacgagaag gttacgtcgc agtacccggc ggatgcggtg   300
gcgcgtgcga gggagtatct tcgccacatc ggcgatcgca cgggcgccta acgggactct   360
gcgggctacg cctttgtccg tgacatcgtg gcgcggcaaa tcaatgaacg cgaccacgag   420
ataaagccgc tggtggacgc atcctctatt tttctgacgg acggcgcgag ctcgggcgtg   480
cgtcttttgc tgcaggttct cgtgggtgac gcgagtgatg cggtgatggt tccattccg   540 cagtacccgc tgtacacggc gcagcttacg cttcttggcg gcacgcccgc gatgtactac   600
ctgtgtgaga aggataactg ggcactgaac gtggaggagc tggcgtcggt gtacgacgag   660

-continued

```
tgcgtggcga agaataatgc gactccgcgc gtgctcgttg tgatcaaccc tgggaacccg      720
actggcggcg tgctggatcg cgacgtgatg gaggctgtgg cgaaattctg ctgcgaccgc      780
ggcattgtgc tgatggcgga cgaggtgtac caggagaacg tgtacgcggc gggaaagcgt      840
ttcttgagct tccgggaagt ggtgcttggg ctgccggcgc cgtacaacac ggacacggtg      900
ctggcctcgc tgcactcgac gtcgaagggc atcattggtg agtgcgggcg ccgcggcggg      960
tacttctgcc tcacaaactt ccccgcgccg gttcgggagc aggtgttaaa gatgtgctcc     1020
atggttccgt gcagcagcgt gaatgggcag ttgatgacgg cactgatgtg ctcgccaccg     1080
cggcccggtg acgcgagcta tgagtcatac tgggcggagt acaatgggat ctttgcgagt     1140
ctaaagaagc gcgccctgct gcttgcgaag gagctgagca cgattcgcgg ttttcttgc      1200 cagccggtgg aagggcgat gtacgcgttt ccgacgattg agctgccgga agtactttt      1260 cagcacaatg aggagctgaa cgcgaaggag gggcgaaagc ttgggcccga cacgcgatgg     1320
gcgttggagc ttctggagag cagcgggtt gttgttgtgg ccggctctgg gtttggtcag      1380
cagcccaaca cgctgcactt ccgcacgacg atcctgccgc cggagcagca gatggaacgg     1440
atggtgaagg cgatgcgcac attccaggag ggcatttggg caaagtacgg gtaa           1494
```

<210> SEQ ID NO 56
<211> LENGTH: 497
<212> TYPE: PRT
<213> ORGANISM: Trypanosoma cruzi

<400> SEQUENCE: 56

```
Met Leu Arg Lys Thr Leu Phe Gly Phe Arg Ala Ile Arg Ile Asn Pro
1               5                   10                  15

Arg Val Val Ala Ala Glu Tyr Ala Val Arg Gly Met Leu Pro Met Arg
            20                  25                  30

Ala Asp Glu Ile Arg Ala Ala Leu Ala Thr Pro Glu Gly Lys Ala Lys
        35                  40                  45

Tyr Pro Phe Pro Ser Ile Val Tyr Cys Asn Ile Gly Asn Pro Gln Ala
    50                  55                  60

Leu Glu Gln Lys Pro Leu Thr Phe Phe Arg Gln Val Met Ser Leu Ile
65                  70                  75                  80

Asp Ala Pro Phe Leu Leu Glu Asn Glu Lys Val Thr Ser Gln Tyr Pro
                85                  90                  95

Ala Asp Ala Val Ala Arg Ala Arg Glu Tyr Leu Arg His Ile Gly Asp
            100                 105                 110

Arg Thr Gly Ala Tyr Thr Asp Ser Ala Gly Tyr Ala Phe Val Arg Asp
        115                 120                 125

Ile Val Ala Arg Gln Ile Asn Glu Arg Asp His Glu Ile Lys Pro Leu
    130                 135                 140

Val Asp Ala Ser Ser Ile Phe Leu Thr Asp Gly Ala Ser Ser Gly Val
145                 150                 155                 160

Arg Leu Leu Leu Gln Val Leu Gly Asp Ala Ser Asp Ala Val Met
            165                 170                 175

Val Pro Ile Pro Gln Tyr Pro Leu Tyr Thr Ala Gln Leu Thr Leu Leu
            180                 185                 190

Gly Gly Thr Pro Ala Met Tyr Tyr Leu Cys Glu Lys Asp Asn Trp Ala
        195                 200                 205

Leu Asn Val Glu Glu Leu Ala Ser Val Tyr Asp Glu Cys Val Ala Lys
    210                 215                 220

Asn Asn Ala Thr Pro Arg Val Leu Val Val Ile Asn Pro Gly Asn Pro
```

```
                 225                 230                 235                 240
Thr Gly Gly Val Leu Asp Arg Asp Val Met Glu Ala Val Ala Lys Phe
                     245                 250                 255
Cys Cys Asp Arg Gly Ile Val Leu Met Ala Asp Glu Val Tyr Gln Glu
            260                 265                 270
Asn Val Tyr Ala Ala Gly Lys Arg Phe Leu Ser Phe Arg Glu Val Val
        275                 280                 285
Leu Gly Leu Pro Ala Pro Tyr Asn Thr Asp Thr Val Leu Ala Ser Leu
    290                 295                 300
His Ser Thr Ser Lys Gly Ile Ile Gly Glu Cys Gly Arg Arg Gly Gly
305                 310                 315                 320
Tyr Phe Cys Leu Thr Asn Phe Pro Ala Pro Val Arg Glu Gln Val Leu
                325                 330                 335
Lys Met Cys Ser Met Val Pro Cys Ser Ser Val Asn Gly Gln Leu Met
                340                 345                 350
Thr Ala Leu Met Cys Ser Pro Arg Pro Gly Asp Ala Ser Tyr Glu
                355                 360                 365
Ser Tyr Trp Ala Glu Tyr Asn Gly Ile Phe Ala Ser Leu Lys Lys Arg
    370                 375                 380
Ala Leu Leu Leu Ala Lys Glu Leu Ser Thr Ile Arg Gly Phe Ser Cys
385                 390                 395                 400
Gln Pro Val Glu Gly Ala Met Tyr Ala Phe Pro Thr Ile Glu Leu Pro
                405                 410                 415
Glu Lys Tyr Phe Gln His Asn Glu Glu Leu Asn Ala Lys Glu Gly Arg
                420                 425                 430
Lys Leu Gly Pro Asp Thr Arg Trp Ala Leu Glu Leu Leu Glu Ser Ser
                435                 440                 445
Gly Val Val Val Ala Gly Ser Gly Phe Gly Gln Gln Pro Asn Thr
    450                 455                 460
Leu His Phe Arg Thr Thr Ile Leu Pro Pro Glu Gln Gln Met Glu Arg
465                 470                 475                 480
Met Val Lys Ala Met Arg Thr Phe Gln Glu Gly Ile Trp Ala Lys Tyr
                485                 490                 495
Gly

<210> SEQ ID NO 57
<211> LENGTH: 1482
<212> TYPE: DNA
<213> ORGANISM: Trypanosoma cruzi

<400> SEQUENCE: 57
atgtctgggt cacgaaagga aattcgcatc aaccccgtg tggtggcggc agagtatgcg    60
gtgcgtggga tgctccccat gcgtgcggac gagatcaggg cggccctggc gacaccggag  120
gggaaggcca agtaccccct tctccagcat tgtgtactgca acattgggaa cccgcaggca  180
ctggaacaga agccgctgac gttcttccgg caggtgatgt cgctgattga cgcgccgttc  240
ctgctggaga acgagaaggt tacgtcgcag ttcccggcgg atgcggtggc cgtgcgaggg  300
gagtatcttc gccacatcgg cgatcgcacg ggcgcctaca cggactctgc gggctacgcc  360
tttgtccgtg acatcgtggc gcggcaaatc aatgaacgcg accacgagat aaagccgctg  420
gtggacgcat cctctatttt tctgacggac ggcgcgagct cgggcgtgcg tcttttgctg  480
caggttctcg tgggtgacgc gagtgatgcg gtgatggttc ccattccgca gtacccgctg  540
tacacggcgc agcttacgct tcttggcggc acgcccgcga tgtactacct gtgtgagaag  600
```

-continued

```
gataactggg cactgaatgt ggaggagctg gcgtcggtgt acgacgagtg cgtggcgaag    660
aataatgcga ccccgcgcgt gctcgttgtg atcaaccctg gaacccgac tggcggcgtg     720 ctggatcgcg acgtgatgga ggctgtggcg aaattctgct gcgaccgcgg cattgtgctg    780
atggcggacg aggtgtacca ggagaacgtg tacgcggcgg gaaagcgttt cttgagcttc    840
cgggaagtgg tgcttgggct gccggcgccg tacaacacgg acacggtgct ggcctcgctg    900
cactcgacgt cgaagggcat cattggtgag tgcgggcgcc gcggcgggta cttctgcctc    960
acaaacttcc ccgcgccggt gcgggagcag gtggtaaaga tgtgctccat ggttccgtgc   1020
agcagcgtga atgggcagtt gatgacggca ctgatgtgct cgccaccgcg gcccggtgac   1080
gcgagctatg agtcatactg ggcggagtac aatgggatct ttgcgagtct aaagaagcgc   1140
gccctgctgc ttgcgaagga gctgggcacg attcgcggtt tttcttgcca gccggtggaa   1200
ggggcgatgt acgcgtttcc gacgattgag ctgccggaga agtactttca gcacaatgcg   1260
gagctgaacg cgaaggaggg gcgaaagctt gggcccgaca cgcgatgggc gttggagctt   1320
ctggagagca gcggggttgt tgttgtgccc ggctctgggt ttggtcagcg gcccaacacg   1380
ctgcacttcc gcacgacgat cctgccgccg gagcagcaga tggaacggat ggtgaaggcg   1440
atgcgcacat tccaggaggg catttgggca aagtacgggt aa                      1482
```

<210> SEQ ID NO 58
<211> LENGTH: 493
<212> TYPE: PRT
<213> ORGANISM: Trypanosoma cruzi

<400> SEQUENCE: 58

```
Met Ser Gly Ser Arg Lys Glu Ile Arg Ile Asn Pro Arg Val Val Ala
1               5                   10                  15

Ala Glu Tyr Ala Val Arg Gly Met Leu Pro Met Arg Ala Asp Glu Ile
                20                  25                  30

Arg Ala Ala Leu Ala Thr Pro Glu Gly Lys Ala Lys Tyr Pro Phe Ser
            35                  40                  45

Ser Ile Val Tyr Cys Asn Ile Gly Asn Pro Gln Ala Leu Glu Gln Lys
        50                  55                  60

Pro Leu Thr Phe Phe Arg Gln Val Met Ser Leu Ile Asp Ala Pro Phe
65                  70                  75                  80

Leu Leu Glu Asn Glu Lys Val Thr Ser Gln Phe Pro Ala Asp Ala Val
                85                  90                  95

Ala Arg Ala Arg Glu Tyr Leu Arg His Ile Gly Asp Arg Thr Gly Ala
            100                 105                 110

Tyr Thr Asp Ser Ala Gly Tyr Ala Phe Val Arg Asp Ile Val Ala Arg
        115                 120                 125

Gln Ile Asn Glu Arg Asp His Glu Ile Lys Pro Leu Val Asp Ala Ser
    130                 135                 140

Ser Ile Phe Leu Thr Asp Gly Ala Ser Ser Gly Val Arg Leu Leu Leu
145                 150                 155                 160

Gln Val Leu Val Gly Asp Ala Ser Asp Ala Val Met Val Pro Ile Pro
                165                 170                 175

Gln Tyr Pro Leu Tyr Thr Ala Gln Leu Thr Leu Leu Gly Gly Thr Pro
            180                 185                 190

Ala Met Tyr Tyr Leu Cys Glu Lys Asp Asn Trp Ala Leu Asn Val Glu
        195                 200                 205

Glu Leu Ala Ser Val Tyr Asp Glu Cys Val Ala Lys Asn Asn Ala Thr
    210                 215                 220
```

|     |     |     |     |     |     |     |     |     |     |     |     |     |     |     |
|-----|-----|-----|-----|-----|-----|-----|-----|-----|-----|-----|-----|-----|-----|-----|
| Pro | Arg | Val | Leu | Val | Val | Ile | Asn | Pro | Gly | Asn | Pro | Thr | Gly | Gly | Val |
| 225 |     |     |     |     | 230 |     |     |     |     | 235 |     |     |     |     | 240 |

Leu Asp Arg Asp Val Met Glu Ala Val Ala Lys Phe Cys Cys Asp Arg
            245                 250                 255

Gly Ile Val Leu Met Ala Asp Glu Val Tyr Gln Glu Asn Val Tyr Ala
            260                 265                 270

Ala Gly Lys Arg Phe Leu Ser Phe Arg Glu Val Val Leu Gly Leu Pro
        275                 280                 285

Ala Pro Tyr Asn Thr Asp Thr Val Leu Ala Ser Leu His Ser Thr Ser
    290                 295                 300

Lys Gly Ile Ile Gly Glu Cys Gly Arg Arg Gly Gly Tyr Phe Cys Leu
305                 310                 315                 320

Thr Asn Phe Pro Ala Pro Val Arg Glu Gln Val Val Lys Met Cys Ser
                325                 330                 335

Met Val Pro Cys Ser Ser Val Asn Gly Gln Leu Met Thr Ala Leu Met
            340                 345                 350

Cys Ser Pro Pro Arg Pro Gly Asp Ala Ser Tyr Glu Ser Tyr Trp Ala
        355                 360                 365

Glu Tyr Asn Gly Ile Phe Ala Ser Leu Lys Lys Arg Ala Leu Leu Leu
    370                 375                 380

Ala Lys Glu Leu Gly Thr Ile Arg Gly Phe Ser Cys Gln Pro Val Glu
385                 390                 395                 400

Gly Ala Met Tyr Ala Phe Pro Thr Ile Glu Leu Pro Glu Lys Tyr Phe
                405                 410                 415

Gln His Asn Ala Glu Leu Asn Ala Lys Glu Gly Arg Lys Leu Gly Pro
            420                 425                 430

Asp Thr Arg Trp Ala Leu Glu Leu Leu Glu Ser Ser Gly Val Val Val
        435                 440                 445

Val Pro Gly Ser Gly Phe Gly Gln Arg Pro Asn Thr Leu His Phe Arg
    450                 455                 460

Thr Thr Ile Leu Pro Pro Glu Gln Gln Met Glu Arg Met Val Lys Ala
465                 470                 475                 480

Met Arg Thr Phe Gln Glu Gly Ile Trp Ala Lys Tyr Gly
                485                 490

<210> SEQ ID NO 59
<211> LENGTH: 1494
<212> TYPE: DNA
<213> ORGANISM: Trypanosoma cruzi

<400> SEQUENCE: 59

| | | | | |
|---|---|---|---|---|
| atgctacgca | aaacccttt | tggattcagg | gccattcgca | tcaaccccg | tgtggtggcg | 60 |
| gcagagtatg | cggtgcgtgg | gatgctcccc | atgcgtgcgg | acgagatcag | ggcggccctg | 120 |
| gcgacaccgg | aggggaaggc | caagtacccc | ttctccagca | ttgtgtactg | caacattggg | 180 |
| aacccgcagg | cactggaaca | gaagccgctg | acgttcttcc | ggcaggtgat | gtcgctgatt | 240 |
| gacgcgccgt | cctgctgga | gaacgagaag | gttacgtcgc | agttcccggc | ggatgcggtg | 300 |
| gcgcgtgcga | gggagtatct | tcgccacatc | ggcgatcgca | cgggcgccta | cacggactct | 360 |
| gcgggctacg | cctttgcccg | tgacatcgtg | gcgcggcaaa | tcaatgaacg | cgaccacgag | 420 |
| ataaagccgc | tggtggacgc | atcctctatt | tttctgacgg | acggcgcgag | ctcgggcgtg | 480 |
| cgtcttttgc | tgcaggttct | cgtgggtgac | gcgagtgatg | cggtgatggt | tcccattccg | 540 |
| cagtacccgc | tgtacacggc | gcagcttact | cttcttggcg | gcacgcccgc | gatgtactac | 600 |
| ctgtgtgaga | aggataactg | ggcactgaac | gtggaggagc | tggcgtcggt | gtacgacgag | 660 |

-continued

```
tgcgtggcga agaataatgc gaccccgcgc gtgctcgttg tgatcaaccc cgggaacccg    720
actggcggcg tgctggatcg cgaagtgatg gaggccgtgg cgaaattctg ctgcgaccgc    780
ggcattgtgc tgatggcgga cgaggtgtac caggagaacg tgtacgcggc gggaaagcgt    840
ttcttgagct tccgggaagt ggtgcttggg ctgccggcgc cgtacaacac ggacacggtg    900
ctggcctcgc tgcactcgac gtcgaagggc atcattggtg agtgcgggcg ccgcggcggg    960
tacttctgcc tcacaaactt ccccgcgccg gtgcgggagc aggtggtaaa gatgtgctcc   1020
atggttccgt gcagcagcgt gaatgggcag ttgatgacgg cactgatgtg ctcgccaccg   1080
cggcccggtg acgcgagcta tgagtcatac tgggcggagt acaatgggat ctttgcgagt   1140
ctaaagaagc gcgccctgct gcttgcgaag gagctgggca cgattcgcgg tttttcttgc   1200
cagccggtgg aagggcgat gtacgcgttt ccgacgattg agctgccgga agtactttt    1260 cagcacaatg cggagctgaa cgcgaaggag gggcgaaagc ttgggcccga cacgcgatgg   1320
gcgttggagc ttctggagag cagcgggggtt gttgttgtgc ccggctctgg gtttggtcag   1380
cggcccaaca cgctgcactt ccgcacgacg atcctgccgc cggagcagca gatggaacgg   1440
atggtgaagc gatgcgcac attccaggag ggcatttggg caaagtacgg gtaa           1494
```

<210> SEQ ID NO 60
<211> LENGTH: 497
<212> TYPE: PRT
<213> ORGANISM: Trypanosoma cruzi

<400> SEQUENCE: 60

```
Met Leu Arg Lys Thr Leu Phe Gly Phe Arg Ala Ile Arg Ile Asn Pro
1               5                   10                  15

Arg Val Val Ala Ala Glu Tyr Ala Val Arg Gly Met Leu Pro Met Arg
            20                  25                  30

Ala Asp Glu Ile Arg Ala Ala Leu Ala Thr Pro Glu Gly Lys Ala Lys
        35                  40                  45

Tyr Pro Phe Ser Ser Ile Val Tyr Cys Asn Ile Gly Asn Pro Gln Ala
    50                  55                  60

Leu Glu Gln Lys Pro Leu Thr Phe Phe Arg Gln Val Met Ser Leu Ile
65                  70                  75                  80

Asp Ala Pro Phe Leu Leu Glu Asn Glu Lys Val Thr Ser Gln Phe Pro
                85                  90                  95

Ala Asp Ala Val Ala Arg Ala Arg Glu Tyr Leu Arg His Ile Gly Asp
            100                 105                 110

Arg Thr Gly Ala Tyr Thr Asp Ser Ala Gly Tyr Ala Phe Ala Arg Asp
        115                 120                 125

Ile Val Ala Arg Gln Ile Asn Glu Arg Asp His Glu Ile Lys Pro Leu
    130                 135                 140

Val Asp Ala Ser Ser Ile Phe Leu Thr Asp Gly Ala Ser Ser Gly Val
145                 150                 155                 160

Arg Leu Leu Leu Gln Val Leu Gly Asp Ala Ser Asp Ala Val Met
                165                 170                 175

Val Pro Ile Pro Gln Tyr Pro Leu Tyr Thr Ala Gln Leu Thr Leu Leu
            180                 185                 190

Gly Gly Thr Pro Ala Met Tyr Tyr Leu Cys Glu Lys Asp Asn Trp Ala
        195                 200                 205

Leu Asn Val Glu Glu Leu Ala Ser Val Tyr Asp Glu Cys Val Ala Lys
    210                 215                 220

Asn Asn Ala Thr Pro Arg Val Leu Val Val Ile Asn Pro Gly Asn Pro
```

```
                    225                 230                 235                 240
Thr Gly Gly Val Leu Asp Arg Glu Val Met Glu Ala Val Ala Lys Phe
                245                 250                 255
Cys Cys Asp Arg Gly Ile Val Leu Met Ala Asp Glu Val Tyr Gln Glu
                260                 265                 270
Asn Val Tyr Ala Ala Gly Lys Arg Phe Leu Ser Phe Arg Glu Val Val
                275                 280                 285
Leu Gly Leu Pro Ala Pro Tyr Asn Thr Asp Thr Val Leu Ala Ser Leu
                290                 295                 300
His Ser Thr Ser Lys Gly Ile Ile Gly Glu Cys Gly Arg Arg Gly Gly
305                 310                 315                 320
Tyr Phe Cys Leu Thr Asn Phe Pro Ala Pro Val Arg Glu Gln Val Val
                325                 330                 335
Lys Met Cys Ser Met Val Pro Cys Ser Ser Val Asn Gly Gln Leu Met
                340                 345                 350
Thr Ala Leu Met Cys Ser Pro Pro Arg Pro Gly Asp Ala Ser Tyr Glu
                355                 360                 365
Ser Tyr Trp Ala Glu Tyr Asn Gly Ile Phe Ala Ser Leu Lys Lys Arg
                370                 375                 380
Ala Leu Leu Leu Ala Lys Glu Leu Gly Thr Ile Arg Gly Phe Ser Cys
385                 390                 395                 400
Gln Pro Val Glu Gly Ala Met Tyr Ala Phe Pro Thr Ile Glu Leu Pro
                405                 410                 415
Glu Lys Tyr Phe Gln His Asn Ala Glu Leu Asn Ala Lys Glu Gly Arg
                420                 425                 430
Lys Leu Gly Pro Asp Thr Arg Trp Ala Leu Glu Leu Leu Glu Ser Ser
                435                 440                 445
Gly Val Val Val Pro Gly Ser Gly Phe Gly Gln Arg Pro Asn Thr
                450                 455                 460
Leu His Phe Arg Thr Thr Ile Leu Pro Pro Glu Gln Gln Met Glu Arg
465                 470                 475                 480
Met Val Lys Ala Met Arg Thr Phe Gln Glu Gly Ile Trp Ala Lys Tyr
                485                 490                 495
Gly
```

<210> SEQ ID NO 61
<211> LENGTH: 1869
<212> TYPE: DNA
<213> ORGANISM: Cricetulus griseus

<400> SEQUENCE: 61

```
atggccacca aggagaagct gcagtgtctg aaagacttcc acaaagacat cctgaagcct       60
tctccaggga agagcccagg cacacggcct gaggatgagg ctgaggggaa gccccctcag      120
agggagaagt ggtccagcaa gattgacttt gtgctgtctg tggccggagg cttcgtgggt      180
ttgggcaacg tttggcgttt cccgtacctc tgctacaaaa atggtggagg tgctttcctc      240
ataccgtatt ttattttcct gtttggggagt ggcctgcctg tgttttttcct ggaggtcata      300
ataggccagt acacctcaga agggggaatc acctgctggg agaagatctg ccccttgttc      360
tctggcattg ctacgcatc catcgtcatc gtgtccctcc tgaatgtgta ctacattgtc      420
atcctggcct gggccacata ctacctattt cactccttcc agacagagct tccctgggcc      480
cactgcaacc acagctggaa cacaccacat tgcatggagg acaccctgcg taggaatgag      540
agtctctggg tctcccttag cgcctccaac ttcacctcgc tgtcatcga gttctgggag      600
```

```
cgcaatgtac tcagcctgtc ttccggaatc gacgaaccag gcgctctgaa atgggacctt    660
gcgctctgcc tcctcttagt ctggcttgtc tgttttttct gcatatggaa gggtgttcga    720
tccacaggca aggttgtcta cttcaccgcc actttcccgt ttgccatgct tctggtgctg    780
ctggtccgtg gactgaccct gccgggtgct ggcgaaggca tcaaattcta cctgtaccct    840
gacatcagcc gccttgagga cccacaggtg tggatcgacg ccggaaccca gatattcttt    900
tcctatgcca tctgcctggg ggccatgacc tcactgggaa gctacaacaa gtacaagtat    960
aactcgtaca gggactgtat gctgctggga tgcctgaaca gtggtaccag ttttgtgtct   1020
ggcttcgcag tttttttccat cctgggcttc atggcacaag agcaagggg ggacattgct   1080
gatgtggctg agtcaggtcc tggcttggcc ttcattgcct atccaaaagc tgtgactatg   1140
atgccgctgc ccacctttg gtccattctg tttttatta tgctcctctt gcttggactg   1200
gacagccagt ttgttgaagt cgaaggacag atcacatcct tggttgatct ttacccgtcc   1260
ttcctaagga agggttatcg tcgggaagtc ttcatcgcca tcctgtgtag catcagctac   1320
ctgctggggc tgtcgatggt gacggagggt ggcatgtatg tgtttcaact ctttgactac   1380
tatgcagcta gtggtgtatg ccttttgtgg gttgcattct ttgaatgttt tgttattgcc   1440
tggatatatg gtggtgataa cttatatgac ggtattgagg acatgattgg ctatcggcct   1500
gggccctgga tgaagtacag ctgggctgtc atcactccag ttctctgtgc tggatgtttc   1560
atcttctctc ttgtcaagta tgtaccctg acctacaaca agtctacgt gtatcctgat   1620
tgggcaattg gctgggctg gggcctggcc ctatcctcca tggtgtgtat cccttggtc   1680
attgccatcc tcctctgccg gacggaggga ccgttccgcg tgagaatcca ataccctgata   1740
acccccaggg agcccaaccg ctgggctgtg agcgtgagg gggccacacc cttccactcc   1800
cgcacaagcc tcgtcatgaa cggcgcactc atgaaaccca gtcacgtcat tgtggagacc   1860
atgatgtga                                                           1869
```

<210> SEQ ID NO 62
<211> LENGTH: 622
<212> TYPE: PRT
<213> ORGANISM: Cricetulus griseus

<400> SEQUENCE: 62

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Ile Val Ile Leu Ala Trp
    130                 135                 140

Ala Thr Tyr Tyr Leu Phe His Ser Phe Gln Thr Glu Leu Pro Trp Ala

```
            145                 150                 155                 160
His Cys Asn His Ser Trp Asn Thr Pro His Cys Met Glu Asp Thr Leu
                165                 170                 175

Arg Arg Asn Glu Ser Leu Trp Val Ser Leu Ser Ala Ser Asn Phe Thr
                180                 185                 190

Ser Pro Val Ile Glu Phe Trp Glu Arg Asn Val Leu Ser Leu Ser Ser
                195                 200                 205

Gly Ile Asp Glu Pro Gly Ala Leu Lys Trp Asp Leu Ala Leu Cys Leu
                210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
                260                 265                 270

Gly Ile Lys Phe Tyr Leu Tyr Pro Asp Ile Ser Arg Leu Glu Asp Pro
                275                 280                 285

Gln Val Trp Ile Asp Ala Gly Thr Gln Ile Phe Phe Ser Tyr Ala Ile
                290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Val Phe Ser Ile Leu Gly Phe Met Ala
                340                 345                 350

Gln Glu Gln Gly Val Asp Ile Ala Asp Val Ala Glu Ser Gly Pro Gly
                355                 360                 365

Leu Ala Phe Ile Ala Tyr Pro Lys Ala Val Thr Met Met Pro Leu Pro
                370                 375                 380

Thr Phe Trp Ser Ile Leu Phe Phe Ile Met Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Val Phe Ile
                420                 425                 430

Ala Ile Leu Cys Ser Ile Ser Tyr Leu Leu Gly Leu Ser Met Val Thr
                435                 440                 445

Glu Gly Gly Met Tyr Val Phe Gln Leu Phe Asp Tyr Tyr Ala Ala Ser
                450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
                500                 505                 510

Pro Val Leu Cys Ala Gly Cys Phe Ile Phe Ser Leu Val Lys Tyr Val
                515                 520                 525

Pro Leu Thr Tyr Asn Lys Val Tyr Val Tyr Pro Asp Trp Ala Ile Gly
                530                 535                 540

Leu Gly Trp Gly Leu Ala Leu Ser Ser Met Val Cys Ile Pro Leu Val
545                 550                 555                 560

Ile Ala Ile Leu Leu Cys Arg Thr Glu Gly Pro Phe Arg Val Arg Ile
                565                 570                 575
```

| Gln | Tyr | Leu | Ile | Thr | Pro | Arg | Glu | Pro | Asn | Arg | Trp | Ala | Val | Glu | Arg |
|---|---|---|---|---|---|---|---|---|---|---|---|---|---|---|---|
| | | | | 580 | | | | 585 | | | | 590 | | | |

| Glu | Gly | Ala | Thr | Pro | Phe | His | Ser | Arg | Thr | Ser | Leu | Val | Met | Asn | Gly |
|---|---|---|---|---|---|---|---|---|---|---|---|---|---|---|---|
| | 595 | | | | | 600 | | | | 605 | | | | | |

| Ala | Leu | Met | Lys | Pro | Ser | His | Val | Ile | Val | Glu | Thr | Met | Met |
|---|---|---|---|---|---|---|---|---|---|---|---|---|---|
| 610 | | | | | 615 | | | | | 620 | | | |

<210> SEQ ID NO 63
<211> LENGTH: 1866
<212> TYPE: DNA
<213> ORGANISM: Rattus norvegicus

<400> SEQUENCE: 63

```
atggccacca aggagaagct tcaatgtctg aaagacttcc acaaagacat cctgaagcct      60
tctccaggga agagcccagg cacgcggcct gaggatgagg ctgatgggaa gccccctcag     120
agggagaagt ggtccagcaa gatcgacttt gtgctgtctg tggccggagg cttcgtgggt     180
ttgggcaatg tctggcgttt cccgtacctc tgctacaaaa atggtggagg tgcattcctc     240
ataccgtatt ttatttttcct gtttgggagc ggcctgcctg tgttttttcct ggaggtcatc     300
ataggccagt acacctcaga aggggggcatc acctgctggg agaagatctg ccccttgttc     360
tctggcattg gctacgcgtc catcgtcatc gtgtccctcc tgaatgtgta ctacatcgtc     420
atcctggcct gggccacata ctacctattc agtctttcc agaaggatct tccctgggcc     480
cactgcaacc atagctggaa cacgccacag tgcatggagg acaccctgcg taggaacgag     540
agtcactggg tctcccttag cgccgccaac ttcacttcgc ctgtgatcga gttctggag     600
cgcaacgtgc tcagcctgtc ctccggaatc gaccacccag gcagtctgaa atgggacctc     660
gcgctctgcc tcctcttagt ctggctcgtc tgttttttct gcatctggaa gggtgttcgg     720
tccacaggca aggttgtcta cttcactgct actttcccgt ttgccatgct tctggtgctg     780
ctggtccgtg gactgaccct gccaggtgct ggtgaaggca tcaaattcta cctgtaccct     840
aacatcagcc gccttgagga cccacaggtg tggatcgacg ctggaactca gatattcttt     900
tcctacgcta tctgcctggg ggccatgacc tcactgggaa gctataacaa gtacaagtat     960
aactcgtaca gggactgtat gctgctggga tgcctgaaca gtggtaccag ttttgtgtct    1020
ggcttcgcaa ttttttccat cctgggcttc atggcacaag agcaagggggt ggacattgct    1080
gatgtggctg agtcaggtcc tggcttggcc ttcattgcct acccaaaagc tgtgaccatg    1140
atgccgctgc ccacctttg gtccattctg ttttttatta tgctcctctt gcttggactg    1200
gacagccagt ttgttgaagt cgaaggacag atcacatcct tggttgatct ttacccgtcc    1260
ttcctaagga aggttatcg tcgggaaatc ttcattgcca tcgtgtgcag catcagctac    1320
ctgctgggggc tgacgatggt gacggagggt ggcatgtatg tgtttcaact cttttgactac    1380
tatgcagcta gtggtgtatg ccttttgtgg gtcgcattct ttgaatgttt tgttattgcc    1440
tggatatatg gcggtgataa cttatatgac ggtattgagg acatgatcgg ctatcggcct    1500
ggaccctgga tgaagtacag ctgggctgtc atcactccag ctctctgtgt tggatgtttc    1560
atcttctctc tcgtcaagta tgtacccctg acctacaaca aagtctaccg gtaccctgat    1620
tgggcaatcg ggctgggctg gggcctggcc cttttcctcca tggtgtgtat ccccttggtc    1680
attgtcatcc tcctctgccg gacgcgaggga ccgctccgcg tgagaatcaa ataccctgata    1740
accccccaggg agcccaaccg ctgggctgtg gagcgtgaag gggctacgcc ctttcactcc    1800
agagcaaccc tcatgaacgg tgcactcatg aaacccagtc acgtcattgt ggagaccatg    1860
atgtga                                                              1866
```

```
<210> SEQ ID NO 64
<211> LENGTH: 621
<212> TYPE: PRT
<213> ORGANISM: Rattus norvegicus

<400> SEQUENCE: 64

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Asp Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe Gln Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Ala Ala Asn Phe Thr
            180                 185                 190

Ser Pro Val Ile Glu Phe Trp Glu Arg Asn Val Leu Ser Leu Ser Ser
        195                 200                 205

Gly Ile Asp His Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asn Ile Ser Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380
```

Thr Phe Trp Ser Ile Leu Phe Ile Met Leu Leu Leu Gly Leu
385                 390                 395                 400

Asp Ser Gln Phe Val Glu Val Glu Gly Gln Ile Thr Ser Leu Val Asp
            405                 410                 415

Leu Tyr Pro Ser Phe Leu Arg Lys Gly Tyr Arg Glu Ile Phe Ile
        420                 425                 430

Ala Ile Val Cys Ser Ile Ser Tyr Leu Leu Gly Leu Thr Met Val Thr
        435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Ala Leu Cys Val Gly Cys Phe Ile Phe Ser Leu Val Lys Tyr Val
        515                 520                 525

Pro Leu Thr Tyr Asn Lys Val Tyr Arg Tyr Pro Asp Trp Ala Ile Gly
    530                 535                 540

Leu Gly Trp Gly Leu Ala Leu Ser Ser Met Val Cys Ile Pro Leu Val
545                 550                 555                 560

Ile Val Ile Leu Leu Cys Arg Thr Glu Gly Pro Leu Arg Val Arg Ile
                565                 570                 575

Lys Tyr Leu Ile Thr Pro Arg Glu Pro Asn Arg Trp Ala Val Glu Arg
            580                 585                 590

Glu Gly Ala Thr Pro Phe His Ser Arg Ala Thr Leu Met Asn Gly Ala
        595                 600                 605

Leu Met Lys Pro Ser His Val Ile Val Glu Thr Met Met
    610                 615                 620

<210> SEQ ID NO 65
<211> LENGTH: 1866
<212> TYPE: DNA
<213> ORGANISM: Mus musculus

<400> SEQUENCE: 65
atggccacga aggagaagct gcaatgtctg aaagacttcc acaaagacat cctgaagcct    60
tctccaggga gagcccagg cacacggcct gaagatgagg cggacgggaa gccccctcag   120
agggagaagt ggtccagcaa gatcgacttt gtgctgtctg tggccggagg cttcgtgggt   180
ttgggcaacg tctggcgttt cccgtacctc tgctacaaaa atggtggagg tgcgttcctc   240
ataccgtatt ttatttttcct gtttgggagc ggcctgcctg tgttttttctt ggaggtcatc   300 ataggccagt acacatcaga agggggcatc acctgctggg agaagatctg tcctttgttc   360
tctggcattg gctacgcatc catcgtcatt gtgtccctcc tgaacgtgta ctacatcgtc   420
atcctggcct gggccacata ctacctattc cactcttttcc agaaggatct ccctggggcc   480
cactgcaacc atagctggaa cacaccacag tgcatggagg cacccctgcg taggaacgag   540
agtcactggg tctcccttag cactgccaac ttcacctcac ccgtcatcga gttctgggag   600
cgcaatgtgc tcagcctgtc ctccggaatc gacaacccag gcagtctgaa atgggacctc   660
gcgctctgcc tcctcttagt ctggctcgtc tgttttttctt gcatctggaa gggtgttcga   720
tccacaggca aggttgtcta cttcaccgct actttcccgt tgccatgct tctggtgctg   780

-continued

```
ctggtccgtg gactgaccct gccaggtgct ggtgaaggca tcaaattcta cctgtaccct   840
gacatcagcc gccttgggga cccacaggtg tggatcgacg ctggaactca gatattcttt   900
tcctacgcaa tctgcctggg ggccatgacc tcactggaa gctataacaa gtacaagtat    960
aactcgtaca gggactgtat gctgctggga tgcctgaaca gtggtaccag ttttgtgtct  1020
ggcttcgcaa ttttttccat cctgggcttc atggcacaag agcaaggggt ggacattgct  1080
gatgtggctg agtcaggtcc tggcttggcc ttcattgcct acccaaaagc tgtaaccatg  1140
atgccgctgc ccacctttg gtctattctg tttttcatta tgctcctctt gcttggactg  1200
gacagccagt tgttgaagt cgaaggacag atcacatcct tggttgatct ttacccgtcc   1260
ttcctaagga agggttatcg tcgggaaatc ttcatagcca tcttgtgtag catcagctac  1320
ctgctggggc tgacgatggt gacggagggt ggcatgtatg tgtttcaact ctttgactac  1380
tatgcagcta gtggtgtatg cctttgtgg gttgcattct ttgaatgttt tgttattgcc  1440
tggatatatg gcggtgataa cttatatgac ggtattgagg acatgattgg ctatcggcct  1500
gggccctgga tgaagtacag ctgggctgtc atcactccag ctctttgtgt tggatgtttc  1560
gtcttctcgc ttgtcaagta tgtaccctg acctacaaca aagtgtaccg gtacccggat  1620
tgggcaattg ggctgggctg gggcctggcc cttcctcca tgctgtgtat cccttggtc   1680
attgtcatcc tcctctgccg gacggaggga ccgctccgcg tgagaatcaa atacctgata  1740
acccccaggg agcccaaccg ctgggctgtg gagcgtgaag gggccacacc cttcactcc   1800
cgagtaaccc tcatgaacgg cgcactcatg aaacccagtc acgtcattgt ggagaccatg  1860
atgtga                                                              1866
```

<210> SEQ ID NO 66
<211> LENGTH: 621
<212> TYPE: PRT
<213> ORGANISM: Mus musculus

<400> SEQUENCE: 66

```
Met Ala Thr Lys Glu Lys Leu Gln Cys Leu Lys Asp Phe His Lys Asp
1               5                   10                  15

Ile Leu Lys Pro Ser Gly Lys Ser Pro Gly Thr Arg Pro Glu Asp
            20                  25                  30

Glu Ala Asp Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Lys Asp Leu Pro Trp Ala
145                 150                 155                 160

His Cys Asn His Ser Trp Asn Thr Pro Gln Cys Met Glu Asp Thr Leu
                165                 170                 175

Arg Arg Asn Glu Ser His Trp Val Ser Leu Ser Thr Ala Asn Phe Thr
```

-continued

```
                180                 185                 190
Ser Pro Val Ile Glu Phe Trp Glu Arg Asn Val Leu Ser Leu Ser Ser
            195                 200                 205
Gly Ile Asp Asn Pro Gly Ser Leu Lys Trp Asp Leu Ala Leu Cys Leu
        210                 215                 220
Leu Leu Val Trp Leu Val Cys Phe Phe Cys Ile Trp Lys Gly Val Arg
225                 230                 235                 240
Ser Thr Gly Lys Val Val Tyr Phe Thr Ala Thr Phe Pro Phe Ala Met
                245                 250                 255
Leu Leu Val Leu Leu Val Arg Gly Leu Thr Leu Pro Gly Ala Gly Glu
            260                 265                 270
Gly Ile Lys Phe Tyr Leu Tyr Pro Asp Ile Ser Arg Leu Gly Asp Pro
        275                 280                 285
Gln Val Trp Ile Asp Ala Gly Thr Gln Ile Phe Phe Ser Tyr Ala Ile
    290                 295                 300
Cys Leu Gly Ala Met Thr Ser Leu Gly Ser Tyr Asn Lys Tyr Lys Tyr
305                 310                 315                 320
Asn Ser Tyr Arg Asp Cys Met Leu Leu Gly Cys Leu Asn Ser Gly Thr
                325                 330                 335
Ser Phe Val Ser Gly Phe Ala Ile Phe Ser Ile Leu Gly Phe Met Ala
            340                 345                 350
Gln Glu Gln Gly Val Asp Ile Ala Asp Val Ala Glu Ser Gly Pro Gly
        355                 360                 365
Leu Ala Phe Ile Ala Tyr Pro Lys Ala Val Thr Met Met Pro Leu Pro
    370                 375                 380
Thr Phe Trp Ser Ile Leu Phe Phe Ile Met Leu Leu Leu Gly Leu
385                 390                 395                 400
Asp Ser Gln Phe Val Glu Val Glu Gly Gln Ile Thr Ser Leu Val Asp
                405                 410                 415
Leu Tyr Pro Ser Phe Leu Arg Lys Gly Tyr Arg Arg Glu Ile Phe Ile
            420                 425                 430
Ala Ile Leu Cys Ser Ile Ser Tyr Leu Leu Gly Leu Thr Met Val Thr
        435                 440                 445
Glu Gly Gly Met Tyr Val Phe Gln Leu Phe Asp Tyr Tyr Ala Ala Ser
    450                 455                 460
Gly Val Cys Leu Leu Trp Val Ala Phe Phe Glu Cys Phe Val Ile Ala
465                 470                 475                 480
Trp Ile Tyr Gly Gly Asp Asn Leu Tyr Asp Gly Ile Glu Asp Met Ile
                485                 490                 495
Gly Tyr Arg Pro Gly Pro Trp Met Lys Tyr Ser Trp Ala Val Ile Thr
            500                 505                 510
Pro Ala Leu Cys Val Gly Cys Phe Val Phe Ser Leu Val Lys Tyr Val
        515                 520                 525
Pro Leu Thr Tyr Asn Lys Val Tyr Arg Tyr Pro Asp Trp Ala Ile Gly
    530                 535                 540
Leu Gly Trp Gly Leu Ala Leu Ser Ser Met Leu Cys Ile Pro Leu Val
545                 550                 555                 560
Ile Val Ile Leu Leu Cys Arg Thr Glu Gly Pro Leu Arg Val Arg Ile
                565                 570                 575
Lys Tyr Leu Ile Thr Pro Arg Glu Pro Asn Arg Trp Ala Val Glu Arg
            580                 585                 590
Glu Gly Ala Thr Pro Phe His Ser Arg Val Thr Leu Met Asn Gly Ala
        595                 600                 605
```

Leu Met Lys Pro Ser His Val Ile Val Glu Thr Met Met
　　610　　　　　　　615　　　　　　　620

<210> SEQ ID NO 67
<211> LENGTH: 1863
<212> TYPE: DNA
<213> ORGANISM: Homo sapiens

<400> SEQUENCE: 67

| | | | | | |
|---|---|---|---|---|---|
| atggccacca | aggagaagct | gcagtgtctg | aaagatttcc | acaaggacat | cctgaagccc | 60 |
| tcaccaggga | agagcccagg | cacgcggcct | gaggacgagg | ctgagggaaa | acctccgcag | 120 |
| agggagaagt | ggtctagcaa | gatcgacttt | gtgctctctg | tggctggcgg | cttcgtgggc | 180 |
| ttgggcaacg | tctggcgctt | cccgtacctc | tgctacaaga | atggtggagg | tgcgtttctc | 240 |
| ataccgtatt | ttattttcct | gtttgggagc | ggcctgcctg | tgttttctt | ggagatcatc | 300 |
| ataggccagt | acacctctga | aggggcatc | acctgctggg | aaaagatctg | ccccttgttc | 360 |
| tctggtatcg | gctatgcctc | cgttgtaatt | gtgtccctcc | tgaatgtcta | ctacatcgtc | 420 |
| atcctggcct | gggccacata | ctacctgttc | cagtccttcc | agaaggagct | gcctgggca | 480 |
| cactgcaacc | acagctggaa | cacacctcac | tgcatggagg | acaccatgcg | caagaacaag | 540 |
| agtgtctgga | tcaccatcag | ctccaccaac | ttcacctccc | ctgtcatcga | gttctgggag | 600 |
| cgcaacgtgc | tgagcttgtc | ccctggaatc | gaccacccag | gctctctgaa | atgggacctc | 660 |
| gctctctgcc | ttcttttagt | ctggctagtg | tgtttcttct | gcatctggaa | gggcgtcagg | 720 |
| tccactggga | aggtcgtcta | cttcacagcc | acttttccat | cgccatgct | cctggtgctg | 780 |
| ctggtccgag | ggctgacgct | gccgggcgcg | ggcgcaggca | tcaagttcta | tctgtatcct | 840 |
| gacatcaccc | gccttgagga | cccacaggtg | tggattgacg | ctgggactca | gatattcttc | 900 |
| tcttatgcca | tctgcctggg | ggctatgacc | tcgctgggga | gctacaacaa | gtacaagtat | 960 |
| aactcgtaca | gggactgtat | gctgctggga | tgcctgaaca | gtggtaccag | ttttgtgtct | 1020 |
| ggcttcgcaa | tttttccat | cctgggcttc | atggcacaag | agcaaggggt | ggacattgct | 1080 |
| gatgtggctg | agtcaggtcc | tggcctggcc | ttcattgcct | acccaaaagc | tgtgacaatg | 1140 |
| atgccgctgc | ccacatttg | gtccattctt | ttttttatta | tgcttctctt | gcttggactg | 1200 |
| gatagccagt | ttgttgaagt | tgaaggacag | atcacatcct | tggttgatct | ttacccatcc | 1260 |
| ttcctaagga | agggttatcg | tcgggaaatc | ttcatcgcct | tcgtgtgtag | catcagctac | 1320 |
| ctgctggggc | tgacgatggt | gacggagggt | ggcatgtatg | tgtttcagct | ctttgactac | 1380 |
| tatgcagcta | gcggtgtatg | ccttttgtgg | gttgcattct | ttgaatgttt | tgttattgcc | 1440 |
| tggatatatg | gaggtgataa | cctttatgat | ggtattgagg | acatgattgg | ctatcggccc | 1500 |
| gggccctgga | tgaagtacag | ctgggctgtg | atcactccag | ttctctgtgt | tggatgtttc | 1560 |
| atcttctcgc | tcgtcaagta | cgtaccccctg | acctacaaca | aaacatacgt | gtaccccaac | 1620 |
| tgggccattg | ggctgggctg | gagcctggcc | ctttcctcca | tgctctgcgt | tcccttggtc | 1680 |
| atcgtcatcc | gcctctgcca | gactgagggg | ccgttccttg | tgagagtcaa | gtacctgctg | 1740 |
| accccaaggg | aacccaaccg | ctgggctgtg | gagcgcgagg | gagccacacc | ttacaactct | 1800 |
| cgcaccgtca | tgaacggcgc | tctcgtgaaa | ccgacccaca | tcattgtgga | gaccatgatg | 1860 |
| tga | | | | | | 1863 |

<210> SEQ ID NO 68
<211> LENGTH: 620
<212> TYPE: PRT
<213> ORGANISM: Homo sapiens

```
<400> SEQUENCE: 68

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Ile Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Val
            115                 120                 125

Val Ile Val Ser Leu Leu Asn Val Tyr Tyr Ile Val Ile Leu Ala Trp
    130                 135                 140

Ala Thr Tyr Tyr Leu Phe Gln Ser Phe Gln Lys Glu Leu Pro Trp Ala
145                 150                 155                 160

His Cys Asn His Ser Trp Asn Thr Pro His Cys Met Glu Asp Thr Met
                165                 170                 175

Arg Lys Asn Lys Ser Val Trp Ile Thr Ile Ser Ser Thr Asn Phe Thr
            180                 185                 190

Ser Pro Val Ile Glu Phe Trp Glu Arg Asn Val Leu Ser Leu Ser Pro
        195                 200                 205

Gly Ile Asp His Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Ala
            260                 265                 270

Gly Ile Lys Phe Tyr Leu Tyr Pro Asp Ile Thr Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
    370                 375                 380

Thr Phe Trp Ser Ile Leu Phe Phe Ile Met Leu Leu Leu Gly Leu
385                 390                 395                 400

Asp Ser Gln Phe Val Glu Val Glu Gly Gln Ile Thr Ser Leu Val Asp
                405                 410                 415
```

```
Leu Tyr Pro Ser Phe Leu Arg Lys Gly Tyr Arg Arg Glu Ile Phe Ile
            420             425             430

Ala Phe Val Cys Ser Ile Ser Tyr Leu Leu Gly Leu Thr Met Val Thr
            435             440             445

Glu Gly Gly Met Tyr Val Phe Gln Leu Phe Asp Tyr Tyr Ala Ala Ser
    450             455             460

Gly Val Cys Leu Leu Trp Val Ala Phe Phe Glu Cys Phe Val Ile Ala
465             470             475             480

Trp Ile Tyr Gly Gly Asp Asn Leu Tyr Asp Gly Ile Glu Asp Met Ile
            485             490             495

Gly Tyr Arg Pro Gly Pro Trp Met Lys Tyr Ser Trp Ala Val Ile Thr
            500             505             510

Pro Val Leu Cys Val Gly Cys Phe Ile Phe Ser Leu Val Lys Tyr Val
            515             520             525

Pro Leu Thr Tyr Asn Lys Thr Tyr Val Tyr Pro Asn Trp Ala Ile Gly
            530             535             540

Leu Gly Trp Ser Leu Ala Leu Ser Ser Met Leu Cys Val Pro Leu Val
545             550             555             560

Ile Val Ile Arg Leu Cys Gln Thr Glu Gly Pro Phe Leu Val Arg Val
            565             570             575

Lys Tyr Leu Leu Thr Pro Arg Glu Pro Asn Arg Trp Ala Val Glu Arg
            580             585             590

Glu Gly Ala Thr Pro Tyr Asn Ser Arg Thr Val Met Asn Gly Ala Leu
            595             600             605

Val Lys Pro Thr His Ile Ile Val Glu Thr Met Met
            610             615             620
```

METHOD OF PRODUCING HETEROGENEOUS PROTEIN

CROSS-REFERENCE TO RELATED APPLICATIONS

This application is a National Stage application of PCT/JP2008/064095, filed Aug. 6, 2008, which claims priority from Japanese application JP 2007-205158, filed Aug. 7, 2007.

1. Technical Field

The present invention relates to a method of producing a heterogenous protein, more specifically, a method of producing a polypeptide using a cell which strongly expresses alanine aminotransferase.

2. Background Art

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

Alanine is one of the proteinogenic amino acids, and is a non-essential amino acid. In a living body, it is biosynthesized by transfer of an amino group from glutamate to pyruvate, and is degraded by a reverse reaction.

As an alanine degrading enzyme, alanine aminotransferase (EC 2.6.1.2.) (Non-patent document 1) has been known. This enzyme transfers an amino group from alanine to 2-oxoglutarate to synthesize glutamate. Alanine aminotransferase is also called glutamic-pyruvic transaminase, which is abbreviated as GPT (Non-patent document 2). GPT and GOP (aspartate aminotransferase) are enzymes found in the liver. Since GPT and GOP are released into the blood when hepatic cells are destroyed, the liver is diagnosed to have some kind of disorder when abnormally high levels of GPT and GOT are observed.

As shown above, alanine aminotransferase is used as a marker of hepatic function. However, it has not been known how host cells such as CHO cells behave if alanine aminotransferase is strongly expressed in them.

[Non-Patent Document 1]
Sanjay B. J., et. al., Hepatology (2004) 39(5), 1297-1302
[Non-Patent Document 2]
Melanie M. S., et. al., Genomics (1997) 40, 247-252

DISCLOSURE OF THE INVENTION

Problem for Solution by the Invention

It is an object of the present invention to provide a method which is capable of producing a natural or recombinant protein in high yield.

Means to Solve the Problem

As a result of extensive and intensive researches toward the solution of the above problem, the present inventors have found that it is possible to increase the yield of a desired polypeptide by using a cell that strongly expresses alanine aminotransferase (hereinafter sometimes referred to as "ALT"). Thus, the present invention has been achieved. Moreover, the desired polypeptide could be produced in an even greater amount by using cells capable of co-expressing ALT and a taurine transporter. Since alanine is produced in large amount over time in cell culture, alanine accumulated in cells is secreted in the medium. If the reaction of biosynthesizing pyruvate and glutamate from alanine can be promoted by strongly expressing ALT, the products are utilized in metabolism during a TCA cycle and glucose production by glycogenesis. This will improve cell culture behavior, and thus high-yield production of the desired polypeptide is anticipated.

The present invention may be summarized as follows.

(1) A method of producing a polypeptide, comprising culturing a cell which strongly expresses alanine aminotransferase and has a transferred DNA encoding a desired polypeptide and thereby allowing the cell to produce said polypeptide.

(2) The method of (1) above, wherein the cell which strongly expresses alanine aminotransferase is a cell into which a DNA encoding the alanine aminotransferase has been transferred.

(3) The production method of (1) or (2) above, wherein the cells that strongly express alanine aminotransferase further express a taurine transporter strongly.

(4) The production method of (3) above, wherein the cells that strongly express a taurine transporter are cells into which DNA encoding a taurine transporter has been transferred.

(5) The method of (2) or (4) above, wherein the cell is Chinese hamster ovary cells.

(6) The method of any one of (1) to (5) above, wherein the desired polypeptide is an antibody.

(7) The method of any one of (2) to (6) above, wherein the DNA encoding the alanine aminotransferase is any one of the following (a) to (e):

(a) a DNA encoding a polypeptide having the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60;

(b) a DNA encoding a polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity;

(c) a DNA encoding a polypeptide having 70% or more amino acid sequence homology with the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 and yet having alanine aminotransferase activity;

(d) a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59;

(e) a DNA which hybridizes to a DNA complementary to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and yet encodes a polypeptide having alanine aminotransferase activity.

(8) A method of preparing a pharmaceutical containing a polypeptide prepared by the method of any one of (1) to (7) above.

(9) A cell which has a transferred DNA encoding alanine aminotransferase and a transferred DNA encoding a desired polypeptide.

(10) The cell according to (9) above, which further has a transferred DNA encoding a taurine transporter.

(11) A cell which has a transferred DNA encoding alanine aminotransferase and a transferred DNA encoding a taurine transporter.

(12) A method of producing a polypeptide, comprising culturing in an α-ketoglutarate-containing medium a cell which strongly expresses alanine aminotransferase and has a transferred DNA encoding a desired polypeptide and thereby allowing the cell to produce said polypeptide.

EFFECT OF THE INVENTION

According to the present invention, it has become possible to increase the yield of a desired polypeptide.

The present specification encompasses the contents disclosed in the specification and/or the drawings of Japanese Patent Application No. 2007-205158 based on which the present patent application claims priority.

BRIEF DESCRIPTION OF THE DRAWINGS

FIG. 8 shows the nucleotide sequence of a newly cloned, CHO cell-derived hamster taurine transporter gene and the amino acid sequence deduced therefrom.

BEST MODE FOR CARRYING OUT THE INVENTION

Figure 1:
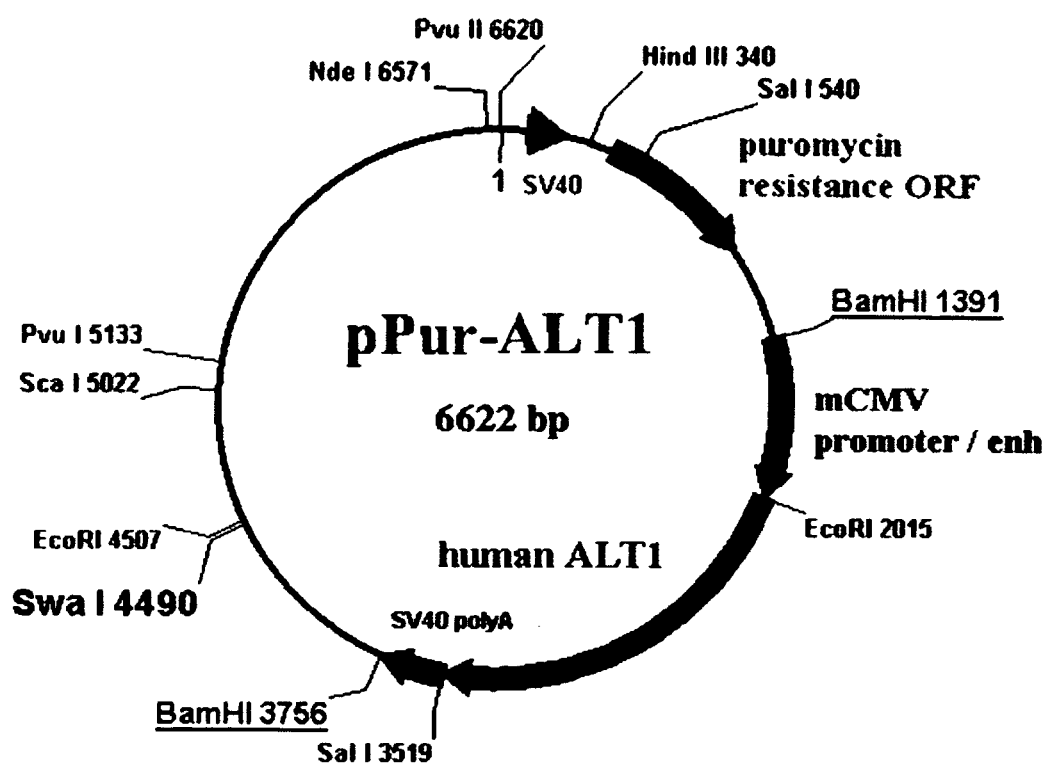
FIG. 1 shows a plasmid for Puromycin selection which was used for expressing human ALT1 (496 amino acids).

Hereinbelow, embodiments of the present invention will be described in more detail.

The present invention provides a method of producing a polypeptide, comprising culturing a cell which strongly expresses ALT and has a transferred DNA encoding a desired polypeptide and thereby allowing the cell to produce the polypeptide.

In the method of the present invention, the cell may be either a natural cell capable of producing the desired polypeptide or a transformed cell into which a DNA encoding the desired polypeptide has been transferred. Preferably, a transformed cell into which a DNA encoding the desired polypeptide has been transferred is used.

In the method of the present invention, the desired polypeptide is not particularly limited. The polypeptide may be any polypeptide such as an antibody (e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

By using strongly ALT expressing cells, the amount of a polypeptide produced by cells can be increased.

ALT is fundamentally known as an enzyme that produces glutamate by transferring an amino group from alanine to 2-oxoglutarate. The present inventors considered that if the reaction of biosynthesizing pyruvate and glutamate from alanine could be promoted by strongly expressing ALT in host cells such as CHO cells, the products might be utilized in metabolism during a TCA cycle and glucose production by glycogenesis, and this might improve cell culture behavior, leading to high-yield production of the desired polypeptide.

The strongly ALT expressing cells are not particularly limited as long as they are capable of ALT expression at higher levels than natural cells. Natural cells include, but are not particularly limited to, cells that are used as hosts in the production of recombinant proteins and may be exemplified by CHO cells.

A cell which strongly expresses ALT is not particularly limited as long as the cell has an increased expression level of ALT compared to a corresponding natural cell. The natural cell is not particularly limited. A cell which is used as a host in the production of a recombinant protein (e.g., CHO cells) may be used.

As a cell which strongly expresses ALT, a cell into which an ALT gene has been artificially transferred may be given. A cell into which an ALT gene has been artificially transferred can be prepared by methods known to those skilled in the art. For example, such a cell may be prepared by incorporating an ALT gene into a vector and transforming the vector into a cell. Furthermore, the concept of "cells into which an ALT gene has been artificially transferred" encompasses herein cells in which an endogenous ALT gene has been activated by gene activation technology (see, for example, International Publication WO94/12650) so that ALT is strongly expressed.

As ALT to be strongly expressed in a cell, ALT derived from any organism may be used. Specifically, ALTs derived from human, mouse, rat, dog, African clawed frog, fruit fly, nematode, Japanese rice, *Cyanidioschyzon merolae, Saccharomyces cerevisiae, Ashbya gossypii, Candida albicans, Schizosaccharomyces pombe, Aspergillus nidulans, Aspergillus fumigatus, Aspergillus oryzae, Cryptococcus neoformans, Dictyostelium discoideum, Trypanosoma brucei, Leishmania major, Entamoeba histolytica* and *Trypanosoma cruzi* are known and can be used. Preferably, ALT derived from human, a rodent or the same species as the host cell may be used. For example, when the cell which is allowed to strongly express ALT is Chinese hamster ovary cells (CHO cells), ALT is preferably derived from human or hamster. For ALT in humans, mice, and yeast, variants (ALT1 and ALT2) exist. ALT2 has 80% or greater homology to ALT1 at the amino acid level. ALT1 was forcedly expressed in the Examples described later.

Further, as an ALT gene to be strongly expressed in a cell, any one of the following DNAs (a) to (e) encoding ALT may be used.

(a) a DNA encoding a polypeptide having the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60;

(b) a DNA encoding a polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity;

(c) a DNA encoding a polypeptide having 70% or more amino acid sequence homology with the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 and yet having alanine aminotransferase activity;

(d) a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59;

(e) a DNA which hybridizes to a DNA complementary to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and yet encodes a polypeptide having alanine aminotransferase activity.

The cell which strongly expresses ALT may be any cell, for example, eukaryotic cell such as animal, plant and yeast cells, prokaryotic cell such as *E. coli* and *B. subtilis*, etc. Preferably, animal cells such as CHO and COS cells are used, CHO cells are particularly preferred. In order to prepare a desired polypeptide, cells suitable for transfer of a gene encoding the desired polypeptide such as CHO-dhfr- cells are preferred.

Preferably, the cell of the present invention which strongly expresses ALT further expresses a taurine transporter strongly in order to prepare a desired polypeptide. By transferring a gene encoding the desired polypeptide into the cell and culturing the resultant cell in a medium, the desired polypeptide can be produced in a greater amount.

When a desired polypeptide is produced using a cell into which an ALT gene has been artificially transferred, the order of the transfer of an ALT gene and the transfer of a gene encoding a desired polypeptide is not particularly limited. A gene encoding a desired polypeptide may be transferred after the transfer of an ALT gene. Alternatively, an ALT gene may be transferred after the transfer of a gene encoding a desired polypeptide. It is also possible to transfer an ALT gene and a gene encoding a desired polypeptide simultaneously.

An ALT gene and a gene encoding a desired polypeptide may be transferred simultaneously in a single vector. Alternatively, they may be transferred separately using a plurality of vectors.

By using a cell which strongly expresses ALT and a taurine transporter, an intracellular ammonia concentration can decline.

It is known that taurine transporter is a membrane protein having the osmoregulatory function of taking up amino acids (such as taurine and β-alanine) into cells.

A cell which strongly expresses a taurine transporter is not particularly limited as long as the cell has an increased expression level of a taurine transporter compared to a corresponding natural cell. The natural cell is not particularly limited. A cell which is used as a host in the production of a recombinant protein (e.g., CHO cells) may be used.

As a cell which strongly expresses a taurine transporter, a cell into which a taurine transporter gene has been artificially transferred may be given. A cell into which a taurine transporter gene has been artificially transferred can be prepared by methods known to those skilled in the art. For example, such a cell may be prepared by incorporating a taurine transporter gene into a vector and transforming the vector into a cell.

As a taurine transporter to be strongly expressed in a cell, a taurine transporter derived from any organism may be used. Specifically, a taurine transporter derived from human or a rodent (such as mouse, rat or hamster) may be used. Preferably, a taurine transporter derived from human, a rodent or the same species as the host cell may be used. For example, when the cell which is allowed to strongly express a taurine transporter is Chinese hamster ovary cells (CHO cells), the taurine transporter is preferably derived from human or hamster.

Further, as a taurine transporter gene to be strongly expressed in a cell, any one of the following DNAs ($a_1$) to ($e_1$) encoding a taurine transporter may be used.
($a_1$) a DNA encoding a polypeptide having the amino acid sequence as shown in SEQ ID NO: 62, 64, 66 or 68;
($b_1$) a DNA encoding a polypeptide which has an amino acid sequence derived from the amino acid sequence as shown in SEQ ID NO: 62, 64, 66 or 68 by substitution, deletion, addition and/or insertion of one or more amino acid residues and yet has taurine transporter activity;
($c_1$) a DNA encoding a polypeptide having 70% or more amino acid sequence homology with the amino acid sequence as shown in SEQ ID NO: 62, 64, 66 or 68 and yet having taurine transporter activity;
($d_1$) a DNA having the nucleotide sequence as shown in SEQ ID NO: 61, 63, 65 or 67;
($e_1$) a DNA which hybridizes to a DNA complementary to a DNA having the nucleotide sequence as shown in SEQ ID NO: 61, 63, 65 or 67 under stringent conditions and yet encodes a polypeptide having taurine transporter activity.

Production of a desired polypeptide may be performed by transferring a gene encoding the desired polypeptide into a cell which strongly expresses a taurine transporter gene and an ALT gene and culturing the resultant cell in a medium. Furthermore, a desired polypeptide can be prepared by using a cell in which an endogenous gene has been activated by gene activation technology (see, for example, International Publication WO94/12650) so that a desired polypeptide has been produced.

When a desired polypeptide is produced using a cell into which a taurine transporter gene and an ALT gene have been artificially transferred, the order of the transfer of a taurine transporter gene, the transfer of an ALT gene and the transfer of a gene encoding a desired polypeptide is not particularly limited. A gene encoding a desired polypeptide may be transferred after the transfer of a taurine transporter gene and an ALT gene. Alternatively, a taurine transporter gene and an ALT gene may be transferred after the transfer of a gene encoding a desired polypeptide. It is also possible to transfer a taurine transporter gene, an ALT gene and a gene encoding a desired polypeptide simultaneously.

A taurine transporter gene, an ALT gene and a gene encoding a desired polypeptide may be transferred simultaneously in a single vector. Alternatively, they may be transferred separately using a plurality of vectors.

For culturing the cell which strongly expresses ALT (and which may strongly express a taurine transporter), media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L, trace metal elements 0.00001-200 mg/L, surfactants 0-5000 mg/L, growth cofactors 0.05-10000 μg/L and nucleosides 0.001-50 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogenphosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

Further, α-ketoglutarate, serving as a substrate for ALT, can be added to the medium. The yield of the desired polypeptide (for example, an antibody) can be increased by addition of α-ketoglutarate. In this case, the amount of α-ketoglutarate to be added is normally in the range of 0.01 to 1000 mM, preferably 0.1 to 100 mM, and more preferably 1 to 10 mM.

The pH of the medium varies depending on the cell to be cultured. Generally, pH 6.8-7.6 is appropriate. In many cases, pH 7.0-7.4 is appropriate.

It is also possible to use a commercial medium for animal cell culture, e.g., D-MEM (Dulbecco's Modified Eagle Medium), D-MEM/F-12 1:1 Mixture (Dulbecco's Modified Eagle Medium Nutrient Mixture F-12), RPMI1640, CHO-S-SFMII (Invitrogen), CHO-SF (Sigma-Aldrich), EX-CELL 301 (JRH Biosciences), CD-CHO (Invitrogen), IS CHO-V (Irvine Scientific), PF-ACF-CHO (Sigma-Aldrich) or the like.

Alternatively, the medium may be a serum-free medium such as CD-CHO (Invitrogen).

When the cell which strongly expresses ALT (and which may strongly express a taurine transporter) is CHO cells, CHO cells may be cultured by methods known to those skilled in the art. For example, CHO cells may be cultured usually in an atmosphere with a $CO_2$ concentration in the gas phase of 0 to 40%, preferably 2 to 10%, at 30 to 39° C., preferably about 37° C.

Moreover, in the case where the desired polypeptide such as an antibody is produced by cell culture, cells become highly confluent at the late stage of the culture (approximately $1 \times 10^7$ cells/rill), and the effect of waste products such as lactate becomes extremely high. If the desired polypeptide is produced by strongly ALT expressing cells, a high survival ratio is maintained even at the late stage of the culture, and an improvement in the yield of the desired polypeptide can also be anticipated.

An appropriate culture period for producing a desired polypeptide using the cell which strongly expresses ALT is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the cell which strongly expresses ALT (and which may strongly express a taurine transporter) is cultured, taurine may be added to the medium in order to promote taurine uptake into cells. The concentration of taurine to be added to the medium is not specifically limited, but is normally in the range of 0 g/L to 100 g/L, preferably 0 g/L to 20 g/L, and more preferably 0 g/L to 10 g/L.

When the polypeptide produced according to the method of the present invention has a biological activity useful as a pharmaceutical, it is possible to produce a pharmaceutical by mixing this polypeptide with pharmaceutically acceptable carriers or additives and formulating into a preparation.

Specific examples of pharmaceutically acceptable carriers and additives include water, organic solvents that are pharmaceutically acceptable, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethyl cellulose, xanthan gum, gum Arabic, casein, agar-agar, polyethylene glycol, diglycerin, glycerin, propylene glycol, petrolatum, paraffin, stearyl alcohol, stearic acid, human serum albumin (HSA), mannitol, sorbitol, lactose, and surfactants that are acceptable as pharmaceutical additives.

Actual additives may be selected from the above-mentioned additives singly or in combination according to the dosage form of the therapeutic of the present invention, but are not limited to those listed above. For example, when a polypeptide is used in an injectable formulation, the purified polypeptide may be dissolved in a solvent such as physiological saline, buffer or a glucose solution, and then an adsorption inhibitor such as Tween 80, Tween 20, gelatin or human serum albumin may be added to the solution. Alternatively, a freeze-dried agent may be used to prepare a dosage form which is dissolved and reconstituted prior to use. Examples of the excipient useful for freeze-drying include sugar alcohols and saccharides such as mannitol and glucose.

Effective doses of the polypeptide may be appropriately selected depending on the type of the polypeptide, the type of the disease to be treated or prevented, the age of the patient, the severity of the disease, etc. For example, when the polypeptide is anti-glypican antibody, the effective dose of anti-glypican antibody is selected within a range of 0.001 mg to 1000 mg per kg of body weight per administration. Alternatively, a dose of 0.01-100000 mg/body may be selected per patient. However, effective dose is not limited to these ranges.

The polypeptide may be administered either orally or parenterally, but parenteral administration is preferred. Specifically, injection (e.g., systemic or local administration by intravenous injection, intramuscular injection, intraperitoneal injection, subcutaneous injection, etc.), transnasal administration, transpulmonary administration, transdermal administration and the like may be enumerated.

In the present invention, as a gene encoding ALT, a DNA encoding a polypeptide having the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 may be used. Alternatively, a DNA encoding a polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity may be used.

The polypeptide which has an amino acid sequence derived from the amino acid sequence as shown in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 by substitution, deletion, addition and/or insertion of one or more amino acid residues and yet has alanine aminotransferase activity is functionally equivalent to ALT derived from human, mouse, rat, dog, African clawed frog, fruit fly, nematode, Japanese rice, Cyanidioschyzon merolae, Saccharomyces cerevisiae, Ashbya gossypii, Candida albicans, Schizosaccharomyces pombe, Aspergillus nidulans, Aspergillus fumigatus, Aspergillus oryzae, Cryptococcus neoformans, Dictyostelium discoideum, Trypanosoma brucei, Leishmania major, Entamoeba histolytica or Trypanosoma cruzi (hereinafter sometimes referred to as "ALT derived from human or the like"). Such a polypeptide encompasses, for example, mutants of ALT derived from human or the like. In Example described below, a mutant in which four out of 496 amino acids were replaced (R53S, Q72R, F286S and M332K) was used.

As methods well-known to those skilled in the art for preparing polypeptides functionally equivalent to a specific polypeptide, methods of introducing mutations into polypeptides may be given. For example, those skilled in the art could prepare polypeptides functionally equivalent to ALT derived from human or the like by appropriately introducing mutations into amino acids of ALT derived from human or the like by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985)

Proc Natl Acad Sci USA. 82, 488-492; Kunkel (1988) Methods Enzymol. 85, 2763-2766). Mutations in amino acids may also occur in nature.

Specific examples of polypeptides functionally equivalent to the ALT derived from human or the like include, but are not limited to, a polypeptide having an amino acid sequence derived from the amino acid sequence (e.g., SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60) of the ALT derived from human or the like by deletion of one or more amino acids, preferably 1-30 amino acids, more preferably 1-10 amino acids; a polypeptide having an amino acid sequence derived from the amino acid sequence of the ALT derived from human or the like by addition of one or more amino acids, preferably 1-30 amino acids, more preferably 1-10 amino acids; and a polypeptide having an amino acid sequence derived from the amino acid sequence of the ALT derived from human or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, H, K, S and T), amino acids with an aliphatic side chain (G A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to the ALT derived from human or the like, a fusion polypeptide comprising the ALT derived from human or the like may be given. Such a fusion polypeptide is composed of the ALT derived from human or the like and other polypeptide fused thereto. Such a fusion polypeptide may be prepared by linking a gene encoding the ALT derived from human or the like in frame with a gene encoding the other polypeptide, transferring the resultant DNA into an expression vector and expressing the DNA in a host cell. Techniques known to those skilled in the art may be used. There is no limitation on the polypeptide to be fused to the ALT derived from human or the like.

Examples of polypeptides to be fused to the ALT derived from human or the like include, but are not limited to, FLAG (Hopp, T. P et al., BioTechnology (1988) 6, 1204-1210), 6×His comprising six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the ALT derived from human or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence (e.g., SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59) of the ALT derived from human or the like based on that DNA sequence or a part thereof, and isolate polypeptides functionally equivalent to the ALT derived from human or the like from that DNA.

Hybridization conditions for isolating a DNA encoding a polypeptide functionally equivalent to the ALT derived from human or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the ALT derived from human or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the ALT derived from human or the like, DNA encoding the polypeptide can be used in the present invention. For example, when the polypeptide of the present invention is expressed in a prokaryote (e.g., *Escherichia coli*), a methionine reside is added to the N-terminus of the initial amino acid sequence of the polypeptide. When the polypeptide is expressed in a eukaryote (e.g., a mammalian cell), the N-terminal signal sequence is removed. These polypeptides can be used in the present invention.

The polypeptide may be prepared as a recombinant polypeptide or a natural polypeptide by methods known to those skilled in the art. A recombinant polypeptide may be prepared by incorporating a DNA encoding the polypeptide in an appropriate expression vector, introducing the vector into an appropriate host cell, collecting the resultant transformant, extracting a crude polypeptide, and then purifying the polypeptide by chromatography (such as ion exchange, reversed phase or gel filtration chromatography, or affinity chromatography in which an antibody to the polypeptide prepared by the method of the present invention is fixed in a column) or a combination of these chromatographic techniques.

When the polypeptide is expressed in a host cell (e.g., animal cell or *E coli*) as a fusion polypeptide with glutathione-S-transferase polypeptide or as a recombinant polypeptide with histidine residues added thereto, the expressed polypeptide may be purified with a glutathione column or a nickel column.

After purification of a fusion polypeptide, regions other than the polypeptide of interest may be cut off by thrombin or factor Xa and removed from the fusion polypeptide.

When the polypeptide is a natural polypeptide, the polypeptide may be isolated by purification methods known to those skilled in the art. For example, an extract from tissues or cells expressing the polypeptide functionally equivalent to the ALT derived from human or the like may be applied to an affinity column to which an antibody to the ALT derived from human or the like is bound. The antibody may be either a polyclonal antibody or a monoclonal antibody.

In the present invention, as DNA encoding ALT, a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 may be used. Alternatively, a DNA which hybridizes to a DNA complementary to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and yet encodes a polypeptide having alanine aminotransferase activity, may be used.

The DNA encoding ALT can be used in the in vivo or in vitro production of a desired polypeptide as described above. Further, the DNA encoding ALT may be used in the creation of a cell which strongly expresses ALT. The DNA encoding ALT may take any form as long as it is capable of encoding ALT. That is, the DNA may be, for example, a cDNA synthesized from mRNA, a genomic DNA or a chemically synthesized DNA. It should be noted that, as long as the DNA is capable of encoding ALT, the DNA may have any nucleotide sequence based on the degeneracy of genetic codes.

The DNA encoding ALT may be prepared by methods known to those skilled in the art. For example, the DNA may be prepared by preparing a cDNA library from a cell expressing ALT and performing hybridization using a part of the DNA sequence of ALT (e.g., SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding ALT by preparing RNA from a cell expressing ALT, synthesizing oligo DNA molecules based on the DNA sequence of ALT (e.g., SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59), and performing PCR using the oligo DNA molecules as primers to thereby amplify a cDNA encoding ALT.

Further, by determining the nucleotide sequence of the resultant cDNA, it is possible to determine the translation region encoding ALT and to obtain the amino acid sequence of ALT. Further, by screening a genomic library using the resultant cDNA as a probe, it is possible to isolate a genomic DNA.

Specifically, the following procedures may be used. First, mRNA is isolated from cells, tissues or the like expressing ALT. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., *E. coli*), followed by selection of resultant colonies to thereby obtain a desired recombinant vector. The nucleotide sequence of the DNA of interest may be confirmed by a known method such as the dideoxynucleotide chain termination method.

Further, a nucleotide sequence of higher expression efficiency can be designed for the DNA encoding ALT by considering the frequency of codon usage in the host to be used for expression (Grantham, R. et al., Nucleic Acids Research $(1981)_9$, p. 43-74). Further, the DNA encoding ALT can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding ALT also includes a DNA which hybridizes to a DNA having the nucleotide sequence as shown in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57 or 59 under stringent conditions and encodes a polypeptide functionally equivalent to ALT.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the ALT derived from human or the like. The DNA encoding ALT also includes a DNA which encodes a polypeptide functionally equivalent to the ALT derived from human or the like and has high identity with a DNA encoding the ALT derived from human or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (http://www.ncbi.nlm.nih.gov.).

The DNA encoding ALT may be inserted into a vector.

When the host cell to be used is *E. coli*, it is preferable that the vector has a replication origin ("ori") so that the vector is largely amplified in *E. coli* (e.g., JM109, DH5α, HB101 and XL1-Blue) and prepared in large quantity, and also genes for selecting transformed *E. coli* (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in *E. coli* is intended, the expression vector preferably has the above-described features so that the vector is amplified in *E. coli*, and it also preferably has a promoter which allows efficient expression in *E. coli* such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5X-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing a desired polypeptide include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdexLcw), retrovirus-derived expression vectors (e.g., pZIpneo), yeast-derived expression vectors (e.g., *Pichia* Expression Kit from Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The host cell into which the DNA encoding ALT (which may be incorporated in a vector) is transferred is not particularly limited. For example, *E. coli* or various animal cells may be used. If DNA encoding a desired polypeptide is transferred into a host cell into which DNA encoding ALT is transferred, this host cell can express ALT strongly, which leads to an increased production of the desired polypeptide. DNA encoding a taurine transporter (which may be incorporated into a vector) may be further transferred into the host cell into which DNA encoding ALT is transferred. By transferring DNA encoding a desired polypeptide and DNA encoding a taurine transporter into a host cell into which DNA encoding ALT is transferred, the yield of the desired polypeptide can be increased. For the production of the polypeptide, there are in vivo and in vitro production systems. Examples of in vitro production systems include systems using eukaryotes and systems using prokaryotes.

In the present invention, as DNA encoding a taurine transporter, a DNA encoding a polypeptide having the amino acid sequence as shown in SEQ ID NO: 62, 64, 66 or 68 may be used. Alternatively, a DNA encoding a polypeptide which has an amino acid sequence derived from the amino acid sequence as shown in SEQ ID NO: 62, 64, 66 or 68 by substitution, deletion, addition and/or insertion of one or more amino acid residues and yet has taurine transporter activity may be used.

The polypeptide which has an amino acid sequence derived from the amino acid sequence as shown in SEQ ID NO: 62, 64, 66 or 68 by substitution, deletion, addition and/or insertion of one or more amino acid residues and yet has taurine transporter activity is functionally equivalent to a hamster, rat, mouse or human taurine transporter (hereinafter sometimes referred to as "taurine transporter derived from hamster or the like"). Such a polypeptide encompasses, for example, mutants of the taurine transporter derived from hamster or the like.

As methods well-known to those skilled in the art for preparing polypeptides functionally equivalent to a specific polypeptide, methods of introducing mutations into polypeptides may be given. For example, those skilled in the art could prepare polypeptides functionally equivalent to hamster taurine transporter by appropriately introducing mutations into amino acids of hamster taurine transporter by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, TA (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to the taurine transporter derived from hamster or the like include, but are not limited to, a polypeptide having an amino acid sequence derived from the amino acid sequence of the taurine transporter derived from hamster or the like by deletion of one or more amino acids, preferably 2-30 amino acids, more preferably 2-10 amino acids; a polypeptide having an amino acid sequence derived from the amino acid sequence of the taurine transporter derived from hamster or the like by addition of one or more amino acids, preferably 2-30 amino acids, more preferably 2-10 amino acids; and a polypeptide having an amino acid sequence derived from the amino acid sequence of the taurine transporter derived from hamster or the like by substitution of one or more amino acids, preferably 2-30 amino acids, more preferably 2-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, H, K, S and T), amino acids with an aliphatic side chain (G; A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

As one example of the polypeptide in which one or more amino acid residues are added to the taurine transporter derived from hamster or the like, a fusion polypeptide comprising the taurine transporter derived from hamster or the like may be given. Such a fusion polypeptide is composed of the taurine transporter derived from hamster or the like and other polypeptide fused thereto. Such a fusion polypeptide is included in the present invention. Such a fusion polypeptide may be prepared by linking a gene encoding the taurine transporter derived from hamster or the like in frame with a gene encoding the other polypeptide, transferring the resultant DNA into an expression vector and expressing the DNA in a host cell. Techniques known to those skilled in the art may be used. There is no limitation on the polypeptide to be fused to the taurine transporter derived from hamster or the like.

Examples of polypeptides to be fused to the taurine transporter derived from hamster or the like include, but are not limited to, FLAG (Hopp, T. P. et al., BioTechnology (1988) 6, 1204-1210), 6×His comprising six histidine (His) residues, 10×His, influenza hemagglutinin (HA), human c-myc fragment, VSV-GP fragment, p18HIV fragment, T7-tag, HSV-tag, E-tag, SV40T antigen fragment, lck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the taurine transporter derived from hamster or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence of the taurine transporter derived from hamster or the like based on that DNA sequence or a part thereof, and isolate polypeptides functionally equivalent to the taurine transporter derived from hamster or the like from that DNA.

Hybridization conditions for isolating a DNA encoding a polypeptide functionally equivalent to the taurine transporter derived from hamster or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the taurine transporter derived from hamster or the like in the amino acid sequence. The polypeptide also include those polypeptides which are functionally equivalent to the taurine transporter derived from hamster or the like and have high homology with the amino acid sequence of the taurine transporter derived from hamster or the like. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the taurine transporter derived from hamster or the like, a DNA encoding the polypeptide can be used in the present invention. For example, when the polypeptide is expressed in a prokaryote (e.g., *Escherichia coli*), a methionine reside is added to the N-terminus of the initial amino acid sequence of the polypeptide. When the polypeptide is expressed in a eukaryote (e.g., a mammalian cell), the N-terminal signal sequence is removed. DNAs encoding such polypeptides can be used in the present invention.

The polypeptide may be prepared as a recombinant polypeptide or a natural polypeptide by methods known to those skilled in the art. A recombinant polypeptide may be prepared by incorporating a DNA encoding the polypeptide in an appropriate expression vector, introducing the vector into an appropriate host cell, collecting the resultant transformant, extracting a crude polypeptide, and then purifying the polypeptide by chromatography (such as ion exchange, reversed phase or gel filtration chromatography, or affinity chromatography in which an antibody to the polypeptide is fixed in a column) or a combination of these chromatographic techniques.

When the polypeptide is expressed in a host cell (e.g., animal cell or *E coli*) as a fusion polypeptide with glutathione-S-transferase polypeptide or as a recombinant polypeptide with histidine residues added thereto, the expressed polypeptide may be purified with a glutathione column or a nickel column.

After purification of a fusion polypeptide, regions other than the polypeptide of interest may be cut off by thrombin or factor Xa and removed from the fusion polypeptide.

When the polypeptide is a natural polypeptide, the polypeptide may be isolated by purification methods known to those skilled in the art. For example, an extract from tissues or cells expressing the polypeptide may be applied to an affinity column to which an antibody to the taurine transporter derived from hamster or the like described later is bound. The antibody may be either a polyclonal antibody or a monoclonal antibody.

In the present invention, as DNA encoding a taurine transporter, a DNA having the nucleotide sequence as shown in SEQ ID NO: 61, 63, 65 or 67 may be used. Alternatively, a DNA which hybridizes to a DNA complementary to a DNA having the nucleotide sequence as shown in SEQ ID NO: 61, 63, 65 or 67 under stringent conditions and yet encodes a polypeptide having taurine transporter activity may be used.

The DNA encoding a taurine transporter can be used in the in vivo or in vitro production of a desired polypeptide as described above. Further, the DNA encoding a taurine transporter may be used in the creation of a cell which strongly expresses a taurine transporter. The DNA encoding a taurine transporter may take any form as long as it is capable of encoding a taurine transporter. That is, the DNA may be, for example, a cDNA synthesized from mRNA, a genomic DNA or a chemically synthesized DNA. It should be noted that, as long as the DNA is capable of encoding a taurine transporter, the DNA may have any nucleotide sequence based on the degeneracy of genetic codes.

The DNA encoding a taurine transporter may be prepared by methods known to those skilled in the art. For example, the DNA may be prepared by preparing a cDNA library from a cell expressing a taurine transporter and performing hybridization using a part of the DNA sequence encoding a taurine transporter (e.g., SEQ ID NO: 61, 63, 65 or 67) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding a taurine transporter by preparing RNA from a cell expressing the taurine transporter, synthesizing oligo DNA molecules based on the DNA sequence of the taurine transporter (e.g., SEQ ID NO: 61, 63, 65 or 67), and performing PCR using the oligo DNA molecules as primers to thereby amplify a cDNA encoding the taurine transporter.

Further, by determining the nucleotide sequence of the resultant cDNA, it is possible to determine the translation region encoding a taurine transporter and to obtain the amino acid sequence of the taurine transporter. Further, by screening a genomic library using the resultant cDNA as a probe, it is possible to isolate a genomic DNA.

Specifically, the following procedures may be used. First, mRNA is isolated from cells, tissues or the like expressing a taurine transporter. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., *E. coli*), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA encoding a taurine transporter by considering the frequency of codon usage in the host to be used for expression (Grantham, R. et al., Nucleic Acids Research (1981)$_9$, p. 43-74). Further, the DNA encoding a taurine transporter can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding a taurine transporter also includes a DNA which hybridizes to a DNA complementary to a DNA having the nucleotide sequence as shown in SEQ ID NO: 61, 63, 65 or 67 under stringent conditions and encodes a polypeptide functionally equivalent to a taurine transporter.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the taurine transporter derived from hamster, etc. The DNA also includes a DNA which encodes a polypeptide functionally equivalent to the taurine transporter derived from hamster, etc. and has high identity with a DNA encoding the taurine transporter derived from hamster, etc. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as expect value=100 and word size=12, for example. Specific procedures for these analysis methods are known (http://www.ncbi.nlm.nih.gov.).

The DNA encoding a taurine transporter may be inserted into a vector.

When the host cell to be used is *E. coli*, it is preferable that the vector has a replication origin ("ori") so that the vector is largely amplified in *E. coli* (e.g., JM109, DH5α, HB101 and XL1-Blue) and prepared in large quantity, and also genes for selecting transformed *E. coli* (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in *E. coli* is intended, the expression vector preferably has the above-described features so that the vector is amplified in *E. coli*, and it also preferably has a promoter which allows efficient expression in *E. coli* such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5X-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of *E. coli*, pelB signal sequence (Lei, S. P. et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than *E. coli* is used, vectors useful for producing a desired polypeptide include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovirus expression system from GIBCO BRL; pBacPAK8), plant-derived expression vectors (e.g., pMH1, pMH2), animal virus-derived expression vectors (e.g., pHSV, pMV, pAdexLcw), retrovirus-derived expression vectors (e.g., pZIpneo), yeast-derived expression vectors (e.g., *Pichia* Expression Kit from Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The present invention provides a cell which has a transferred DNA encoding ALT and a transferred DNA encoding a taurine transporter, both or either of which may be incorporated into a vector.

When eukaryotes are used, animal cells, plant cells, fungal cells, etc. may be used as the host. Specific examples of animal cells include mammalian cells, such as CHO cells (J. Exp. Med. (1995) 108, 945), COS cells, 3T3 cells, myeloma cells, BHK (baby hamster kidney) cells, HeLa cells and Vero cells; amphibian cells, such as oocytes of *Xenopus laevis* (Valle, et al., Nature (1981) 291, 358-340); or insect cells, such as sf9, sf21 and Tn5 cells. Amoung CHO cells, dhfr-CHO lacking DHFR gene (Proc. Natl. Acad. Sci. USA (1980) 77, 4216-4420) and CHO K-1 (Proc. Natl. Acad. Sci. USA (1968) 60, 1275) are used with particular advantage. When high expression is intended in an animal cell, CHO cells are especially preferred. Introduction of the DNA which may be incorporated into a vector into the host cell may be performed by such methods as the calcium phosphate method, the DEAE dextran method, a method using a cationic ribosome DOTAP (Boehringer-Mannheim), electroporation, lipofection, etc.

As plant cells for polypeptide production, a *Nicotiana tabacum*-derived cell is known as a polypeptide production system and this may be subjected to callus culture. As fungal cells for polypeptide production, specific examples include yeast belonging to the genus *Saccharomyces*, e.g., *Saccharomyces cerevisiae*, and filamentous fungi belonging to the genus *Aspergillus*, e.g., *Aspergillus niger*.

When prokaryotes are used, production systems using bacterial cells are known. Specific examples of such bacterial cells include *E. coli* (such as JM109, DH5α, HB101) and *Bacillus subtilis*.

The polypeptide encoded by a gene of interest may be obtained by transforming these cells with the gene of interest and culturing the transformed cells in vitro. The culture may be performed by known methods. For example, as a culture broth for animal cells, a medium such as DMEM, MEM, RPMI1640 or IMDM may be used. A serum supplement such as fetal calf serum (FCS) may be used jointly. Alternatively, serum-free culture may be performed. The pH during culture is preferably about 6 to 8. The culture is usually performed at about 30-40° C. for about 15-200 hours. If necessary, replacement of the medium, aeration and agitation are carried out.

On the other hand, in vivo production systems include those using animals or plants. A gene of interest is transferred into these animals or plants to produce the polypeptide in the animal bodies or plant bodies. Then, the polypeptide is collected. The term "host" as used herein includes such animals or plants.

When animals are used, available production systems include those using mammals or insects. Goat, pig, sheep, mouse and cattle may be used as mammals (Vicki Glaser, SPECTRUM Biotechnology Applications, 1993). When mammals are used, transgenic animals may be used.

First, a gene of interest is fused to a gene encoding a polypeptide produced inherently in milk (such as goat (3-casein) to thereby prepare a fusion gene. A DNA fragment containing this fusion gene is injected into a goat embryo, which is then implanted in the uterus of a female goat. The polypeptide of interest can be obtained from the milk produced by transgenic goats born from the goat which accepted the embryo or the offspring of the transgenic goats. In order to increase the yield of milk containing the polypeptide produced by the transgenic goats, hormones may be appropriately administered to the transgenic goats (Ebert, K. M. et al., Bio/Technology (1994) 12, 699-702).

Examples of insects which may be used include silkworm. In this case, silkworm is infected with baculovirus carrying a transferred gene encoding the polypeptide of interest. The polypeptide of interest can be obtained from the body fluid of the silkworm (Susumu, M. et al., Nature (1985) 315, 592-594).

Furthermore, when plants are used, tobacco can typically be used. When tobacco is used, a gene encoding the polypeptide of interest is inserted into a plant expression vector (e.g., pMON 530), which is then transferred into a bacterium such as *Agrobacterium tumefaciens*. A tobacco plant (e.g., *Nicotiana tabacum*) is infected with the resultant bacterium. The polypeptide of interest can be obtained from leaves of this plant (Julian, K.-C. Ma et al., Eur. J. Immunol. (1994) 24, 131-138).

The polypeptide thus obtained can be isolated from the inside of the host cell or from its outside (e.g., medium), and purified to a substantially pure and homogeneous polypeptide. Isolation and purification of polypeptides can be performed using conventional isolation and purification methods for polypeptides, and are not limited in any way. For example, polypeptides can be isolated and purified by appropriate selection and combination of various tools and techniques, such as chromatography columns, filters, ultrafiltration, salting-out, precipitation with solvent, extraction with solvent, distillation, immunoprecipitation, SDS-polyacrylamide gel electrophoresis, isoelectric focusing, dialysis, recrystallization, etc.

Examples of chromatography include affinity chromatography, ion exchange chromatography, hydrophobic chromatography, gel filtration, reverse-phase chromatography, adsorption chromatography, etc. (Strategies for Protein Purification and Characterization: A Laboratory Course Manual. Ed. Daniel R. Marshak et al., Cold Spring Harbor Laboratory Press, 1996). These chromatographic techniques can be carried out using liquid phase chromatography, for example, HPLC, FPLC, etc. The present invention also includes those polypeptides highly purified using these purification methods.

Before or after the purification, it is also possible to give optional modifications to the polypeptide or remove a partial peptide therefrom by reacting the polypeptide with an appropriate polypeptide modification enzyme. Examples of such enzyme include, but are not limited to, trypsin, chymotrypsin, lysyl endopeptidase, protein kinase and glucosidase.

In the present invention, the concept of "cells into which DNA has been transferred" encompasses not only cells into which exogenous DNA has been incorporated by genetic recombination technology; but also cells in which endogenous DNA has been activated by gene activation technology (see, for example, International Publication WO94/12650) so that expression of a protein corresponding to the endogenous DNA or transcription of the DNA has been initiated or increased.

EXAMPLES

Hereinbelow, the present invention will be described in more detail with reference to the following Examples. It should be noted that these Examples are provided only for illustrating the present invention and not for limiting the scope of the present invention.

Example 1

Cloning of Human Hepatic Cell Alanine Aminotransferase Gene

Using a commercial Human Liver QUICK-Clone cDNA (Clontech Laboratories, Inc.) as a template, alanine aminotransferase (ALT1) gene derived from a human liver was obtained by a PCR method. The gene thus cloned was sequenced and confirmed to encode ALT 1 based on its homology with published human ALT 1. The ALT 1 gene thus obtained had mutations at five sites in the sequence of 1488 bases (c157a, a215g, c765t, t857c, t995a) and coded for 496 amino acids including four different amino acids (R53S, Q72R, F286S, M332K), but this was used as a PCR clone of the human liver derived ALT1 for cell modulation.

Example 2

Increase in Antibody Yield by Transfer of Human Alanine Aminotransferase

Figure 2:
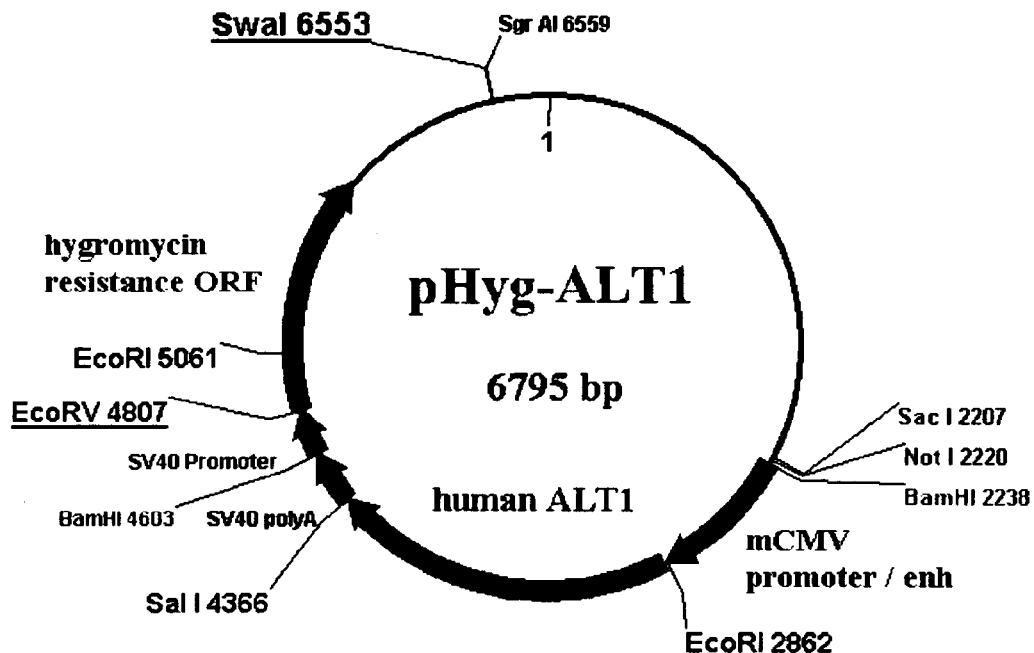
FIG. 2 shows a plasmid for Hygromycin selection which was used for expressing human ALT1 (496 amino acids).
Figure 3:
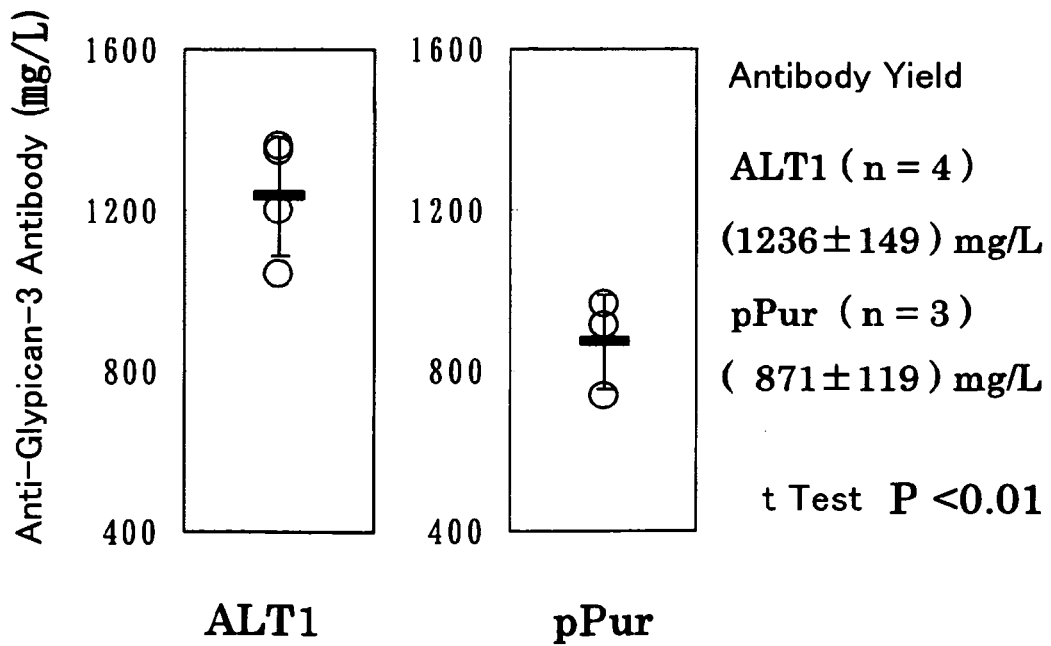
FIG. 3 shows anti-glypican-3 antibody yield plots on day 17 of 50 ml shaker flask fed-batch culture. The antibody yield in pPur-ALT1-transferred cell (n=4) was superior to that in pPur-transferred cell (n=3) (P<0.01).
C
Figure 4:
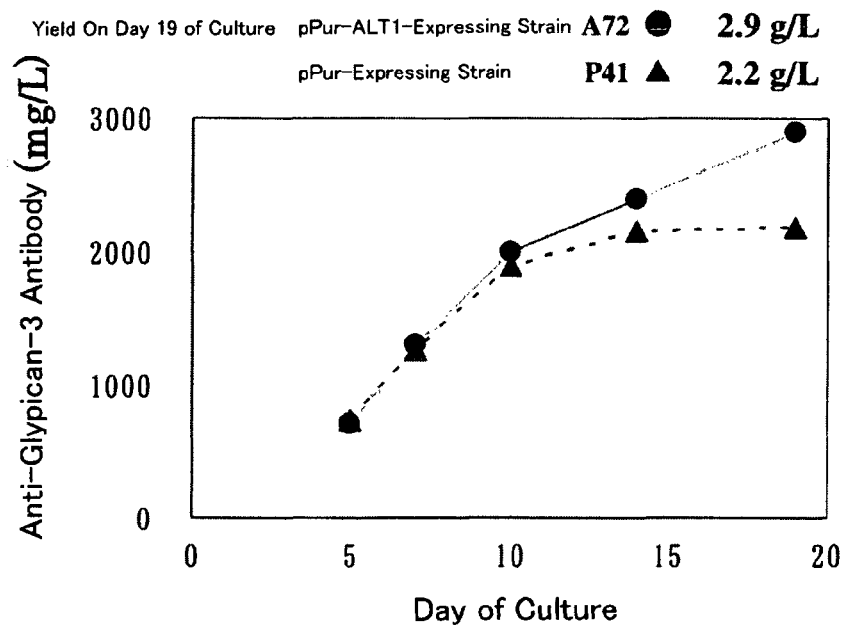
FIG. 4 is a graph showing the antibody yields of A72, which is an ALT1 expressing strain, and P41 as a control strain, in 1 L jar fed-batch culture. The anti-glypican-3 antibody yield of A72 was 2.9 g/L on day 19 of the culture, which was higher than that of P41.
Figure 5:
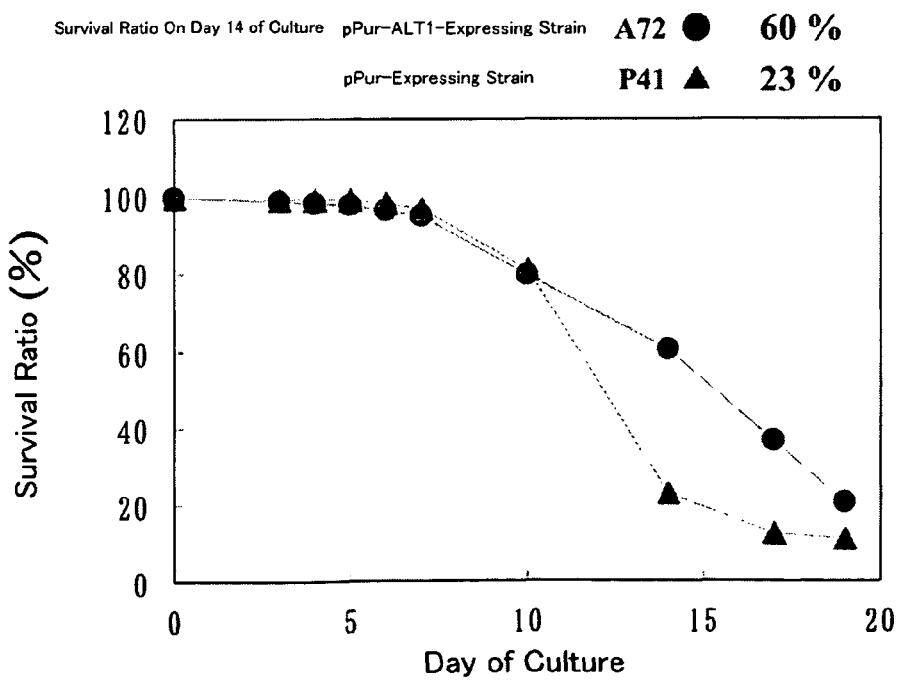
FIG. 5 is a graph showing the survival ratios of A72, which is an ALT1 expressing strain, and P41 as a control strain. The survival ratio of A72 at the late stage of the culture was higher than that of P41.

By adding a Kozak sequence to the human ALT1 obtained by cloning in Example 1 (which is hereinafter called ALT1), pPur-ALT1 (FIG. 1) and pHyg-ALT1 (FIG. 2), which were CMV promoter expression plasmids, were constructed. The pPur-ALT1 or pPur expression plasmids that did not contain the ALT1 gene were introduced into anti-glypican-3 antibody-producing CHO cells as parent strains (see International Publication WO 2006/006693) by electroporation, and cell strains that exhibited high proliferation in static culture in the presence of Puromycin (6 µg/ml) (pPur-ALT 1: seven strains, pPur: three strains) were selected. After expansion, a total RNA was prepared from the pPur-ALT 1 cell strains, and six strains expressing human ALT1 at high levels were selected by a TaqMan method. Further, a comparison was made for the antibody yield between pPur-transferred cells as a control (three strains) and four strains of human ALT I-transferred cells that proliferated at a level equivalent to that observed with the pPur-transferred cells during the shake culture. During fed-batch culture in a 50 ml shaker flask with an initial cell density of $2 \times 10^5$ cells/mL, the anti-glypican-3 antibody yield of pPur-ALT1-transferred cells (four strains) on day 17 at the late stage of the shaker culture was significantly higher than that of pPur-transferred cells (three strains) (t-test: p<0.01, FIG. 3). A72, a pPur-ALT1 expressing strain, and P41, a pPur expressing strain, were each found to have produced the largest amount of an antibody in the study using shaker fed-batch culture, and they were subjected to fed-batch culture in 1 L jars (an initial cell density of $10 \times 10^5$ cells/mL). As a result, the antibody yield of A72 was 2.9 g/L on day 19 of the culture, which was greater than the antibody yield of P41 (2.2 g/L) (FIG. 4). Since no increase was observed in the antibody yield of P41 on day 14 or subsequent days after the initiation of the culture, the high-yield production of an antibody by A72 was considered to be attributable to the survival ratio maintaining effect (FIG. 5). Further, pHyg/ALT-transferred cells (three strains), which were drug-selected in the presence of Hygromycin (200 μg/mL) by a method similar to the one described above, were subjected to fed-batch culture, together with the parent strain, in 15 ml tubes (an initial cell density of $1 \times 10^5$ cells/mL). As a result, the anti-glypican-3 antibody yield of the pHyg-ALT-transferred cells on day 10 at the late stage of the tube culture were 471 mg/L, 544 mg/L, and 588 mg/L, showing that the antibody yield of any one of them was greater than that of the parent strain (400 mg/L) (data not shown).

Figure 6:
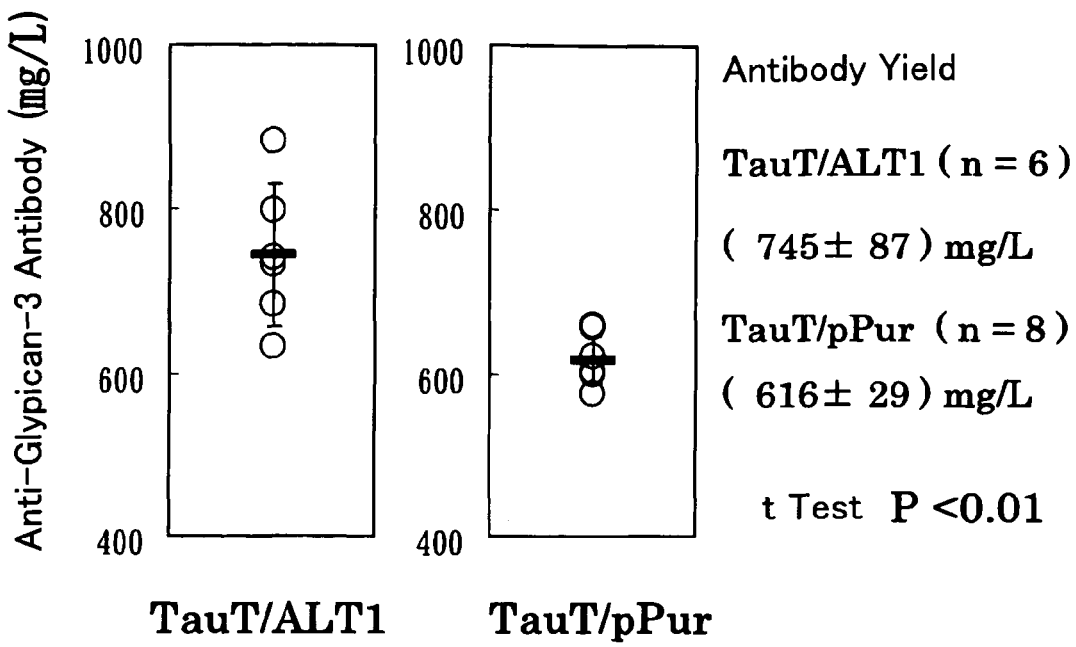
FIG. 6 shows anti-glypican-3 antibody yield plots on day 4 of 50 ml shaker flask fed-batch culture. The antibody yield in pHyg-TauT/pPur-ALT1-cotransferred cell (n=6) was superior to that in pHyg-TauT/pPur-cotransferred cell (n=8) (P<0.01).

Then, pPur-ALT1 or pPur was co-transferred into T10 which was a pHyg-TauT-transferred cell used as a parent strain (see Referential Example 2 described later). TauT/ALT1 co-expressing cells that exhibited high proliferation and expressed human ALT1 at high level (six strains) and TauT/pPur co-expressing cells that exhibited high proliferation (eight strains) were selected and subjected to fed-batch culture in 50 mL shaker flasks (an initial cell density of $10 \times 10^5$ cells/mL). The anti-glypican-3 antibody yield of TauT/ALT1 co-expressing cells, which were ALT expressing cells, on day 4 of the shaker culture was significantly higher than that of TauT/pPur cells (t-test: $p < 0.01$, FIG. 6).

Figure 7:
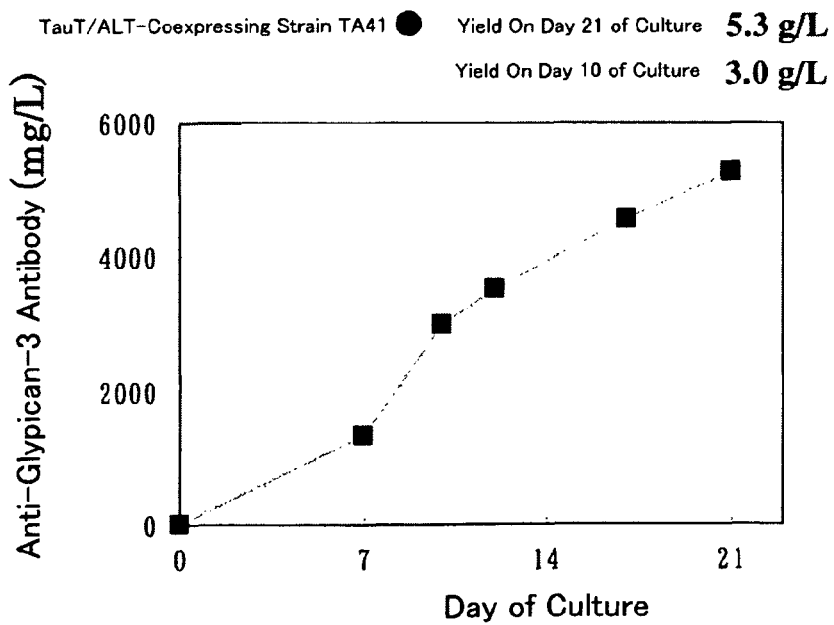
FIG. 7 is a graph showing the antibody yield of TA41, which is a TauT/ALT1 co-expressing strain, in 1 L jar fed-batch culture. The anti-glypican-3 antibody yield was 5.3 g/L on day 21 of the culture.

TA41, which was a TauT/ALT1 co-expressing strain that produced the largest amount of an antibody (881 mg/L/4 days) and expressed ALT1 mRNA at the highest level in the study using the shaker fed-batch culture, was subjected to fed-batch culture in a 1 L jar (an initial cell density of $10 \times 10^5$ cells/mL). The antibody yields were as high as 1.3 g/L on day 7 of the culture, 3.0 g/L on day 10 of the culture, 3.5 g/L on day 12 of the culture, 4.6 g/L on day 17 of the culture, and 5.3 g/L on day 21 of the culture (FIG. 7), which were clearly higher than the values for TP08 (656 mg/L/4 days), which was a control strain that produced the largest amount of an antibody among the TauT/pPur co-expressing strains (2.4 g/L on day 10 of the culture).

Figure 22:
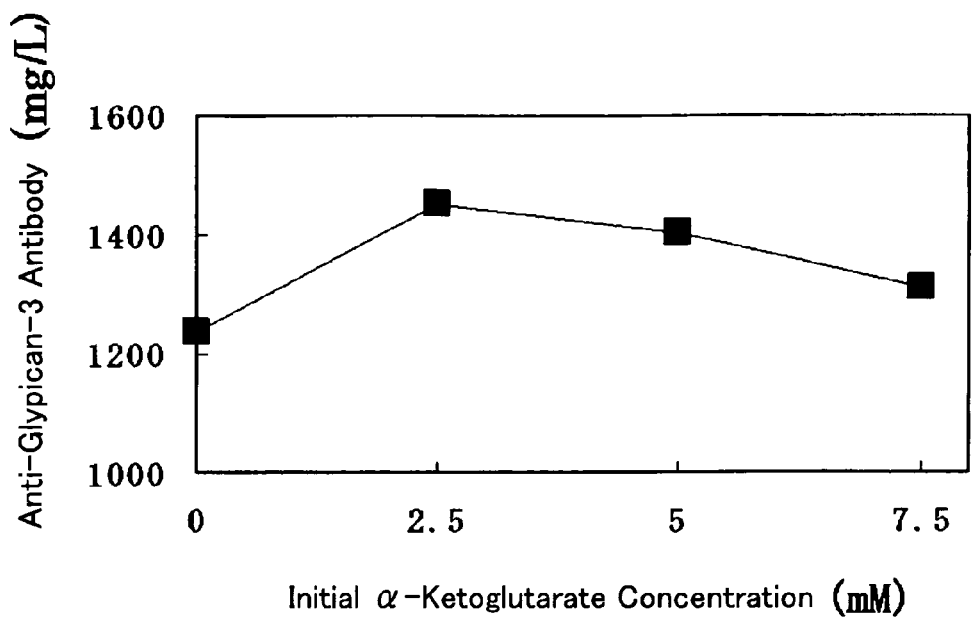
FIG. 22 shows the anti-glypican-3 antibody yield of TA41, a TauT/ALT co-expressing strain, on day 14 of fed-batch culture in a shaker. The antibody yield was increased by addition of α-ketoglutarate.

The anti-glypican-3 antibody yield of TA41, a TauT/ALT1 co-expressing strain, on day 14 of the fed-batch culture in a 50 ml shaker flask was increased by addition of α-ketoglutarate which, like alanine, served as a substrate for ALT (FIG. 22). The anti-glypican-3 antibody yield on day 14 of the culture was 1452 mg/L in the presence of 2.5 mM α-ketoglutarate, and 1239 mg/L in the absence of α-ketoglutarate.

The above results suggest that cells capable of high-yield antibody production at the late stage of culture can be obtained by artificially expressing ALT 1.

The present invention is applicable to any antibody-producing cell.

Referential Example 1

Cloning of CHO Cell-Derived Hamster Taurine Transporter Gene

Figure 8:
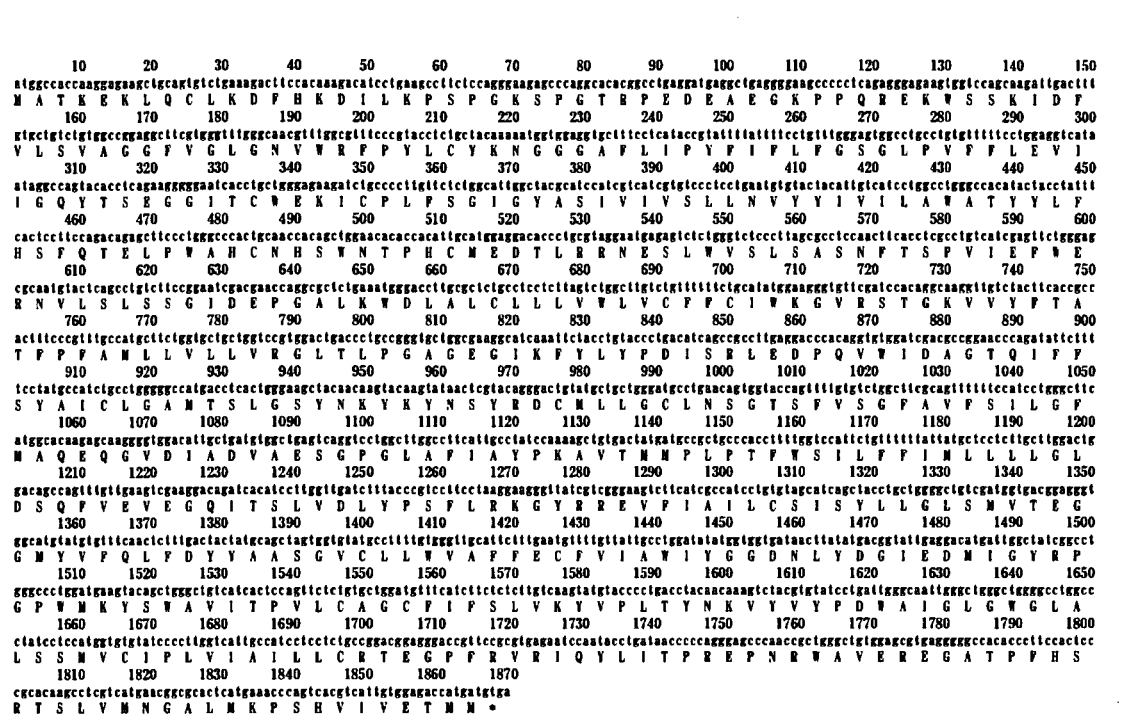
Figure 9:
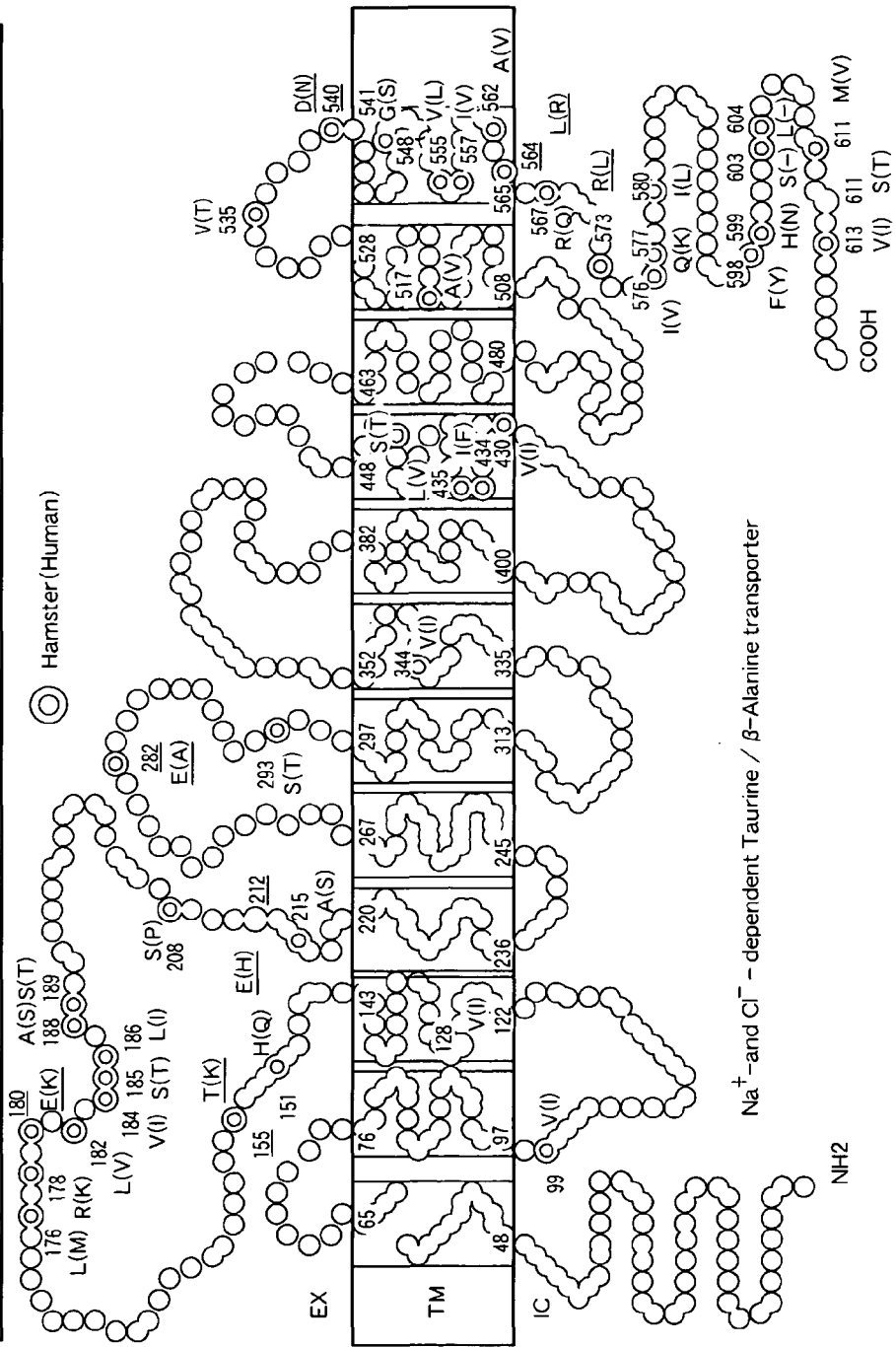
FIG. 9 is a taurine transporter membrane topology of a newly cloned, CHO cell-derived TauT.

Total RNA was extracted from anti-IL-6 receptor antibody-producing cells (A CHO DXB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster taurine transporter (TauT) gene was obtained by PCR using as a template the cDNA fragmented with three restriction enzymes, SalI, XhoI and EcoRI. As PCR primers, those containing the 5'-end and the 3'-end sequence conserved between rat and mouse TauTs were designed. The nucleotide sequence of the cloned gene was determined. From its homology with other TauT genes of known species, the cloned gene was confirmed to encode hamster TauT (FIG. 8). The amino acid sequence of hamster TauT has high homology with mouse TauT (96% identity), rat TauT (96% identity) and human TauT (93% identity); it was predicted that hamster TauT is a transporter with 12 transmembrane regions (FIG. 9).

Referential Example 2

Figure 10:
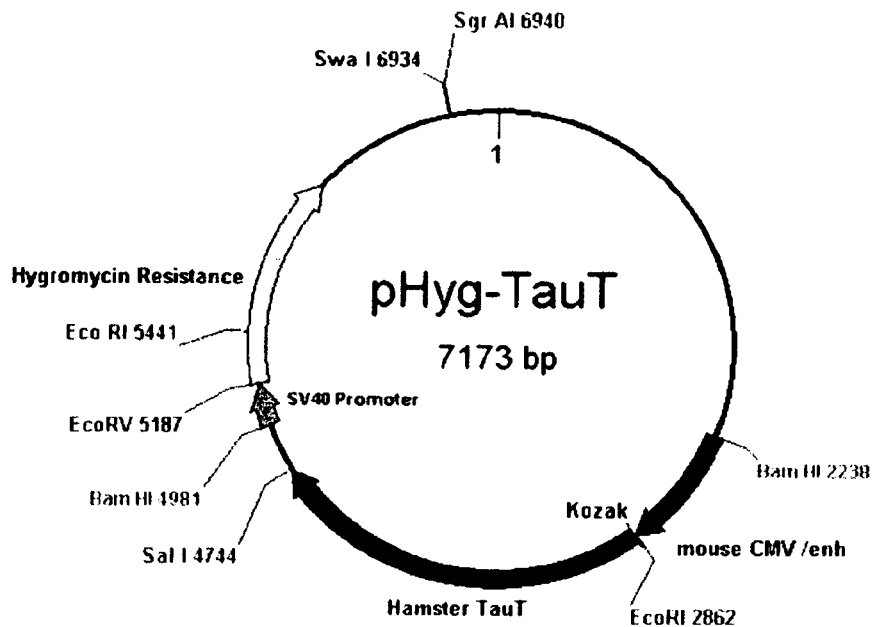
FIG. 10 shows a plasmid which was used for expressing hamster TauT (622 amino acids).
Figure 11:
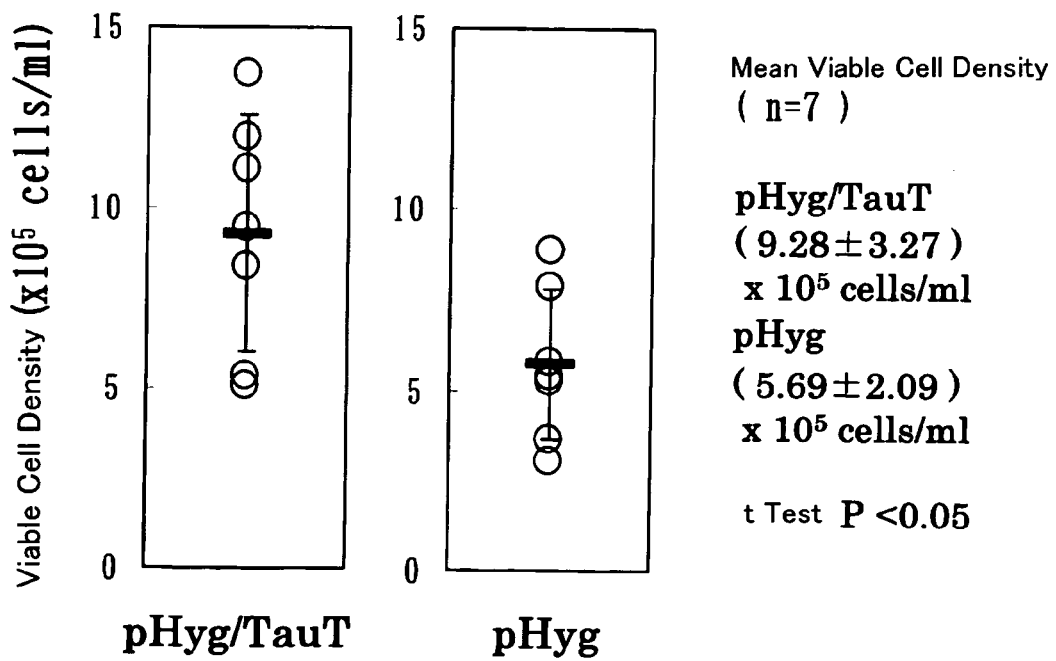
FIG. 11 shows viable cell density plots on day 7 of 50 ml shaker flask batch culture. The viable cell density in pHyg/TauT-transferred cell was superior to that in pHyg-transferred cell.
Figure 12:
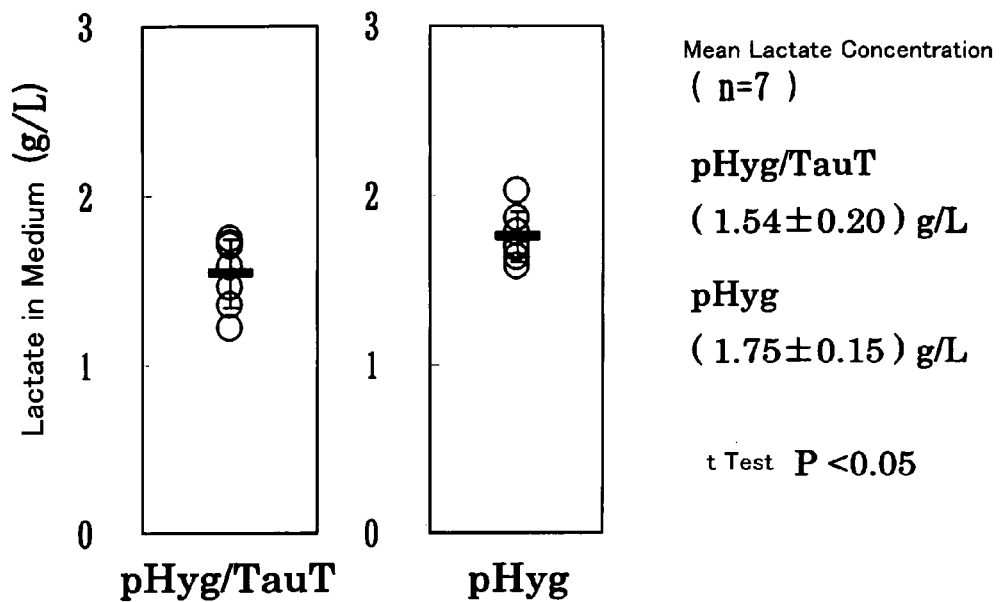
FIG. 12 shows lactate yield plots on day 7 of 50 ml shaker flask batch culture. pHyg/TauT-transferred cell produced less lactate, and was superior to pHyg-transferred cell.
Figure 13:
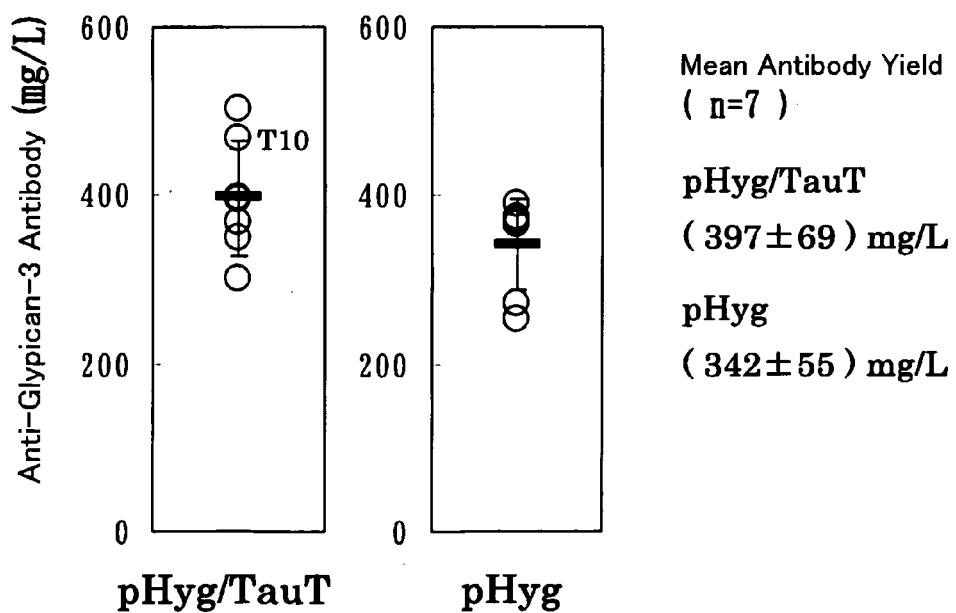
FIG. 13 shows anti-glypican-3 antibody yield plots on day 7 of 50 ml shaker flask batch culture. Four out of the 7 strains of pHyg/TauT-transferred cell showed antibody yields higher than the highest yield in pHyg-transferred cell.
Figure 14:
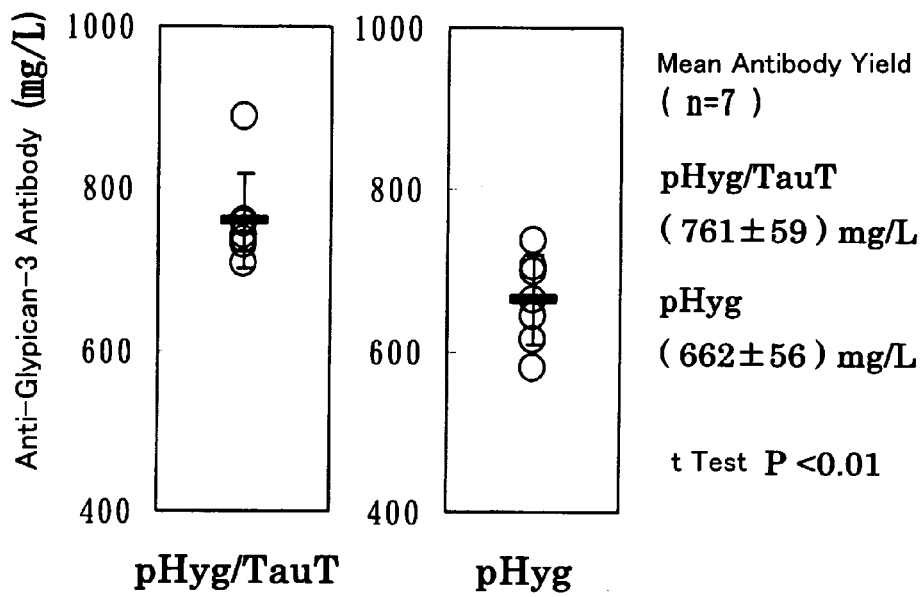
FIG. 14 shows anti-glypican-3 antibody yield plots on day 7 of 50 ml shaker flask fed-batch culture. The antibody yield in pHyg/TauT-transferred cell was superior to that in pHyg-transferred cell.
Figure 15:
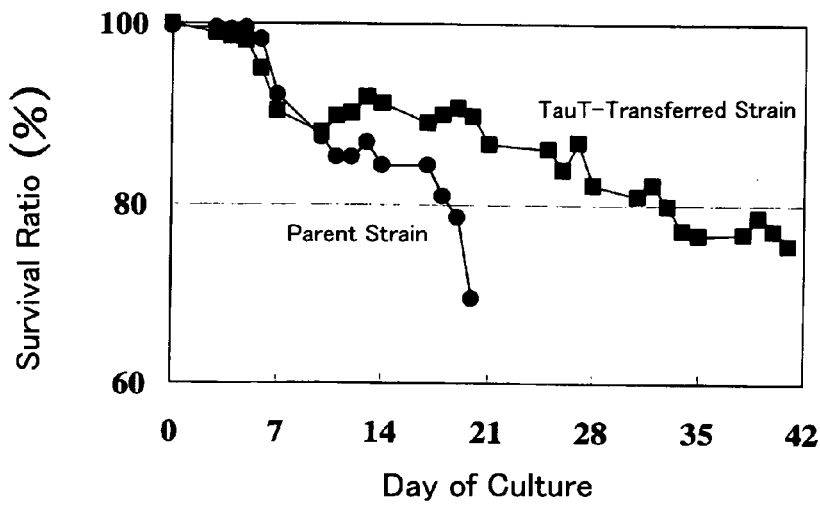
FIG. 15 is a graph showing the survival ratio of a pHyg/TauT-transferred cell T10 (which showed high growth ability) in 1 L jar fed-batch culture. The survival ratio of T10 was 80% or more even on day 32 of the culture.
Figure 16:
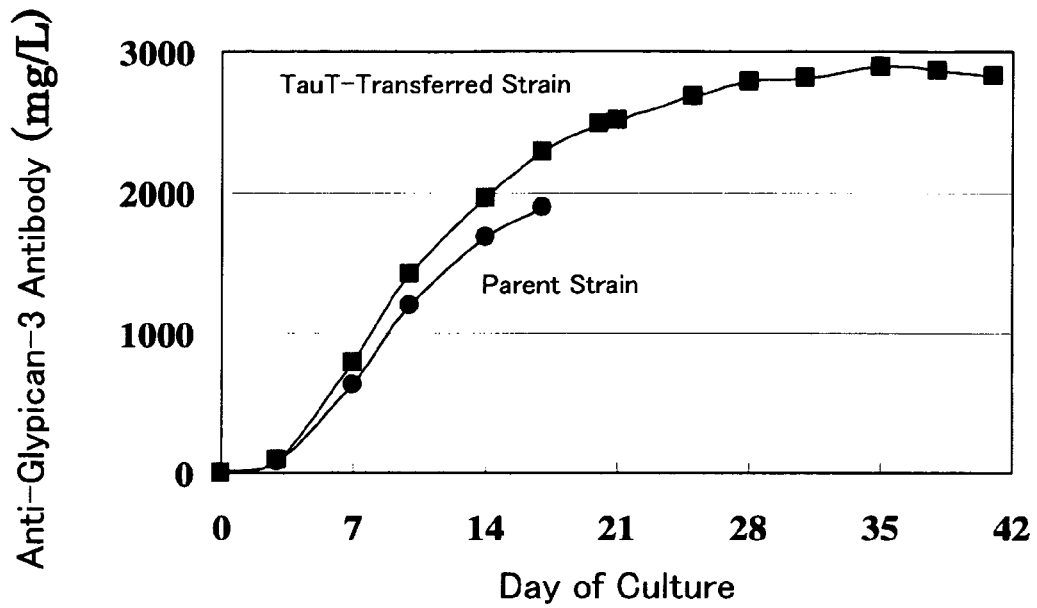
FIG. 16 is a graph showing the antibody yield of a pHyg/TauT-transferred cell T10 (which showed high growth ability during the expansion process in static culture) in 1 L jar fed-batch culture. The anti-glypican-3 antibody yield of T10 was 2.9 g/L on day 35 of the culture.
Figure 17:
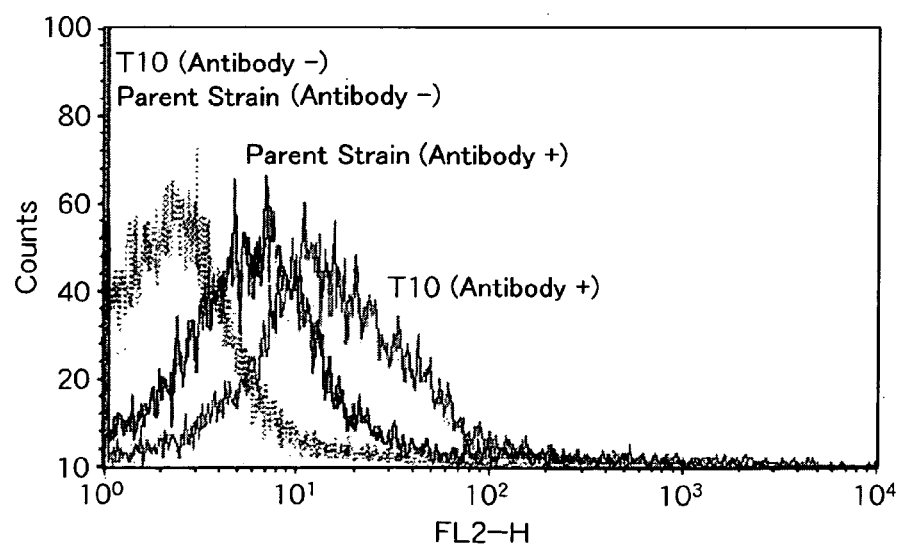
FIG. 17 shows the results of flow cytometric analysis indicating that TauT-transferred T10 cell is expressing TauT molecules on its cell membrane.

Increase in Viable Cell Density, Inhibition of Lactate Production and Increase in Antibody Yield, as Caused by Transfer of Hamster Taurine Transporter CMV promoter expression plasmid pHyg/TauT (FIG. 10) was constructed by adding Kozak sequence to the hamster TauT (hereinafter, TauT) gene obtained by cloning in Referential Example 1. Control plasmid pHyg without pHyg/TauT or TauT gene was introduced by electroporation into the parent strain anti-glypican-3 antibody producing CHO cell (see WO 2006/006693). After selection of expression plasmid-transferred cells in the presence of hygromycin (400 μg/ml), all of the stably growing cell strains were expanded (pHyg/TauT: 8 strains; pHyg: 7 strains). TauT mRNA was prepared. Subsequently, 7 strains were confirmed to express TauT more strongly than the parent strain by the TaqMan method; they were selected as pHyg/TauT transferred cells. The mean mRNA expression level of these transferred cells (7 strains) was about 40 times larger than the control (7 strains). Cells of the total 14 strains were subjected to batch culture and fed-batch culture in 50 ml shaker flasks with an initial cell density of $2 \times 10^5$ cells/ml. On day 7 of culture (late-stage), viable cell densities, lactate yields and anti-glypican-3 antibody yields in those strains were compared. In batch culture, growth inhibitory substances such as lactate accumulate in culture broth as cells grow and their growth is inhibited. However, the viable cell densities (FIG. 11) and lactate yields (FIG. 12) in pHyg/TauT transferred cells were superior to those in pHyg transferred cells (t test; $p < 0.05$). With respect to anti-glypican-3 antibody yield, 4 out of the 7 strains of pHyg/TauT-transferred cell showed antibody yields higher than the highest yield in pHyg-transferred cell (FIG. 13). Further, since superiority of pHyg/TauT transferred cells in anti-glypican-3 antibody yield became more evident (t test; $P < 0.01$; FIG. 14) in fed-batch culture, pHyg/TauT transferred T10 strain (which showed the highest growth ability among the above 4 strains) and the parent strain were subjected to fed-batch culture in 1 L jar. As a result, the viable ratio of T10 was maintained at 80% or more even on day 32 of culture (FIG. 15), with inhibited lactate production. Consequently, its anti-glypican-3 antibody yield achieved 2.9 g/L on day 35 of culture (FIG. 16). It was confirmed by flow cytometric analysis that TauT-transferred T10 cell was expressing TauT molecules on the cell membrane (FIG. 17). These results suggest that by artificially expressing hamster Taut, it is possible to raise the potential of antibody-producing cells and create strains capable of enhanced antibody production.

Referential Example 3

Inhibition of Ammonia Production, Taurine Uptake, Increase in Glutamine Consumption and Taurine Non-Dependent Antibody Yield in Hamster TauT Transferred Strains The parent strain and pHyg/TauT transferred strain were fed-batch cultured in 1 L jar with an initial cell density of 2×10⁵ cells/ml. A part of the culture broth containing 450×10⁵ cells was taken from the jar at appropriate time points. After the culture supernatant was separated by centrifugation, 1 ml of cooled sterile water containing a protease inhibitor (Complete Mini; Roche Diagnostics; Protease inhibitor cocktail tablets) was added to the cell pellet. Then, the cells were completely disrupted on ice in a sonicator (MISONIX ASTRASON MODEL XL2020) with a set of 5 seconds pulse-on and 5 seconds pulse-off being repeated 12 times. The total volume of the thus treated cells was applied to a centrifugal filter unit to thereby prepare a filtrate with a molecular weight of 5000 or less. This filtrate was used as a sample for determining intracellular amino acids. Each sample was subjected to detection and comparison of absorbance at 570 nm using a ninhydrin reagent L-8500 set (Wako Pure Chemical Industries) and an improved model of Hitachi fully automated amino acid analyzer (L-8500). Thus, various amino acid concentrations in samples were determined. Since the concentrations of amino acids and ammonia in culture broth were directly measured values, concentration comparisons in the order of μM were performed. On the other hand, since intracellular concentrations were obtained after addition of 1 ml of cooled sterile water to the cell pellet and sonication thereof, the measured concentrations of various amino acids and ammonia were converted into values per cell, followed by comparison of the converted values. To determine the ammonia concentration ratios shown in FIG. 18, the detected ammonia value per 450×10⁵ cells in the parent strain at the start of 1 L jar fed-batch culture was taken as 1 and compared with detected values at the start of the culture and on days 6, 12 and 18 of the culture in the transferred strain. The taurine values in FIG. 19 and the glutamine values in FIG. 20 were also determined by the above-described amino acid analysis.

Figure 18:
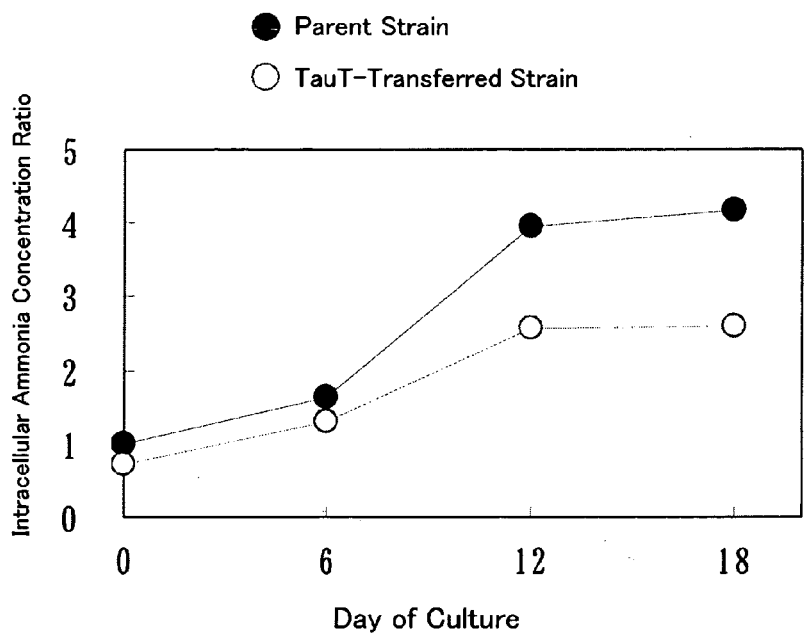
FIG. 18 is a graph showing intracellular ammonia contents (concentration ratios) in 1 L jar fed-batch culture. The ammonia inhibition in pHyg/TauT-transferred strains was remarkable compared to the parent strain.
Figure 19:
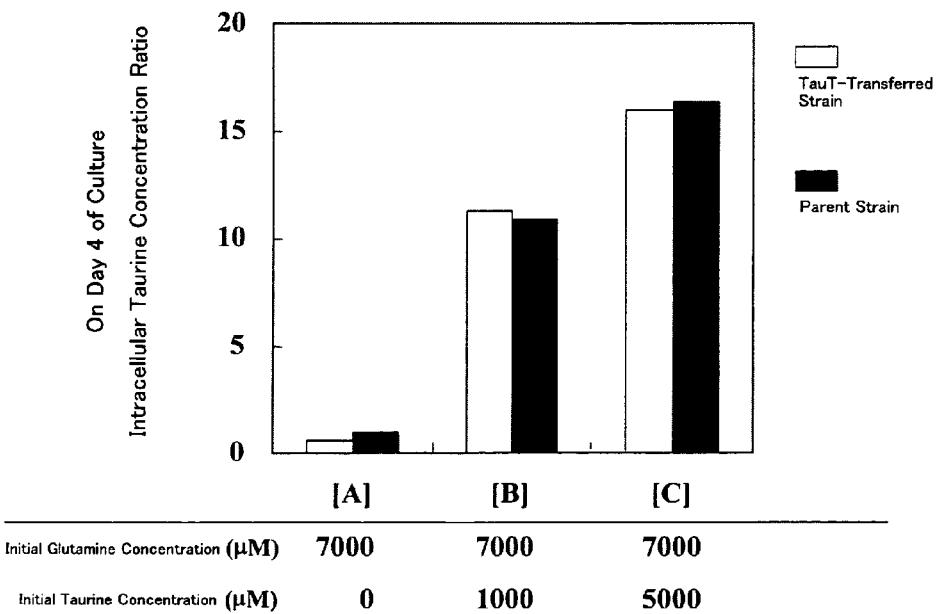
FIG. 19 is a graph showing that taurine is taken into cells depending on the taurine concentration in the medium. No difference was observed in taurine uptake between pHyg/TauT-transferred strains and the parent strain.

As a result, the intracellular ammonia in pHyg/TauT transferred strain was maintained at a low concentration at the late stage of culture; it is believed that this contributes to high antibody yield (FIG. 18).

Intracellular taurine concentration ratios were determined in the same manner as described above for ammonia concentrations (FIG. 19), except that the detected ammonia value per 200×10⁵ cells in the parent strain on day 4 of 50 ml shaker batch culture was taken as 1.

Figure 20:
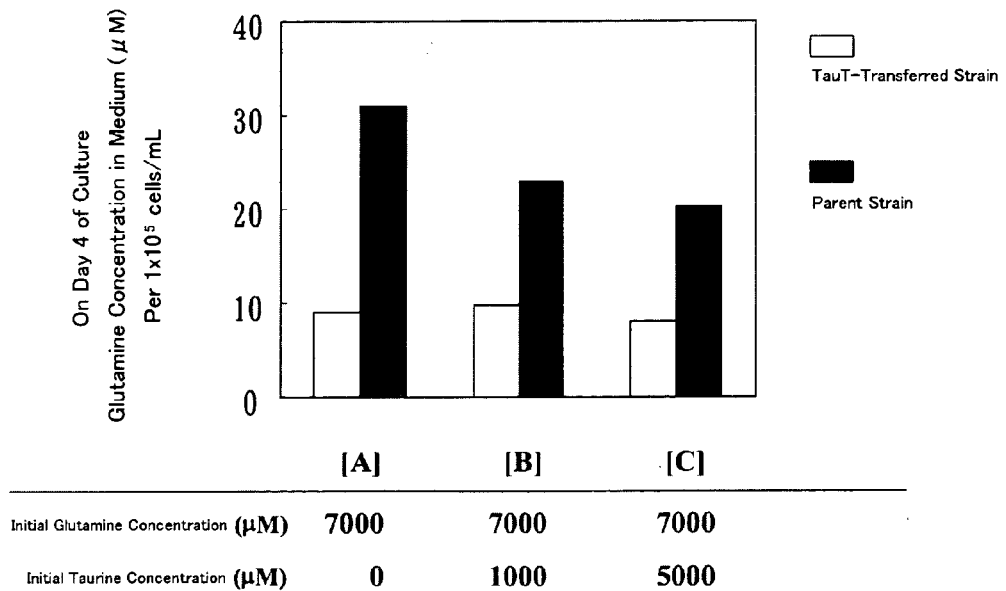
FIG. 20 is a graph showing the consumption of glutamine in the medium. Compared to the parent strain, pHyg/TauT-transferred strains showed a remarkably high glutamine consumption/cell without depending on the taurine concentration in the medium.

As a result, it was found that pHyg/TauT transferred strain had taken up taurine in a manner dependent on the amount of taurine added and that its uptake was almost equal to that by the parent strain. However, as shown in FIG. 20, glutamine consumption in pHyg/TauT transferred strain was remarkably high compared to the parent strain and was not dependent on the initial taurine concentration. It has been reported that glutamine improves cell growth, survival ratio and antibody production ability in hybridomas to thereby raise their antibody yields (Enzyme and Microbial Technology 17:47-55, 1995). Therefore, the antibody production enhancement effect of pHyg/TauT transferred strain may be caused by taurine transporter-mediated uptake of amino acids other than taurine (e.g., glutamine). The glutamine concentrations were obtained by converting the values determined by amino acid analysis of the culture broth on day 4 of culture in FIG. 19 into values per 1×10⁵ cells.

Figure 21:
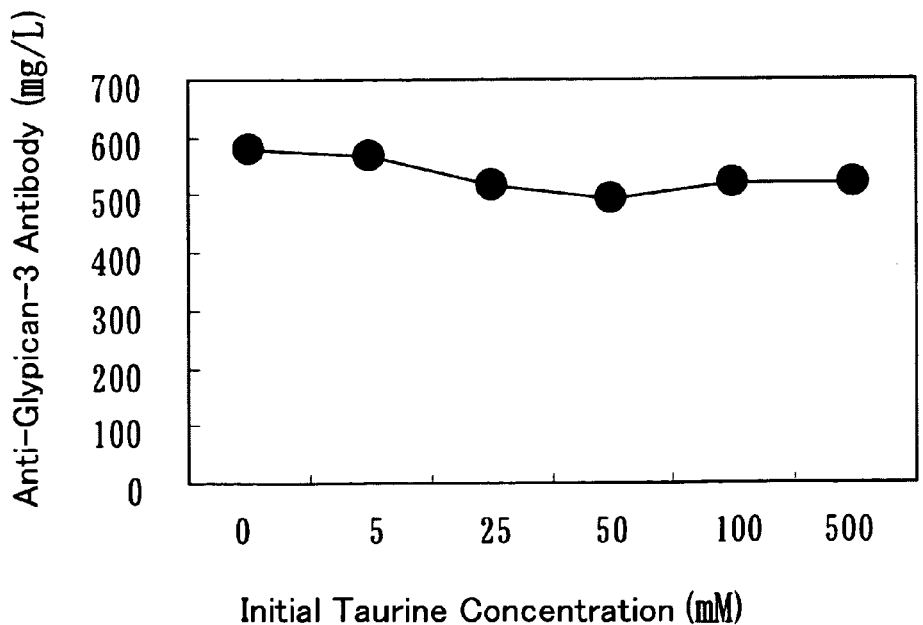
FIG. 21 is a graph showing that the anti-glypican-3 antibody yields of pHyg/TauT-transferred strains are almost equal without depending on the initial taurine concentration in the medium.

Actually, anti-glypican-3 antibody yield was not dependent on the initial taurine concentration (0-500 mM (62.575 g/L)) at the start of 50 ml shaker fed-batch culture (FIG. 21). No significant difference was observed in the parent strains in the effect of initial taurine concentration on antibody yield.

The results described so far suggest that TauT strongly expressing strains have high antibody production ability even if the medium does not contain taurine at the start of culture and that there is a possibility that such strains also promote uptake of amino acids other than taurine.

The present invention is applicable to any antibody-producing cell.

All publications, patent and patent applications cited herein are incorporated herein by reference in their entirety.

Industrial Applicability

The present invention is applicable to production of polypeptides.

Sequence Listing Free Text

<SEQ ID NO: 1>
SEQ ID NO: 1 shows the nucleotide sequence of a gene encoding human alanine aminotransferase (ALT1) (KEGG/ENZYME: 2.6.1.2/*Homo sapiens* (human): 2875).

<SEQ ID NO: 2>
SEQ ID NO: 2 shows the amino acid sequence of human alanine aminotransferase (ALT1) (KEGG/ENZYME: 2.6.1.2/*Homo sapiens* (human): 2875)

<SEQ ID NO: 3>
SEQ ID NO: 3 shows the nucleotide sequence of a gene encoding human alanine aminotransferase mutant (ALT2) (KEGG/ENZYME: 2.6.1.2/*Homo sapiens* (human): 84706).

<SEQ ID NO: 4>
SEQ ID NO: 4 shows the amino acid sequence of human alanine aminotransferase mutant (ALT2) (KEGG/ENZYME: 2.6.1.2/*Homo sapiens* (human): 84706).

<SEQ ID NO: 5>
SEQ ID NO: 5 shows the nucleotide sequence of a gene encoding mouse alanine aminotransferase (ALT1) (KEGG/ENZYME: 2.6.1.2/*Mus musculus* (mouse): 76282).

<SEQ ID NO: 6>
SEQ ID NO: 6 shows the amino acid sequence of mouse alanine aminotransferase (ALT1) (KEGG/ENZYME: 2.6.1.2/*Mus musculus* (mouse): 76282).

<SEQ ID NO: 7>
SEQ ID NO: 7 shows the nucleotide sequence of a gene encoding mouse alanine aminotransferase mutant (ALT2) (KEGG/ENZYME: 2.6.1.2/*Mus musculus* (mouse): 108682).

<SEQ ID NO: 8>
SEQ ID NO: 8 shows the amino acid sequence of mouse alanine aminotransferase mutant (ALT2) (KEGG/ENZYME: 2.6.1.2/*Mus musculus* (mouse): 108682).

<SEQ ID NO: 9>
SEQ ID NO: 9 shows the nucleotide sequence of a gene encoding rat alanine aminotransferase (ALT1) (KEGG/ENZYME: 2.6.1.2/*Rattus norvegicus* (rat): 81670).

<SEQ ID NO: 10>
SEQ ID NO: 10 shows the amino acid sequence of rat alanine aminotransferase (ALT1) (KEGG/ENZYME: 2.6.1.2/*Rattus norvegicus* (rat): 81670).

<SEQ ID NO: 11>
SEQ ID NO: 11 shows the nucleotide sequence of a gene encoding dog alanine aminotransferase (ALT1) (KEGG/ENZYME: 2.6.1.2/*Canis familiaris* (dog): 609510).

<SEQ ID NO: 12>
SEQ ID NO: 12 shows the amino acid sequence of dog alanine aminotransferase (ALT1) (KEGG/ENZYME: 2.6.1.2/*Canis familiaris* (dog): 609510).

<SEQ ID NO: 13>
SEQ ID NO: 13 shows the nucleotide sequence of a gene encoding African clawed frog alanine aminotransferase (ALT 1) (KEGG/ENZYME: 2.6.1.2/*Xenopus laevis* (African clawed frog): 444533).

<SEQ ID NO: 14>

SEQ ID NO: 14 shows the amino acid sequence of African clawed frog alanine aminotransferase (ALT1) (KEGG/ENZYME: 2.6.1.2/*Xenopus laevis* (African clawed frog): 444533).

<SEQ ID NO: 15>

SEQ ID NO: 15 shows the nucleotide sequence of a gene encoding fruit fly alanine aminotransferase (ALT1) (KEGG/ENZYME: 2.6.1.2/*Drosophila melanogaster* (fruit fly): Dmel_CG1640).

<SEQ ID NO: 16>

SEQ ID NO: 16 shows the amino acid sequence of fruit fly alanine aminotransferase (ALT 1) (KEGG/ENZYME: 2.6.1.2/*Drosophila melanogaster* (fruit fly): Dmel_CG1640).

<SEQ ID NO: 17>

SEQ ID NO: 17 shows the nucleotide sequence of a gene encoding nematode alanine aminotransferase (ALT1) (KEGG/ENZYME: 2.6.1.2/*Caenorhabditis elegans* (nematode): C32F10.8).

<SEQ ID NO: 18>

SEQ ID NO: 18 shows the amino acid sequence of nematode alanine aminotransferase (ALT 1) (KEGG/ENZYME: 2.6.1.2/*Caenorhabditis elegans* (nematode): C32F10.8).

<SEQ ID NO: 19>

SEQ ID NO: 19 shows the nucleotide sequence of a gene encoding one of two kinds of Japanese rice alanine aminotransferases (KEGG/ENZYME: 2.6.1.2/*Oryza sativa* japonica (Japanese rice): 4342210).

<SEQ ID NO: 20>

SEQ ID NO: 20 shows the amino acid sequence of one of two kinds of Japanese rice alanine aminotransferases (KEGG/ENZYME: 2.6.1.2/*Oryza sativa* japonica (Japanese rice): 4342210).

<SEQ ID NO: 21>

SEQ ID NO: 21 shows the nucleotide sequence of a gene encoding one of two kinds of Japanese rice alanine aminotransferases (KEGG/ENZYME: 2.6.1.2/*Oryza sativa* japonica (Japanese rice): 4348524).

<SEQ ID NO: 22>

SEQ ID NO: 22 shows the amino acid sequence of one of two kinds of Japanese rice alanine aminotransferases (KEGG/ENZYME: 2.6.1.2/*Oryza sativa* japonica (Japanese rice): 4348524).

<SEQ ID NO: 23>

SEQ ID NO: 23 shows the nucleotide sequence of a gene encoding *Cyanidioschyzon merolae* alanine aminotransferase (KEGG/ENZYME: 2.6.1.2/*Cyanidioschyzon merolae*: CMM066C)

<SEQ ID NO: 24>

SEQ ID NO: 24 shows the amino acid sequence of *Cyanidioschyzon merolae* alanine aminotransferase (KEGG/ENZYME: 2.6.1.2/Cyanidioschyzon merolae: CMM066C.

<SEQ ID NO: 25>

SEQ ID NO: 25 shows the nucleotide sequence of a gene encoding *Saccharomyces cerevisiae* alanine aminotransferase (ALT1) (KEGG/ENZYME: 2.6.1.2/*Saccharomyces cerevisiae*: YLR089C).

<SEQ ID NO: 26>

SEQ ID NO: 26 shows the amino acid sequence of *Saccharomyces cerevisiae* alanine aminotransferase (ALT 1) (KEGG/ENZYME: 2.6.1.2/*Saccharomyces cerevisiae*: YLR089C).

<SEQ ID NO: 27>

SEQ ID NO: 27 shows the nucleotide sequence of a gene encoding *Saccharomyces cerevisiae* alanine aminotransferase mutant (ALT2) (KEGG/ENZYME: 2.6.1.2/*Saccharomyces cerevisiae*: YDR111C).

<SEQ ID NO: 28>

SEQ ID NO: 28 shows the amino acid sequence of *Saccharomyces cerevisiae* alanine aminotransferase mutant (ALT2) (KEGG/ENZYME: 2.6.1.2/*Saccharomyces cerevisiae*: YDR111C).

<SEQ ID NO: 29>

SEQ ID NO: 29 shows the nucleotide sequence of a gene encoding Ashbya gossypii alanine aminotransferase KEGG/ENZYME: 2.6.1.2/Ashbya gossypii (*Eremothecium gossypii*): AGOS_AGRO85W).

<SEQ ID NO: 30>

SEQ ID NO: 30 shows the amino acid sequence of *Ashbya gossypii* alanine aminotransferase (KEGG/ENZYME: 2.6.1.2/Ashbya gossypii (*Eremothecium gossypii*): AGOS_AGRO85W).

<SEQ ID NO: 31>

SEQ ID NO: 31 shows the nucleotide sequence of a gene encoding *Candida albicans* alanine aminotransferase (KEGG/ENZYME: 2.6.1.2/*Candida albicans*: CaO19_346).

<SEQ ID NO: 32>

SEQ ID NO: 32 shows the amino acid sequence of *Candida albicans* alanine aminotransferase (KEGG/ENZYME: 2.6.1.2/*Candida albicans*: CaO19_346).

<SEQ ID NO: 33>

SEQ ID NO: 33 shows the nucleotide sequence of a gene encoding *Schizosaccharomyces pombe* alanine aminotransferase (KEGG/ENZYME: 2.6.1.2/*Schizosaccharomyces pombe*: SPBC582.08).

<SEQ ID NO: 34>

SEQ ID NO: 34 shows the amino acid sequence of *Schizosaccharomyces pombe* alanine aminotransferase (KEGG/ENZYME: 2.6.1.2/*Schizosaccharomyces pombe*: SPBC582.08).

<SEQ ID NO: 35>

SEQ ID NO: 35 shows the nucleotide sequence of a gene encoding *Aspergillus nidulans* alanine aminotransferase (KEGG/ENZYME: 2.6.1.2/*Aspergillus nidulans*: AN1923.2).

<SEQ ID NO: 36>

SEQ ID NO: 36 shows the amino acid sequence of *Aspergillus nidulans* alanine aminotransferase (KEGG/ENZYME: 2.6.1.2/*Aspergillus nidulans*: AN1923.2).

<SEQ ID NO: 37>

SEQ ID NO: 37 shows the nucleotide sequence of a gene encoding *Aspergillus fumigatus* alanine aminotransferase (KEGG/ENZYME: 2.6.1.2/*Aspergillus fumigatus*: AFUA_6G07770).

<SEQ ID NO: 38>

SEQ ID NO: 38 shows the amino acid sequence of *Aspergillus fumigatus* alanine aminotransferase (KEGG/ENZYME: 2.6.1.2/*Aspergillus fumigatus*: AFUA_6G07770).

<SEQ ID NO: 39>

SEQ ID NO: 39 shows the nucleotide sequence of a gene encoding *Aspergillus oryzae* alanine aminotransferase (KEGG/ENZYME: 2.6.1.2/*Aspergillus oryzae*: AO090003000164).

<SEQ ID NO: 40>

SEQ ID NO: 40 shows the amino acid sequence of *Aspergillus oryzae* alanine aminotransferase (KEGG/ENZYME: 2.6.1.2/*Aspergillus oryzae*: AO090003000164).

<SEQ ID NO: 41>

SEQ ID NO: 41 shows the nucleotide sequence of a gene encoding *Cryptococcus neoformans* alanine aminotransferase (KEGG/ENZYME: 2.6.1.2/*Cryptococcus neoformans* JEC21: CNG01490).

<SEQ ID NO: 42>

SEQ ID NO: 42 shows the amino acid sequence of *Cryptococcus neoformans* alanine aminotransferase (KEGG/ENZYME: 2.6.1.2/*Cryptococcus neoformans* JEC21: CNG01490).

<SEQ ID NO: 43>

SEQ ID NO: 43 shows the nucleotide sequence of a gene encoding *Dictyostelium discoideum* alanine aminotransferase (KEGG/ENZYME: 2.6.1.2/*Dictyostelium discoideum*: DDB_0232139).

<SEQ ID NO: 44>

SEQ ID NO: 44 shows the amino acid sequence of *Dictyostelium discoideum* alanine aminotransferase (KEGG/ENZYME: 2.6.1.2/*Dictyostelium discoideum*: DDB_0232139).

<SEQ ID NO: 45>

SEQ ID NO: 45 shows the nucleotide sequence of a gene encoding *Trypanosoma brucei* alanine aminotransferase (KEGG/ENZYME: 2.6.1.2/*Trypanosoma brucei*: Tb927.1.3950).

<SEQ ID NO: 46>

SEQ ID NO: 46 shows the amino acid sequence of *Trypanosoma brucei* alanine aminotransferase (KEGG/ENZYME: 2.6.1.2/*Trypanosoma brucei*: Tb927.1.3950)<

SEQ ID NO: 47>

SEQ ID NO: 47 shows the nucleotide sequence of a gene encoding *Leishmania major* alanine aminotransferase (KEGG/ENZYME: 2.6.1.2/*Leishmania major*: LmjF12.0630).

<SEQ ID NO: 48>

SEQ ID NO: 48 shows the amino acid sequence of *Leishmania major* alanine aminotransferase (KEGG/ENZYME: 2.6.1.2/*Leishmania major*: LmjF12.0630).

<SEQ ID NO: 49>

SEQ ID NO: 49 shows the nucleotide sequence of a gene encoding one of two kinds of *Entamoeba histolytica* alanine aminotransferases (KEGG/ENZYME: 2.6.1.2/*Entamoeba histolytica*: 233.t00009).

<SEQ ID NO: 50>

SEQ ID NO: 50 shows the amino acid sequence of one of two kinds of *Entamoeba histolytica* alanine aminotransferases (KEGG/ENZYME: 2.6.1.2/*Entamoeba histolytica*: 233.t00009).

<SEQ ID NO: 51>

SEQ ID NO: 51 shows the nucleotide sequence of a gene encoding one of two kinds of *Entamoeba histolytica* alanine aminotransferases (KEGG/ENZYME: 2.6.1.2/*Entamoeba histolytica*: 24.t00016).

<SEQ ID NO: 52>

SEQ ID NO: 52 shows the amino acid sequence of one of two kinds of *Entamoeba histolytica* alanine aminotransferases (KEGG/ENZYME: 2.6.1.2/*Entamoeba histolytica*: 24.t00016).

<SEQ ID NO: 53>

SEQ ID NO: 53 shows the nucleotide sequence of a gene encoding one of four kinds of *Trypanosoma cruzi* alanine aminotransferases (KEGG/ENZYME: 2.6.1.2/*Trypanosoma cruzi*: 506529.420).

<SEQ ID NO: 54>

SEQ ID NO: 54 shows the amino acid sequence of one of four kinds of *Trypanosoma cruzi* alanine aminotransferases (KEGG/ENZYME: 2.6.1.2/*Trypanosoma cruzi*: 506529.420).

<SEQ ID NO: 55>

SEQ ID NO: 55 shows the nucleotide sequence of a gene encoding one of four kinds of *Trypanosoma cruzi* alanine aminotransferases (KEGG/ENZYME: 2.6.1.2/*Trypanosoma cruzi*: 506529.430).

<SEQ ID NO: 56>

SEQ ID NO: 56 shows the amino acid sequence of one of four kinds of *Trypanosoma cruzi* alanine aminotransferases (KEGG/ENZYME: 2.6.1.2/*Trypanosoma cruzi*: 506529.430).

<SEQ ID NO: 57>

SEQ ID NO: 57 shows the nucleotide sequence of a gene encoding one of four kinds of *Trypanosoma cruzi* alanine aminotransferases (KEGG/ENZYME: 2.6.1.2/*Trypanosoma cruzi*: 510889.120)

<SEQ ID NO: 58>

SEQ ID NO: 58 shows the amino acid sequence of one of four kinds of *Trypanosoma cruzi* alanine aminotransferases (KEGG/ENZYME: 2.6.1.2/*Trypanosoma cruzi*: 510889.120).

<SEQ ID NO: 59>

SEQ ID NO: 59 shows the nucleotide sequence of a gene encoding one of four kinds of *Trypanosoma cruzi* alanine aminotransferases (KEGG/ENZYME: 2.6.1.2/*Trypanosoma cruzi*: 510889.140).

<SEQ ID NO: 60>

SEQ ID NO: 60 shows the amino acid sequence of one of four kinds of *Trypanosoma cruzi* alanine aminotransferases (KEGG/ENZYME: 2.6.1.2/*Trypanosoma cruzi*: 510889.140).

<SEQ ID NO: 61>

SEQ ID NO: 61 shows the nucleotide sequence of a gene encoding hamster taurine transporter.

<SEQ ID NO: 62>

SEQ ID NO: 62 shows the amino acid sequence of hamster taurine transporter.

<SEQ ID NO: 63>

SEQ ID NO: 63 shows the nucleotide sequence of a gene encoding rat taurine transporter (GenBank NM_017206).

<SEQ ID NO: 64>

SEQ ID NO: 64 shows the amino acid sequence of rat taurine transporter (GenBank NM 017206).

<SEQ ID NO: 65>

SEQ ID NO: 65 shows the nucleotide sequence of a gene encoding mouse taurine transporter (GenBank NM_009320).

<SEQ ID NO: 66>

SEQ ID NO: 66 shows the amino acid sequence of mouse taurine transporter (GenBank NM 009320).

<SEQ ID NO: 67>

SEQ ID NO: 67 shows the nucleotide sequence of a gene encoding human taurine transporter (GenBank NM_003043).

<SEQ ID NO: 68>

SEQ ID NO: 68 shows the amino acid sequence of human taurine transporter (GenBank NM_003043).

The invention claimed is:

1. A method of producing an antibody, comprising culturing an animal cell which expresses alanine aminotransferase and has a transferred DNA encoding the antibody and thereby allowing the animal cell to produce the antibody,
   wherein the animal cell is a cell transformed with DNA encoding the alanine aminotransferase; and
   wherein the alanine aminotransferase is any one of the following (a)-(c):
   (a) a polypeptide having the amino acid sequence as shown in SEQ ID NO: 2;
   (b) a polypeptide which has an amino acid sequence derived from the amino acid sequence as shown in SEQ ID NO: 2 by substitution, deletion, addition and/or insertion of 1-5 amino acid residues and yet has alanine aminotransferase activity; and
   (c) a polypeptide having 99% or more amino acid sequence homology with the amino acid sequence as shown in SEQ ID NO: 2 and yet having alanine aminotransferase activity.

2. The method of claim 1, wherein the animal cell further expresses a taurine transporter, and wherein the animal cell is a cell into which DNA encoding a taurine transporter has been transferred.

3. The method of claim 1, wherein the cell is a Chinese hamster ovary cell.

4. A cultured cell transformed with DNA encoding alanine aminotransferase and a transferred DNA encoding a desired antibody.

5. The cultured cell according to claim 4, which further has a transferred DNA encoding a taurine transporter.

6. A cultured cell transformed with DNA encoding alanine aminotransferase and DNA encoding a taurine transporter.

7. A method of producing a desired polypeptide, comprising culturing in an α-ketoglutarate-containing medium a cell transformed with DNA encoding alanine aminotransferase and which has a transferred DNA encoding the desired polypeptide and thereby allowing the cell to produce said desired polypeptide, wherein the alanine aminotransferase is any one of the following (a)-(c):
   (a) a polypeptide having the amino acid sequence as shown in SEQ ID NO: 2;
   (b) a polypeptide which has an amino acid sequence derived from the amino acid sequence as shown in SEQ ID NO: 2 by substitution, deletion, addition and/or insertion of 1-5 amino acid residues and yet has alanine aminotransferase activity; and
   (c) a polypeptide having 99% or more amino acid sequence homology with the amino acid sequence as shown in SEQ ID NO: 2.

* * * * *